United States Patent [19]
Goulet et al.

[11] Patent Number: 5,247,076
[45] Date of Patent: Sep. 21, 1993

[54] IMIDAZOLIDYL MACROLIDES HAVING IMMUNOSUPPRESSIVE ACTIVITY

[75] Inventors: Mark Goulet, Westfield; Peter J. Sinclair, Highland Park; Frederick Wong, Glen Ridge; Matthew J. Wyvratt, Mountainside, all of N.J.

[73] Assignee: Merck & Co., Inc., Rahway, N.J.

[21] Appl. No.: 921,181

[22] Filed: Aug. 4, 1992

Related U.S. Application Data

[63] Continuation-in-part of Ser. No. 756,633, Sep. 9, 1991, abandoned.

[51] Int. Cl.$^5$ ............... C07D 498/16; A61K 31/395
[52] U.S. Cl. ................................................ 540/456
[58] Field of Search ........................................ 540/456

[56] References Cited

U.S. PATENT DOCUMENTS

| | | | |
|---|---|---|---|
| 5,064,835 | 11/1991 | Bochis et al. | 514/291 |
| 5,110,811 | 5/1992 | Okuhara et al. | 514/183 |
| 5,118,677 | 6/1992 | Caufield | 514/183 |
| 5,118,678 | 6/1992 | Kao et al. | 514/183 |

FOREIGN PATENT DOCUMENTS

| | | | |
|---|---|---|---|
| 0402931 | 12/1990 | European Pat. Off. | |
| 0428365 | 5/1991 | European Pat. Off. | 514/291 |
| 0463690 | 1/1992 | European Pat. Off. | 514/291 |
| 2245891A | 1/1992 | United Kingdom | 514/291 |
| WO92/00313 | 1/1992 | World Int. Prop. O. | 514/291 |
| WO92/03441 | 3/1992 | World Int. Prop. O. | 514/291 |
| WO92/05179 | 4/1992 | World Int. Prop. O. | 514/291 |

OTHER PUBLICATIONS

Barton, et al., *J. Chem. Soc., Chem. Commun.*, 65–66 (1986) (I).

Barton, et al., *Tetrahedron Lett.*, 27(31), 3615–3618 (1986) (I).

*Primary Examiner*—Robert T. Bond
*Attorney, Agent, or Firm*—Charles M. Caruso; J. Eric Thies

[57] ABSTRACT

Imidazolidyl macrolides of the general structural Formula I:

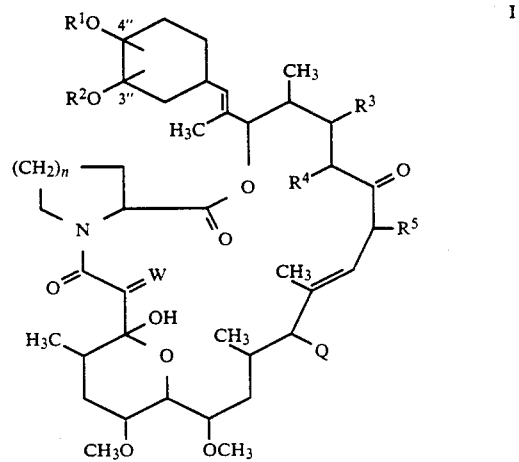

have been prepared from suitable precursors by alkylation and/or arylation at C-3″ and/or C-4″ of the cyclohexyl ring. These macrolide immunosuppressants are useful in a mammalian host for the treatment of autoimmune diseases, infectious diseases the prevention of rejection of foreign organ transplants and/or related afflictions, diseases and illnesses.

13 Claims, No Drawings

IMIDAZOLIDYL MACROLIDES HAVING IMMUNOSUPPRESSIVE ACTIVITY

SUMMARY OF THE INVENTION

This application is a continuation-in-part of copending application Ser. No. 07/756,633, filed Sep. 9, 1991, now abandoned.

The present invention is related to imidazolidyl macrolides which are useful in a mammalian subject for the treatment of autoimmune diseases (such as juvenile-onset or recent-onset diabetes mellitus, multiple sclerosis, and rheumatoid arthritis, liver disease, posterior uveitis, allergic encephalomyelitis, and glomerulonephritis), immunodepression, infectious diseases and/or the prevention of rejection of foreign organ transplants, (e.g. bone marrow, kidney, liver, heart, skin, small-bowel, and pancreatic islet-cell transplants, including xeno transplants), the topical treatment of inflammatory and hyperproliferative skin diseases and cutaneous manifestations of immunologically-mediated illnesses (such as: psoriasis, atopical dermatitiis, contact dermatitis and further eczematous dermatitises, seborrhoeic dermatitis, *Lichen planus*, Pemphigus, bullous Pemphigoid, *Epidermolysis bullosa*, urticaria, angioedemas, vasculitides, erythemas, cutaneous eosinophilias, *Lupus erythematosus* or *Alopecia areata*), male pattern alopecia, alopecia senilis, reversible obstructive airways disease, particularly asthma, inflammation of mucosa and blood vessels, cytomegalovirus infection, multidrug resistance, idiopathic thromboytopenic purpura, Behcet's syndrome, conjunctivitis, Crohm's disease, Mooren's ulcer, uveitis, servere intraocular inflammation and/or hepatic injury associated with ischemia. In addition, some of the compounds of this invention may have antagonistic properties and so have utility in the reversal of immunosuppressive activity and/or diminishing the toxicity of other immunosuppressive agents.

More particularly, this invention relates to compounds of the general structural Formula I:

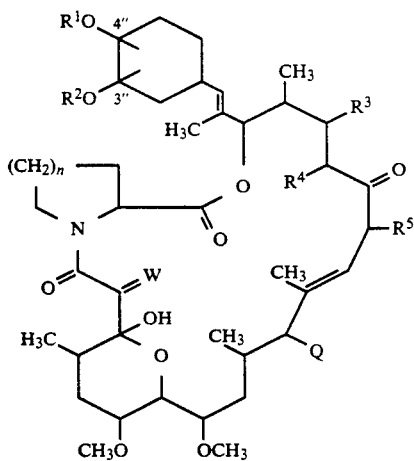

wherein $R^1$, $R^2$, $R^3$, $R^4$, $R^5$, Q, W and n are hereinafter defined.

This invention also relates to pharmaceutical compositions containing the compounds and to a method of use of the present compounds and other agents for the treatment and prevention of certain afflictions, diseases and illnesses.

BRIEF DESCRIPTION OF DISCLOSURES IN THE ART

Fujisawa United States, European and Japanese patents and applications (U.S. Pat. No. 4,894,366, issued Jan. 16, 1990, EPO Publication No. 0,184,162 and PBJ Disclosure 63-17884) and publications (*J. Am. Chem. Soc.*, 1987, 109, 5031 and *J. Antibiotics* 1987, 40, 1249) disclose 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (FR-900506) (FK-506) (L-679,934), 17-ethyl-1,14-dihydroxy-12-[2'-(4''-hydroxy-3''-methoxycyclohexyl)-1'-methyl-vinyl]-23,25-dimethoxy-13,19,21,27-tetramethyl-11,28-dioxa-4-azatricyclo[22.3.1.0$^{4,9}$]octacos-18-ene-2,3,10,16-tetraone (FR-900520) and related compounds which are the starting materials for the preparation of the compounds described. The synthetic preparation of the aforementioned starting material (FR-900506) has recently been reported (*J. Am. Chem. Soc.*, 1989, 111, 1157). A Sandoz European patent application (EPO Publication No. 0,356,399) discloses stereoisomers of FR-900506 and derivatives at the 17-position. Fisons European and WIPO patent applications (EPO Publication No. 0,323,042 and PCT Publication No. W089/05304) discloses various derivatives of FR-900506, FR-900520 and related compounds. A Sandoz European Patent application (EPO Publication No. 0,437,680) discloses chloro, bromo, iodo and azido derivatives of FR-900506, FR-900520 and related compounds. A Merck European Patent application (EPO Publication No. 0,428,365) discloses various amino derivatives of FR-900506, FR-900520 and related compounds. A Fujisawa UK patent application (UK Publication No. GB 2,245,891A) discloses various aryl(lower alkyl) and heteroaryl derivatives of FR-900506, FR-900520 and related compounds.

Fujisawa United States patents (U.S. Pat. No. 4,929,611, issued May 29, 1990, U.S. Pat. No. 4,956,352 issued Sep. 11, 1990 and U.S. Pat. No. 5,110,811 issued May 5, 1992) disclose the use of FK-506-type compounds in treating resistance to transplantation. A Sandoz European patent application (EPO Publication No. 0,315,978) discloses the use of FR-900506 and related compounds in the topical treatment of inflammatory and hyperproliferative skin diseases and of cutaneous manifestations of immunologically-mediated illness. A Fisons WIPO patent application (PCT Publication No. WO 91/04025) discloses the use of various derivatives of FR-900506 in the treatment of immunodepression. A Fisons WIPO patent application (PCT Publication WO 90/14826) discloses the use of FR-900506 and related compounds in the treatment of reversible obstructive airways disease, particularly asthma. A Fujisawa European patent application (EPO Publication No. 0,423,714) discloses the use of FK-506 and derivatives as hair revitalizing agents. Various studies have suggested the efficacy of FK-506 in the treatment of a number of ailments, including rheumatoid arthritis (C. Arita, et al., *Clincial exp. Immunol.*, 1990, 82, 456–461; N. Inamura, et al., *Clin. Immunol. Immunopathol.* 1988, 46, 82–90), recent-onset diabetes (N. Murase, et al., *Diabetes*, 1990, 39, 1584–86; N. Murase, et al. *Lancet*, 1990, 336, 373–74), posterior uveitis (H. Kawashima, *Invest. Ophthalmul. Vis. Sci.*, 1988, 29, 1265–71), hepatic injury associated with ischemia (M. Sakr, et al., *Life Sci.*, 1990, 47, 687–91) allergic encephalomyelitis (K, Deguchi, et al., *Brain Nerve*, 1990, 42, 391-97), glomerulonephritis (J. McCauley, et al., *Lancet*, 1990, 335, 674), systemic lupus erythematosus (K. Takabayashi, et al., *Clin. Immunol. Immunopathol.*, 1989, 51, 110-117), multidrug resistance (M. Naito, et al., *Cancer Chemother. Pharmacol.*, 1992, 29, 195-200), inflammation of mucosa and blood vessels (PCT Publication WO 91/17754), cytomegalovirus infection (UK Publication GB 2,247,620A), and idiopathic thrombocytophenic purpura and Basedow's disease (PCT Publication WO 91/19495).

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, type 2 adult onset diabetes, inflammatory bowel disease, biliary cirrhosis, uveitis, multiple sclerosis and other disorders such as Chrons disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was approved by the US FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Never, safer drugs exhibiting less side effects are constantly being searched for in the field.

The 23-membered tricyclo-macrolide immunosuppressant, tacrolimus, FR-900506, FK-506,

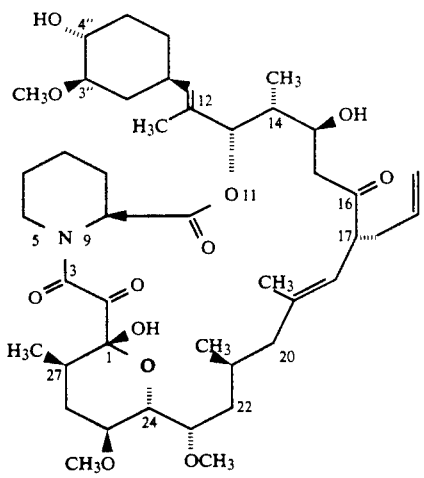

(17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone) and related compounds which were isolated and characterized by Tanaka, Kuroda, and co-workers at Fujisawa Pharmaceutical Co. in Japan, see *J. Am. Chem. Soc.*, 1987, 109, 5031, and U.S. Pat. No. 4,894,366, issued Jan. 16, 1990) have been shown to possess exceptional immunosuppressive activity. Fujisawa United States patents (U.S. Pat. No. 4,929,611, issued May 29, 1990, U.S. Pat. No. 4,956,352, issued Sep. 11, 1990 and U.S. Pat. No. 5,110,811, issued May 5, 1992) disclose the use of FK-506-type compounds in treating resistance to transplantation. In particular, the compound FR-900506 has been reported to be 100 times more effective than cyclosporin in the supression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

The compound FK-506 and related compounds further have been suggested to be useful in the treatment of obstructive airways disease, particularly asthma (PCT Publication WO 90/14826), male pattern alopecia or alopecia senilis (EPO Publication No. 0,423,714), rheumatoid arthitis (C. Arita, et al., *Clinicial exp. Immunol.*, 1990, 82, 456-461; N. Inamura, et al., *Clin. Immunol. Immunopathol.* 1988, 46, 82-90), recent-onset diabetes (N. Murase, et al., *Diabetes*, 1990, 39, 1584-86; N. Murase, et al., *Lancet*, 1990, 336, 373-74), posterior uveitis (H. Kawashima, *Invest. Ophthalmol. Vis. Sci.*, 1988, 29, 1265-71), hepatic injury associated with ischemia (M. Sakr, et al., *Life Sci.*, 1990, 47, 687-91) allergic encephalomyelitis (K, Deguchi, et al., *Brain Nerve*, 1990, 42, 391-97), glomerulonephritis (J. McCauley, et al., *Lancet*, 1990, 335, 674), systemic lupus erythematosus (K. Takabayashi, et al., *Clin. Immunol. Immunopathol.*, 1989, 51, 110-117) multidrug resistance (M. Naito, et al., *Cancer Chemother. Pharmacol.*, 1992, 29, 195-200), inflammation of mucosa and blood vessels (PCT Publication WO 92/17754), cytomegalovirus infection (UK Publication GB 2,247,620A), and idiopathic thrombocytophenic purpura and Basedow's disease (PCT Publication WO 91/19495).

DETAILED DESCRIPTION OF THE INVENTION

A. Scope of the Invention

The novel compound of this invention has structural Formula I:

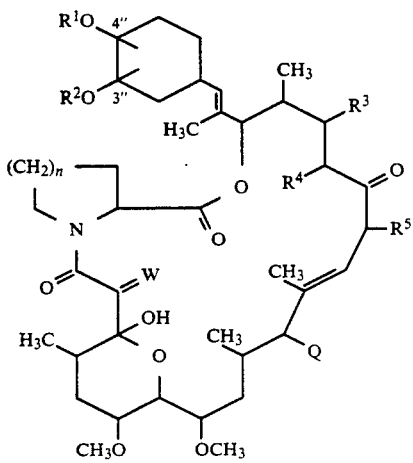

or a pharmaceutically acceptable salt thereof, wherein:

$R^1$ is selected from:

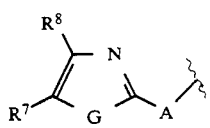

wherein G is N—$R^6$, O, S, SO, or $SO_2$,

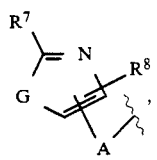

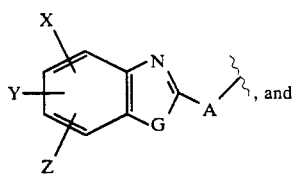

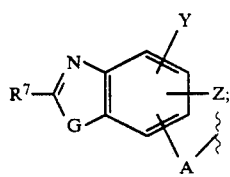

$R^2$ is independently selected from:
(1) the definitions of $R^1$;
(2) hydrogen;
(3) phenyl;
(4) substituted phenyl in which the substituents are X, Y and Z;
(5) 1- or 2-naphthyl;
(6) substituted 1- or 2-naphthyl in which the substituents are X, Y and Z;
(7) biphenyl;
(8) substituted biphenyl in which the substituents are X, Y and Z;
(9) $C_{1-10}$alkyl;
(10) substituted $C_{1-10}$alkyl in which one or more substituent(s) is(are) selected from:
  (a) hydroxy,
  (b) oxo,
  (c) $C_{1-6}$alkoxy,
  (d) phenyl-$C_{1-3}$alkoxy,
  (e) substituted phenyl-$C_{1-3}$alkoxy, in which the substituents on phenyl are X, Y and Z,
  (f) —OCO—$C_{1-6}$alkyl,
  (g) —$NR^9R^{10}$, wherein $R^9$ and $R^{10}$ are independently selected from:
    (i) hydrogen, or
    (ii) $C_{1-6}$alkyl unsubstituted or substituted with one or more of the substituent(s) selected from:
      (a') phenyl, which may be substituted with X, Y and Z,
      (b') —OH,
      (c') $C_{1-6}$alkoxy,
      (d') —$CO_2H$,
      (e') —$CO_2$—$C_{1-6}$alkyl,
      (f') —$C_{3-7}$cycloalkyl, and
      (g') —$OR^{11}$,
    (iii) or where $R^9$ and $R^{10}$ and the N to which they are attached may form an unsubstituted or substituted 3-7-membered heterocyclic ring which may include one or two additional heteroatoms independently selected from the group consisting of O, $S(O)_p$, $NR^{19}$, wherein $R^{19}$ is hydrogen or $C_{1-6}$alkyl unsubstituted or substituted by phenyl, and p is 0, 1 or 2, such as morpholine, thiomorpholine, piperidine, or piperizine,
  (h) —$NR^9CO$—$C_{1-6}$alkyl—$R^{10}$, wherein $R^9$ and $R^{10}$ are as defined above,
  (i) —$COOR^9$, wherein $R^9$ is as defined above,
  (j) —CHO,
  (k) phenyl,
  (l) substituted phenyl in which the substituents are X, Y and Z,
  (m) 1- or 2-naphthyl,
  (n) substituted 1- or 2-naphthyl in which the substituents are X, Y and Z,
  (o) biphenyl,
  (p) substituted biphenyl in which the substituents are X, Y and Z,
  (q) —$OR^{11}$, and
  (r) —$S(O)_p$—$C_{1-6}$alkyl;
(11) $C_{3-10}$alkenyl;
(12) substituted $C_{3-10}$alkenyl in which one or more substituent(s) is(are) selected from:
  (a) hydroxy,
  (b) oxo,
  (c) $C_{1-6}$alkoxy,
  (d) phenyl-$C_{1-3}$alkoxy,
  (e) substituted phenyl-$C_{1-3}$alkoxy, in which the substituents on phenyl are X, Y and Z,
  (f) —OCO—$C_{1-6}$alkyl,
  (g) —$NR^9R^{10}$, wherein $R^9$ and $R^{10}$ are as defined above,
  (h) —$NR^9CO$—$C_{1-6}$alkyl, wherein $R^9$ is as defined above,
  (i) —$COOR^9$, wherein $R^9$ is as defined above,
  (j) —CHO, (k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z;
(q) —$OR^{11}$, and
(r) —$S(O)_p$—$C_{1-6}$alkyl;
(13) $C_{3-10}$alkynyl;
(14) substituted $C_{3-10}$alkynyl in which one or more substituent(s) is(are) selected from:
  (a) hydroxy,
  (b) oxo,
  (c) $C_{1-6}$alkoxy,
  (d) phenyl-$C_{1-3}$alkoxy,
  (e) substituted phenyl-$C_{1-3}$alkoxy, in which the substituents on phenyl are X, Y and Z,
  (f) —OCO—$C_{1-6}$alkyl,
  (g) —$NR^9R^{10}$, wherein $R^9$ and $R^{10}$ are as defined above,
  (h) —$NR^9CO$—$C_{1-6}$alkyl, wherein $R^9$ is as defined above,
  (i) —$COOR^9$, wherein $R^9$ is as defined above,
  (j) —CHO,
  (k) phenyl,
  (l) substituted phenyl in which the substituents are X, Y and Z,
  (m) 1- or 2-naphthyl,
  (n) substituted 1- or 2-naphthyl in which the substituents are X, Y and Z,
  (o) biphenyl,
  (p) substituted biphenyl in which the substituents are X, Y and Z, and
  (q) —$OR^{11}$; and
(15) —$R^{11}$;

$R^3$ is hydrogen, hydroxy, —$OR^{11}$, or $C_{1-6}$alkoxy;
$R^4$ is hydrogen, or $R^3$ and $R^4$ and taken together form a double bond;
$R^5$ is methyl, ethyl, propyl or allyl;
$R^6$ is selected from the group consisting of:
  (1) hydrogen,
  (2) $C_{1-6}$alkyl, unsubstituted or substituted with:
    (a) hydroxy,
    (b) $C_{1-6}$alkoxy,
    (c) —$NR^{12}R^{13}$, wherein $R^{12}$ and $R^{13}$ are independently selected from
      (i) hydrogen,
      (ii) $C_{1-6}$alkyl, or
      (iii) $C_{3-6}$alkenyl,
    (d) phenyl, unsubstituted or substituted with X, Y and Z,
    (e) —$OR^{11}$,
  (3) $C_{3-6}$alkenyl, unsubstituted or substituted with:
    (a) hydroxy,
    (b) phenyl, unsubstituted or substituted with X, Y and Z, or
    (c) $C_{1-6}$alkoxy,
  (4) phenyl, unsubstituted or substituted with X, Y and Z,
  (5) —$R^{11}$,
  (6) X, Y or Z;

$R^7$ and $R^8$ independently are selected from the group consisting of:
  (1) hydrogen,
  (2) $C_{1-7}$alkyl,
  (3) $C_{2-6}$alkenyl,
  (4) —$(CH_2)_m$—$NR^9R^{10}$, wherein $R^9$ and $R^{10}$ are as defined above, and m is 0, 1, 2, or 3,
  (5) —$CF_3$,
  (6) —$CONR^9R^{10}$, wherein $R^9$ and $R^{10}$ are as defined above,
  (7) $R^{14}O(CH_2)_m$— wherein $R^{14}$ is hydrogen, $C_{1-6}$alkyl, hydroxy-$C_{2-3}$alkyl, —$CF_3$, phenyl, $R^{11}$ or naphthyl and m is as defined above,
  (8)
  $$R^{14}O\overset{O}{\underset{\|}{C}}(CH_2)_m-$$
  wherein $R^{14}$ and m are as defined above;
  (9) phenyl—$(CH_2)_m$— wherein m is as defined above and the phenyl is unsubstituted or substituted with X, Y and Z,
  (10) napthyl—$(CH_2)_m$— wherein m is as defined above and the napthyl is unsubstituted or substituted with X, Y and Z,
  (11) biphenyl—$(CH_2)_m$— wherein m is as defined above and the biphenyl is unsubstituted or substituted with X, Y and Z,
  (12) heteroaryl—$(CH_2)_m$— wherein m is as defined above and the heteroaryl is unsubstituted or substituted with X, Y and Z,
  (13) morpholinyl, and
  (14) —CH=CH—phenyl wherein the phenyl is unsubstituted or substituted with X, Y and Z;

$R^{11}$ is selected from:
  (a) —$PO(OH)O^-M^+$, wherein $M^+$ is a positively charged inorganic or organic counterion,
  (b) —$SO_3^-M^{·+}$,
  (c) —$CO(CH_2)_qCO_2^-M^+$, wherein q is 1 to 3, and
  (d) —CO—$C_{1-6}$alkyl—$NR^9R^{10}$, wherein $R^9$ and $R^{10}$ are as defined above and the alkyl is unsubstituted or substituted with one or more substituents selected from:
    (i) hydrogen,
    (ii) $C_{1-6}$alkoxy,
    (iii) —$NR^{12}R^{13}$, wherein $R^{12}$ and $R^{13}$ are as defined above,
    (iv) —$COOR^6$, wherein $R^6$ is as defined above,
    (v) phenyl,
    (iv) substituted phenyl in which the substituents are X, Y and Z,
    (vii) heteroaryl,
    (viii) —SH, and
    (ix) —S—$C_{1-6}$alkyl;

A is selected from the group consisting of:
  (1) a bond,
  (2) $C_{1-10}$alkyl;
  (3) substituted $C_{1-10}$alkyl in which one or more substituent(s) is(are) selected from:
    (a) hydroxy,
    (b) oxo,
    (c) $C_{1-6}$alkoxy,
    (d) phenyl-$C_{1-3}$alkoxy,
    (e) substituted phenyl-$C_{1-3}$alkoxy, in which the substituents on phenyl are X, Y and Z,
    (f) —OCO—$C_{1-6}$alkyl,
    (g) —$NR^9R^{10}$, wherein $R^9$ and $R^{10}$ are as defined above,
    (h) —$NR^9CO$—$C_{1-6}$alkyl, wherein $R^9$ is as defined above,
    (i) —$COOR^9$, wherein $R^9$ is as defined above, (j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z,
(q) —OR$^{11}$, and
(r) —S(O)$_p$—C$_{1-6}$alkyl;

(4) —C$_{1-10}$alkyl wherein one or more of the alkyl carbons is replaced by a group selected from: —NR$^9$—, —O—, —S(O)$_n$—, —CO$_2$—, —O$_2$C—, —CONR$^9$—, —NR$^9$CO—, —NR$^9$CONR$^{10}$—;

(5) —C$_{3-10}$alkenyl wherein alkenyl contains one to four double bonds and wherein one or more of the alkyl carbons is replaced by a group selected from: —NR$^9$—, —O—, —S(O)$_p$—, —CO$_2$—, —O$_2$C—, —CONR$^9$—, —NR$^9$CO—, and —NR$^9$CONR$^{10}$—;

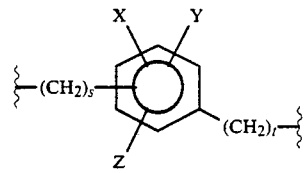
(6)

wherein s is 0 to 6 and t is 0 to 6,

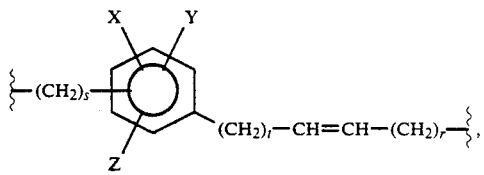
(7)

wherein r is 1 to 3 and s, and t are as defined above;
Q is hydrogen, hydroxy, —OR$^{11}$ or fluoro;
W is O or (H, OH);
X, Y and Z are independently selected from the group consisting of:
(a) hydrogen,
(b) C$_{1-10}$alkyl, unsubstituted or substituted with one or more substituents selected from:
 (i) aryl,
 (ii) substituted aryl in which the substituents are X', Y' and Z',
 (iii) heteroaryl,
 (iv) substituted heteroaryl in which the substituents are X', Y', and Z',
 (v) unsubstituted or substituted aryloxy, in which the substituents on aryl are X', Y' and Z',
 (vi) —OR$^9$,
 (vii) —OR$^{11}$,
 (viii) —OCOR$^9$,
 (ix) —OCO$_2$R$^9$,
 (x) —NR$^9$R$^{10}$,
 (xi) —CHO,
 (xii) —NR$^9$COC$_{1-6}$alkyl—R$^{10}$,
 (xiii) —NR$^9$CO$_2$C$_{1-6}$alkyl—R$^{10}$,
 (xiv) —NR$^9$CONR$^9$R$^{10}$,
 (xv) —OCONR$^9$R$^{10}$,
 (xvi) —CONR$^9$R$^{10}$, (c) C$_{1-10}$alkyl wherein one or more of the alkyl carbons is replaced by a group selected from —NR$^9$—, —O—, —S(O)$_p$—, —CO$_2$—, —O$_2$C—, —CONR$^9$—, —NR$^9$CO—, —NR$^9$CONR$^{10}$—, —CO—, —CH(OH)—, alkenyl or alkynyl and the alkyl may be unsubstituted or substituted with one or more substituents selected from:
 (i) aryl,
 (ii) substituted aryl in which the substituents are X', Y' and Z',
 (iii) heteroaryl,
 (iv) substituted heteroaryl in which the substituents are X', Y', and Z',
 (v) unsubstituted or substituted aryloxy, in which the substituents on aryl are X', Y', and Z',
 (vi) —OR$^9$,
 (vii) —OR$^{11}$,
 (viii) —OCOR$^9$,
 (ix) —OCO$_2$R$^9$,
 (x) —NR$^9$R$^{10}$,
 (xi) —CHO
 (xii) —NR$^9$COC$_{1-6}$alkyl—R$^{10}$,
 (xiii) —NR$^9$CO$_2$C$_{1-9}$alkyl—R$^{10}$,
 (xiv) —NR$^9$CONR$^9$R$^{10}$,
 (xv) —OCONR$^9$R$^{10}$,
 (xvi) —CONR$^9$R$^{10}$,
(d) halogen,
(e) —NR$^9$R$^{10}$,
(f) —CN,
(g) —CHO,
(h) —CF$_3$,
(i) —SR$^{15}$, wherein R$^{15}$ is hydrogen, C$_{1-6}$alkyl, trifluoromethyl, or phenyl,
(j) —SOR$^{15}$,
(k) —SO$_2$R$^{15}$,
(l) —CONR$^9$R$^{10}$,
(m) R$^{16}$O(CH$_2$)$_m$— wherein R$^{16}$ is hydrogen, C$_{1-6}$alkyl, hydroxy-C$_{2-3}$alkyl, —CF$_3$, phenyl, R$^{11}$ or naphthyl and m is 0, 1, 2, or 3,
(n) —CH(OR$^{17}$)(OR$^{18}$), wherein R$^{17}$ and R$^{18}$ are C$_{1-3}$alkyl or taken together form an ethyl or propyl bridge,
(o)

wherein R$^{16}$ and m are as defined above,
(p)

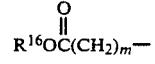

wherein R$^{16}$ and m are as defined above,
(q) —R$^{11}$;
or any two of X, Y and Z may be joined to form a saturated ring having 5, 6 or 7 ring atoms, said ring atoms comprising 1 or 2 oxygen atoms, the remaining ring atoms being carbon, such as dioxolanyl or dioxanyl;
X', Y' and Z' independently are selected from:
(a) hydrogen,
(b) C$_{1-7}$alkyl,
(c) C$_{2-6}$alkenyl,
(d) halogen, (e) —(CH$_2$)$_m$—NR$^9$R$^{10}$, wherein R$^9$, R$^{10}$ and m are as defined above,
(f) —CN,
(g) —CHO,
(h) —CF$_3$,
(i) —SR$^{15}$, wherein R$^{15}$ is as defined above,
(j) —SOR$^{15}$, wherein R$^{15}$ is as defined above,
(k) —SO$_2$R$^{15}$, wherein R$^{15}$ is as defined above,
(l) —CONR$^9$R$^{10}$, wherein R$^9$ and R$^{10}$ are as defined above,
(m) R$^{16}$O(CH$_2$)$_m$— wherein R$^{16}$ and m are as defined above,
(n) —CH(OR$^{17}$)(OR$^{18}$), wherein R$^{17}$ and R$^{18}$ are as defined above,
(o)

wherein R$^{16}$ and m are as defined above,
(p)

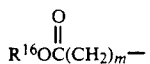

wherein R$^{16}$ and m are as defined above, and
(q) —R$^{11}$;
n is 1 or 2.

The compounds of the present invention have asymmetric centers and this invention includes all of the optical isomers and mixtures thereof.

In addition compounds with carbon-carbon double bonds may occur in Z- and E-forms with all isomeric forms of the compounds being included in the present invention.

When any variable (e.g., alkyl, R$^6$, R$^7$, R$^8$, R$^9$, R$^{11}$, X, Y, Z, etc.) occurs more than one time in any variable or in Formula I, its definition on each occurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec-and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy.

"Alkanoyl" is intended to include those alkylcarbonyl groups of specified number of carbon atoms, which are exemplified by formyl, acetyl, propanoyl and butyryl; "alkanoyloxy" is intended to include those alkylcarbonyl groups of specified number of carbon atoms attached through an oxygen bridge, which are exemplified by formyloxy, acetoxy, propionoyloxy, and butyryloxy. "Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethylpentenyl, and the like, and includes E and Z forms, where applicable; and "arylalkyl" represents aryl groups as herein defined which are attached through a straight or branched chain alkyl group of from one to six carbon atoms, such as, for example, benzyl, phenethyl, 3,3-diphenylpropyl, and the like. "Halogen", as used herein, means fluoro, chloro, bromo and iodo.

The heteroaryl group as used herein includes acridine, carbazole, cinnoline, dibenzofuran, dibenzothiophene, quinoxaline, pyrrazole, indole, imidazole, benzotriazole, furan, benzofuran, quinoline, isoquinoline, pyrazine, pyridazine, pyridine, pyrimidine, pyrrole which are optionally substituted.

In the compounds of Formula I the heteroaryl group may be optionally substituted with X, Y and Z at any available carbon atom or nitrogen atom (if present), but compounds bearing certain of X, Y and Z directly substituted to a nitrogen atom of the heteroaryl ring may be relatively unstable and are not preferred.

The aryl or aromatic group may include phenyl or naphthyl which are optionally substituted by from one- to three-members independently selected from the group consisting of X, Y and Z.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with amines of the formula HNR$^9$R$^{10}$).

In the present invention it is preferred that in compounds of Formula I:
R$^1$ is selected from:

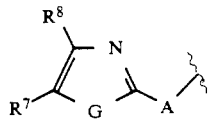

(1)

wherein G is N—R$^6$, O, or S,

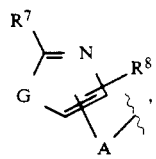

(2)

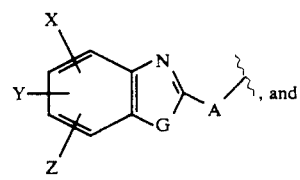

(3)

, and

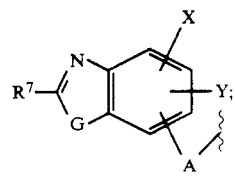

(4)

R$^2$ is independently selected from:
(1) hydrogen;
(2) phenyl;

(3) substituted phenyl in which the substituents are X, Y and Z;
(4) $C_{1-10}$alkyl;
(5) substituted $C_{1-10}$alkyl in which one or more substituent(s) is(are) selected from:
 (a) hydroxy,
 (b) $C_{1-6}$alkoxy,
 (c) phenyl-$C_{1-3}$alkoxy,
 (d) substituted phenyl-$C_{1-3}$alkoxy, in which the substituents on phenyl are X, Y and Z,
 (e) —OCO—$C_{1-6}$alkyl,
 (f) —COOR$^{20}$, wherein R$^{20}$ is hydrogen or $C_{1-6}$alkyl,
 (g) —CHO,
 (h) phenyl, and
 (i) substituted phenyl in which the substituents are X, Y and Z;
(6) $C_{3-10}$alkenyl;
(7) substituted $C_{3-10}$alkenyl in which one or more substituent(s) is(are) selected from:
 (a) hydroxy,
 (b) $C_{1-6}$alkoxy,
 (c) phenyl-$C_{1-3}$alkoxy,
 (d) substituted phenyl-$C_{1-3}$alkoxy, in which the substituents on phenyl are X, Y and Z,
 (e) —OCO—$C_{1-6}$alkyl,
 (f) —COOR$^{20}$, wherein R$^{20}$ is as defined above,
 (g) —CHO,
 (h) phenyl, and
 (i) substituted phenyl in which the substituents are X, Y and Z;
(8) $C_{3-10}$alkynyl;
(9) substituted $C_{3-10}$alkynyl in which one or more substituent(s) is(are) selected from:
 (a) hydroxy,
 (b) $C_{1-6}$alkoxy,
 (c) phenyl-$C_{1-3}$alkoxy,
 (d) substituted phenyl-$C_{1-3}$alkoxy, in which the substituents on phenyl are X, Y and Z,
 (e) —OCO—$C_{1-6}$alkyl,
 (f) —COOR$^{20}$, wherein R$^{20}$ is as defined above,
 (g) —CHO,
 (h) phenyl,
 (i) substituted phenyl in which the substituents are X, Y and Z; and
(10) —R$^{11}$;
R$^3$ is hydrogen or hydroxy;
R$^4$ is hydrogen;
R$^5$ is ethyl, propyl or allyl;
R$^6$ is selected from the group consisting of:
 (1) hydrogen,
 (2) $C_{1-6}$alkyl, unsubstituted or substituted with:
  (a) hydroxy,
  (b) $C_{1-6}$alkoxy,
  (c) phenyl, unsubstituted or substituted with X, Y and Z,
  (d) —OR$^{11}$,
 (3) $C_{3-6}$alkenyl, unsubstituted or substituted with:
  (a) hydroxy,
  (b) phenyl, unsubstituted or substituted with X, Y and Z, or
  (c) $C_{1-6}$alkoxy, and
 (4) phenyl, unsubstituted or substituted with X, Y and Z,
 (5) —R$^{11}$,
 (6) X, Y or Z;
R$^7$ and R$^8$ independently are selected from the group consisting of:

(1) hydrogen,
(2) $C_{1-7}$alkyl,
(3) $C_{2-6}$alkenyl,
(4) —CF$_3$,
(5) R$^{14}$O(CH$_2$)$_m$— wherein R$^{14}$ is hydrogen, $C_{1-6}$alkyl, hydroxy-$C_{2-3}$alkyl, —CF$_3$, phenyl, R$^{11}$ or naphthyl and m is 0, 1, 2 or 3,
(6)

wherein R$^{14}$ and m are as defined above;
(7) phenyl—(CH$_2$)$_m$— wherein m is as defined above and the phenyl is unsubstituted or substituted with X, Y and Z,
(8) heteroaryl—(CH$_2$)$_m$— wherein m is as defined above and the heteroaryl is unsubstituted or substituted with X, Y and Z,
(9) —CH=CH—phenyl wherein the phenyl is unsubstituted or substituted with X, Y and Z;
R$^{11}$ is selected from:
 (a) —PO(OH)O$^-$M$^+$, wherein M$^+$ is a positively charged inorganic or organic counterion,
 (b) —SO$_3^-$M$^+$,
 (c) —CO(CH$_2$)$_q$CO$_2^-$M$^+$, wherein q is 1 to 3, and
 (d) —CO—$C_{1-6}$alkyl—NR$^{20}$R$^{21}$, wherein R$^{20}$ is as defined above and R$^{21}$ is selected from the definitions of R$^{20}$;
A is selected from the group consisting of:
(1) a bond,
(2) $C_{1-10}$alkyl, and

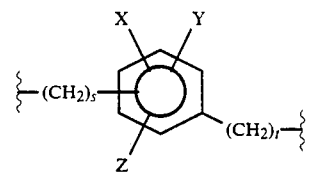
(3)

wherein s is 0 to 2 and t is 0 to 2;
Q is hydrogen, hydroxy, or fluoro;
W is O or (H, OH);
X, Y and Z are independently selected from the group consisting of:
 (a) hydrogen,
 (b) $C_{1-7}$alkyl,
 (c) $C_{2-6}$alkenyl,
 (d) halogen,
 (e) —(CH$_2$)$_m$—NR$^{20}$R$^{21}$, wherein R$^{20}$, R$^{21}$ and m are as defined above,
 (f) —(CH$_2$)$_m$—CONR$^{20}$R$^{21}$, wherein R$^{20}$, R$^{21}$ and m are as defined above,
 (g) —(CH$_2$)$_m$—NR$^{20}$—COR$^{14}$, wherein R$^{14}$, R$^{20}$ and m are as defined above,
 (h) —O—(CH$_2$)$_m$—CONR$^{20}$R$^{21}$, wherein R$^{20}$, R$^{21}$ and m are as defined above,
 (i) —CN,
 (j) —CHO,
 (k) —CF$_3$,
 (l) R$^{14}$O(CH$_2$)$_m$— wherein R$^{14}$ and m is as defined above,
 (m) —R$^{11}$;
and
n is 1 or 2.

In the present invention it is even more preferred that in compounds of Formula I:
R¹ is

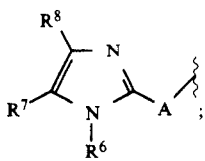

R² is hydrogen or methyl;
R³ is hydrogen or hydroxy;
R⁴ is hydrogen;
R⁵ is ethyl, propyl or allyl;
R⁶ is hydrogen, methyl, benzyl, 3-fluorobenzyl, R¹¹ or —C₁₋₄alkyl—OR¹¹;
R⁷ and R⁸ are independently selected from: hydrogen, methyl, CH₃OCH₂—, HOCH₂—, phenyl, 3,5-difluorophenyl, 3-fluorophenyl, 3,4-difluorophenyl, 3,5-dichlorophenyl, 3-methoxyphenyl, 3-trifluoromethylphenyl, 3-hydroxyphenyl, 4-hydroxyphenyl, 3,5-dihydroxyphenyl, 4-tert-butylphenyl, 3,4-methylenedioxyphenyl, 3,5-trifluoromethylphenyl, 4-methoxyphenyl, 3,5-dimethoxyphenyl, 3-trifluoromethoxyphenyl, 3,5-di(trifluoromethoxy)phenyl, 2-methoxyphenyl, 3-isopropyloxyphenyl, 3-ethoxyphenyl, 3,5-diethoxyphenyl, 3,4,5-trimethoxyphenyl, 3-hydroxyethyloxyphenyl, 3-propyloxyphenyl, 3-isobutyloxyphenyl, 3-methylphenyl, 3,5-dimethylphenyl, 3-ethylphenyl, 3,5-diethylphenyl, and phenylethyl;
A is —CH₂—, phenyl, or benzyl;
Q is hydrogen or fluoro;
W is O or (H, OH);
n is 1 or 2;
and pharmaceutically acceptable salts thereof.

Preferred compounds of the present invention are the compounds identified as follows:

17-ethyl-1,14-dihydroxy-12-[2'-(4''-(2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'--(4''-(3-''''(2'''-imidazolyl)-propyloxy)-3''-methoxycyclohexyl)-1'-methylvinyl]23,25-dimethoxy-13,19,21,27-tetramethyl-11,28-dioxa-4-azatricyclo[22.3.1.0⁴,⁹]octacos-18-ene-2,3-10,16-tetraone;

17-ethyl-1,14-dihydroxy-12-[2'-(4''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''--(4'''-methyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(4'''-methyl-5'''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-ethyl-1,14-dihydroxy-12-[2'-(4''-(4'''-methoxymethyl-5'''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-(4'''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-hydroxy-3''-(4'''-phenyl-2'''-imidazolylmethyloxy)-cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(1'''-methyl-4'''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''--(1'''-benzyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(4'''-(3'''',5''''-bistrifluoromethoxyphenyl)-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(1'''-m--fluorobenzyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(m-2'''-imidazolylbenzyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(para-2'''-imidazolylbenzyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(ortho-2'''-imidazolylbenzyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(meta-1'''-methyl-2'''-imidazolylbenzyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-4'''-meta-difluorophenyl-2'''-imidazolylmethoxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''(4''',4''',6''',7'''-tetrahydro-2'''-benzimidazolylmethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(-4''-(3'''-(2''''-imidazolyl)-phenyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone 17-ethyl-1-hydroxy-12-[2'-(4"-(4"'-p-tert--butylphenyl-(2"'-imidazolylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"(4"'-m--hydroxyphenyl-2"'-imidazolylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-m-trifluoromethylphenyl-2"'-imidazolylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-(3"",5""-dichlorophenyl)-2"'-imidazolylmethyloxy)-3"-methoxycyclohexyl)-1'-methylvinyl]-23,25-dimethoxy-13,19,21,-27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-(3"",4""-difluorophenyl)-2"'-imidazolylmethyloxy)-3"-methoxycyclohexyl)-1'-methylvinyl]-23,25-dimethoxy-13,19,21,-27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-metamethoxyphenyl-2"'-imidazolylmethyloxy)-3"-methoxycyclohexyl)-1'-methylvinyl]-23,25-dimethoxy-13,19,21,-27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-metamethoxyphenyl-2"'-imidazolylmethyloxy)-3"-methoxycyclohexyl)-1'-methylvinyl]-23,25-dimethoxy-13,19,21,-27-tetramethyl-11,28-dioxa-4-azatricyclo[22.3.1.0⁴,⁹]octacos-18-ene-2,3,10,16-tetraone, hydrochloride;

17-ethyl-1,14-dihydroxy-12-[2'-(4"-(4"'-metathiomethylphenyl-2"'-imidazolylmethyloxy)-3"-methoxycyclohexyl)-1'-methylvinyl]-23,25-dimethoxy-13,19,21,-27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-(3"",-4""-methylenedioxyphenyl)-2"'-imidazolylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-metafluorophenyl-2"'-imidazolylmethyloxy)-3"-methoxycyclohexyl)-1'-methylvinyl]-23,25-dimethoxy-13,19,-21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-(3"",-5""-bis(trifluoromethyl)phenyl)-2"'-imidazolylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-para-methoxyphenyl-2"'-imidazolylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-(3"",5""-dimethoxyphenyl)-2"'-imidazolylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-meta-trifluoromethoxyphenyl-2"'-imidazolylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-orthomethoxyphenyl-2"'-imidazolylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-metaisopropoxyphenyl-2"'-imidazolylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-metaethoxyphenyl-2"'-imidazolylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-(3"",4"",5""-trimethoxyphenyl)-2"'-imidazolylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-(3"",5""-dithiomethylphenyl)-2"'-imidazolyl-methyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-meta(hydroxyethyloxy)phenyl)-2"'-imidazolylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-metapropoxyphenyl-2"'-imidazolylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-metaisobutyloxyphenyl-2"'-imidazolylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-meta--methylphenyl-2"'-imidazolylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-ethyl-1,14-dihydroxy-12-[2'-(4"-(4"'-(3""-(2'"-imidazolyl)-propyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4"'-hydroxymethyl-5"'-phenyl-2"'-imidazolylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(meta-(4"'-(3""-hydroxyphenyl)-2"'-imidazolyl)benzyloxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(meta--(4"'-phenyl-2"'-imidazolyl)benzyloxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(4'''-meta-d-imethylphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(4'''-met-a-ethylphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-ethyl-1,14-dihydroxy-12-[2'-(4''-(4'''-p-henethylphenyl-2'''-imidazolymethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone; or a pharmaceutically acceptable salt thereof.

B. Preparation of Compounds Within the Scope of the Present Invention

The starting materials for the preparation of the compounds of this invention are represented by Formula II:

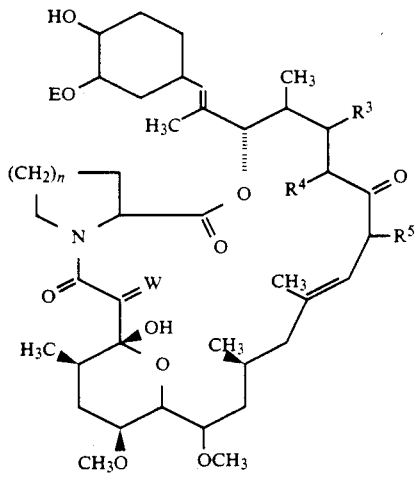

wherein:
E is hydrogen or methyl;
W is O or (H, OH);
R³ is hydrogen, hydroxy, C₁₋₆ acyloxy, or C₁₋₆ alkoxy;
R⁴ is hydrogen, or R³ and R⁴ taken together form a double bond;
R⁵ is methyl, ethyl, propyl or allyl; and
n is 1 or 2.

The production and characterization of compounds of Formula II is well known in the literature (see U.S. Pat. No. 4,894,366 issued Jan. 16, 1990; U.S. Pat. No. 4,929,611 issued May 29, 1990; U.S. Pat. No. 3,244,592 issued Apr. 15, 1966; EPO Publication No. 0,323,042,; EPO Publication 0,356,399; PBJ Disclosure 63-17884; *J. Am. Chem. Soc.*, 1987, 109, 5031; *J. Antibiotics*, 1987, 40, 1249 *J. Antibiotics*, 1988, 41 (11), 1592; and *J. Antibiotics*, 1992, 45 (1), 118). Both biological fermentation and synthetic processes may be found. A synthetic route to compounds of Formula II can involve modifications of a route described in *J. Am. Chem. Soc.*, 1989, 111, 1157.

Biological fermentation followed by synthetic modification is presently favored in the art as the method to produce compounds of Formula II. Organisms belonging to the genus Streptomyces such as *Streptomyces tsukubaensis*, No. 9993 and *Streptomyces hygroscopicus*, var. ascomycetis, No. 14891 placed in an aqueous nutrient medium will produce desired compounds in isolable amounts. The nutrient medium contains sources of assimilable carbon and nitrogen, preferably under aerobic conditions. Produced in fermentation are four compounds of Formula II, (A) where E is methyl, W is O, R³ is hydroxyl, R⁴ is hydrogen R⁵ is allyl and n is 2; (B) where E is methyl, W is O, R³ is hydroxyl, R⁴ is hydrogen, R⁵ is ethyl and n is 2; (C) where E is methyl, W is O, R³ is hydroxyl, R⁴ is hydrogen, R⁵ is methyl and n is 2; and (D) where E is methyl W is O, R³ is hydroxyl, R⁴ is hydrogen, R⁵ is allyl and n is 1.

A lyophilized sample of the isolated *Streptomyces tsukubaensis*, No. 9993 was deposited with the Fermentation Research Institute, Agency of Industrial Science and Technology (No. 1-3, Higashi 1-chome, Yatabemachi Tsukuba-gun, Ibaraki Prefecture, Japan) under the deposit number of FERM P-7886 (deposit date: Oct. 5, 1984), and then converted to Budapest Treaty route of the same depository on Oct. 19, 1985 under the new deposit number of FERM BP-927.

Compounds A, B, C and D of Formula II, organisms to produce the same, conditions of fermentation, separation techniques, and chemical modification of the products are fully described in U.S. Pat. No. 4,894,366, issued Jan. 16, 1990 and U.S. Pat. No. 4,929,611, issued May 29, 1990.

Using the four compounds produced in fermentation above, the remaining compounds of Formula II may be easily produced. The allyl of R⁵ may be conveniently reduced to propyl by well known methods, for example as described in U.S. Pat. No. 4,894,366. The hydroxy of R³ may be protected by well known methods, for example as disclosed in EPO Publication No. 0,323,042. Likewise, the hydroxyl at C-4'' may also be protected. In addition, the hydroxy of R³ may be reduced to a hydrogen or eliminated to form a double bond with R⁴ (by methods disclosed in U.S. Pat. No. 4,894,366, EPO Publication No. 0,323,042 or EPO Publication No. 0,413,532). The carbonyl of W may be reduced to the alcohol by methods disclosed in EPO Publication No. 0,323,042 or by methods disclosed in EPO Publication No. 0,445,975.

The methyl of E as produced may be replaced with hydrogen or demethylated and subsequently protected as desired, if necessary. This demethylation of compounds wherein E is methyl may be carried out in a fermentation reaction using the compounds of Formula II as a feedstock. For instance, compound A named under Formula II above may be demethylated at E above by using the microorganism Actinomycetales ATCC No. 53771 (described in U.S. Pat. No. 4,981,792) or produced directly by using the microorganism *Streptomyces tsukubaensis*, No. 9993 (described in EPO Publication No. 0,353,678). Similarly, compound B named under Formula II above may be demethylated at E above using the microorganism Actinoplanacete sp. ATCC No. 53771 (described in EPO Publication No. 0,349,061). In addition the compound of Formula II wherein E is H, W is O, R³ is hydroxy, R⁴ is ethyl and n is 2 may be produced directly by fermentation using the mutant microorganism *Streptomyces hygroscopicus* sup. ascomyceticus, No. 53855 (being a blocked mutant of *Streptomyces hygroscopicus* sup. ascomyceticus, No. 14891) (as described in EPO Publication No. 0,388,152). Similarly, the compound of Formula II wherein E is hydrogen, W is O, R³ is hydroxy, R⁴ is hydrogen R⁵ is methyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (as described in EPO Publication No. 0,388,153). The hydroxy of C-3" may be protected by methods similar to those known for the protection of the hydroxyl groups of $R^3$ and/or C-4", for example as disclosed in U.S. Pat. No. 4,894,366.

Suitable protecting groups for hydroxyl include those groups well known in the art which are:

1-(lower alkylthio)(lower)alkyl, wherein "lower alkyl" indicates a straight, cyclic or branched chain of one to six carbon atoms, such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like, in which the preferred one may be $C_1$–$C_4$ alkylthiomethyl and the most preferred one may be methylthiomethyl; trisubstituted silyl such as tri(lower)alkylsilyl (e.g. trimethylsilyl, triethylsilyl, tributysilyl, tri-i-propylsilyl, t-butyldimethylsilyl, tri-t-butylsilyl, etc.), lower alkyldiarylsilyl (e.g. methyl-diphenylsilyl, ethyl-diphenylsilyl, propyl-diphenylsilyl, t-butyldiphenylsilyl, etc.), and the like, in which the preferred one may be tri($C_1$–$C_4$)alkylsilyl and $C_1$–$C_4$ alkyl-diphenylsilyl, and the most preferred one may be tert-butyl-dimethylsilyl, tri-i-propylsilyl and tert-butyl-diphenylsilyl; acyl such as aliphatic acyl, aromatic acyl and aliphatic acyl substituted with aromatic group, which are derived from carboxylic acids; and the like.

Compounds A, B, C and D of Formula II, organisms to produce the same, conditions of fermentation, separation techniques, and chemical modification of the products are fully described in U.S. Pat. No. 4,894,366, dated Jan. 16, 1990, U.S. Pat. No. 4,929,611, issued May 29, 1990 and U.S. Pat. No. 5,110,811, issued May 5, 1992.

The novel processes for preparing the novel compounds of the present invention are illustrated as follows, wherein $R^1$, $R^2$, $R^3$, $R^4$, $R^5$, A, Q, W, n, p and q are as defined above unless otherwise indicated. It will be readily apparent to one of ordinary skill in the art reviewing the synthetic route depicted below that other compounds within Formula I can be synthesized by substitution of appropriate reactants and agents in the synthesis shown below.

REACTION SCHEME A

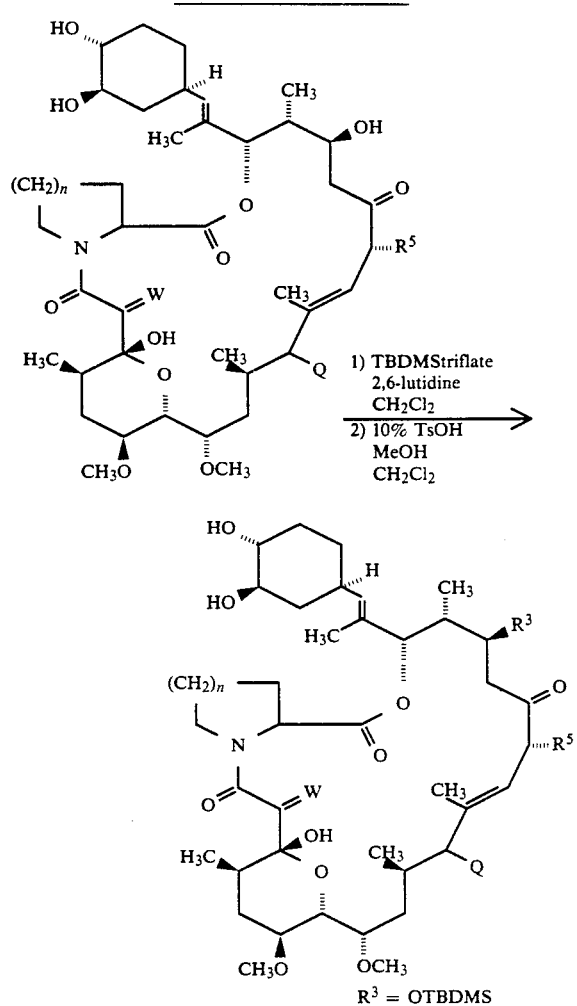

REACTION SCHEME B

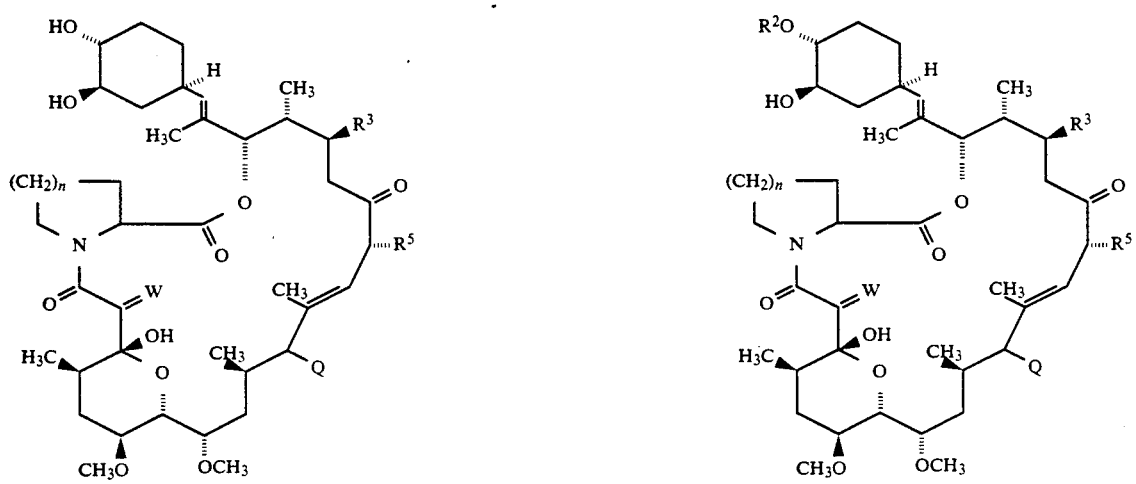

-continued
REACTION SCHEME B
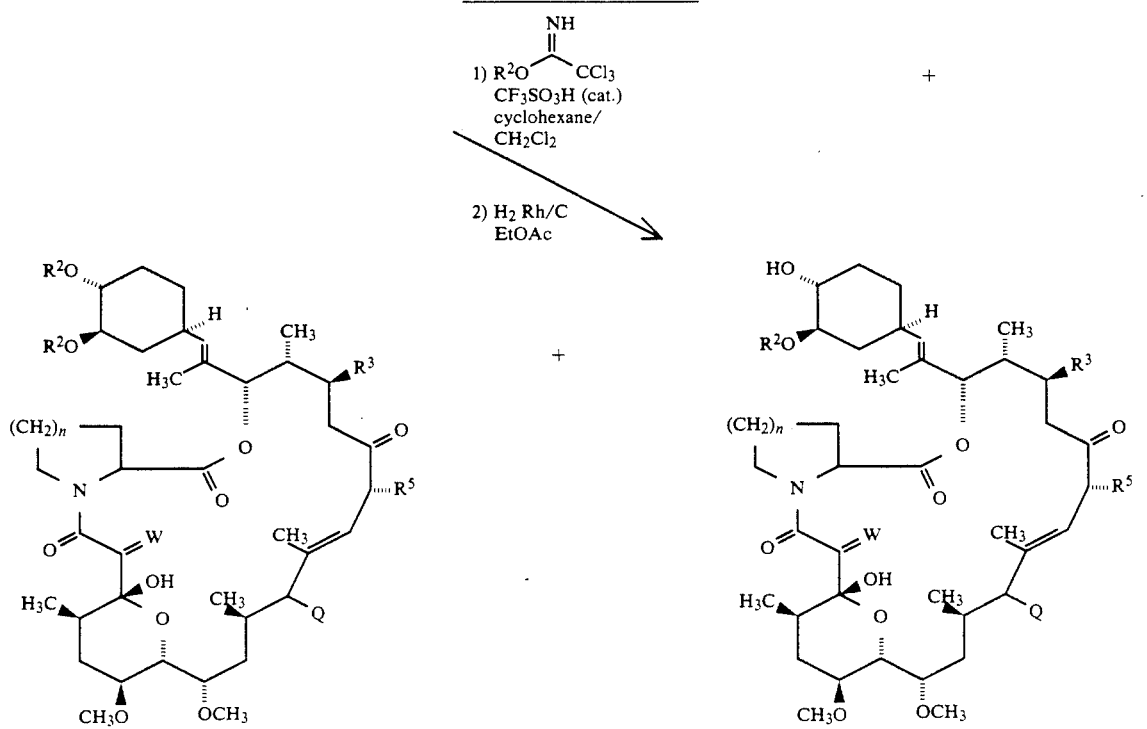
REACTION SCHEME C
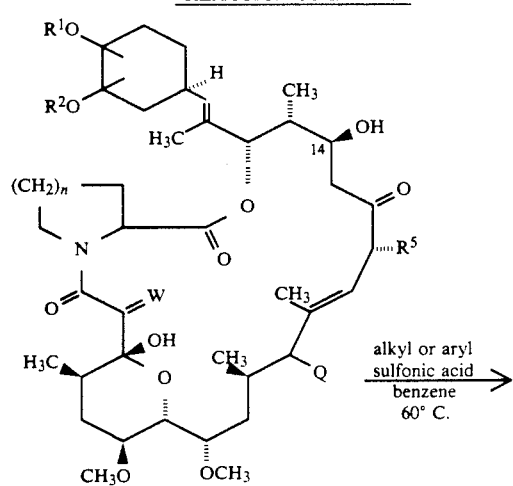
-continued
REACTION SCHEME C
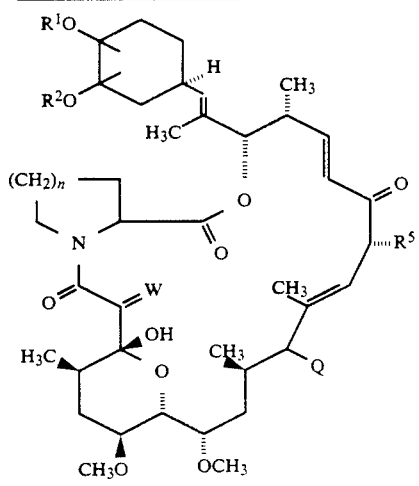

25
REACTION SCHEME D
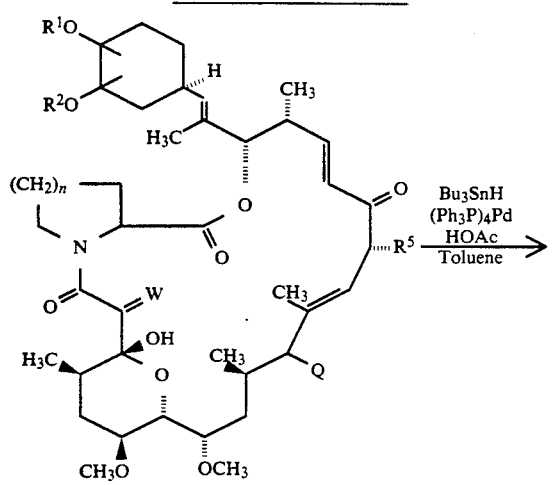
26
-continued
REACTION SCHEME D
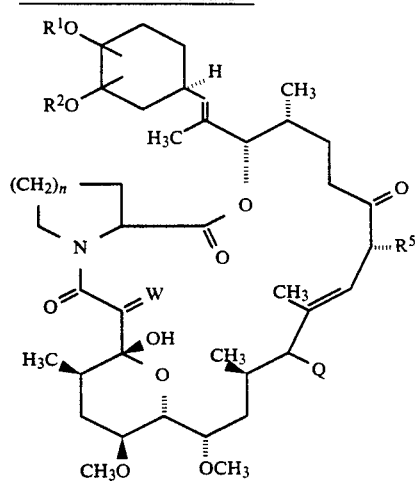
REACTION SCHEME E
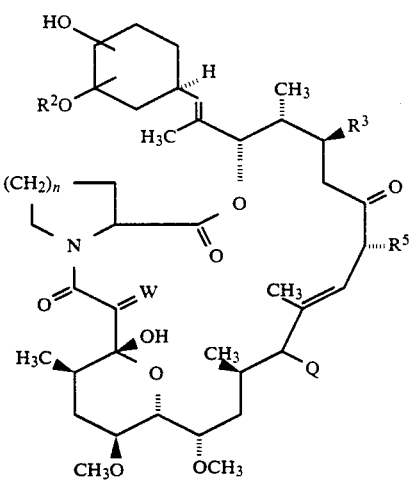

REACTION SCHEME E
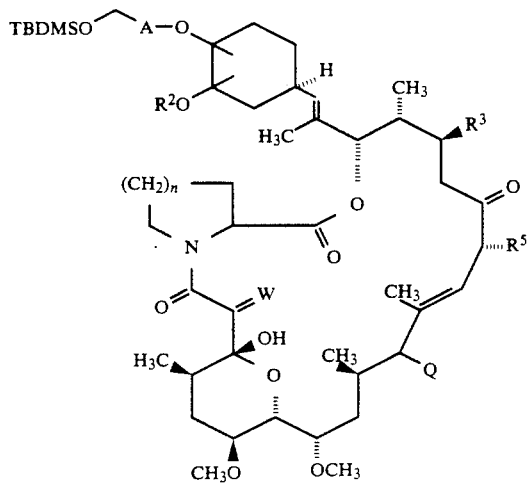
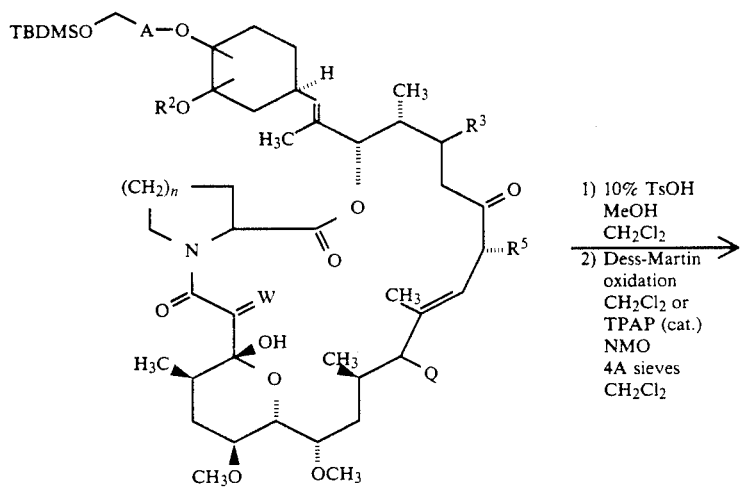
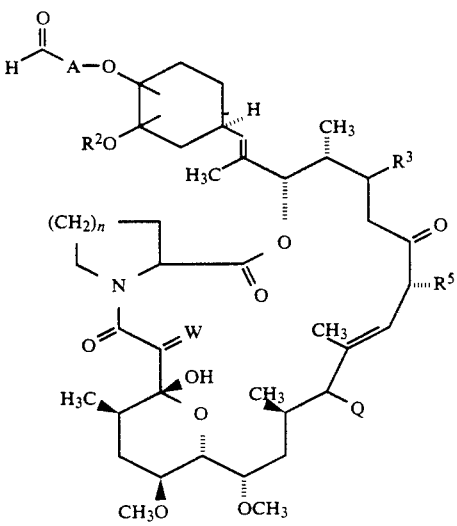

REACTION SCHEME F
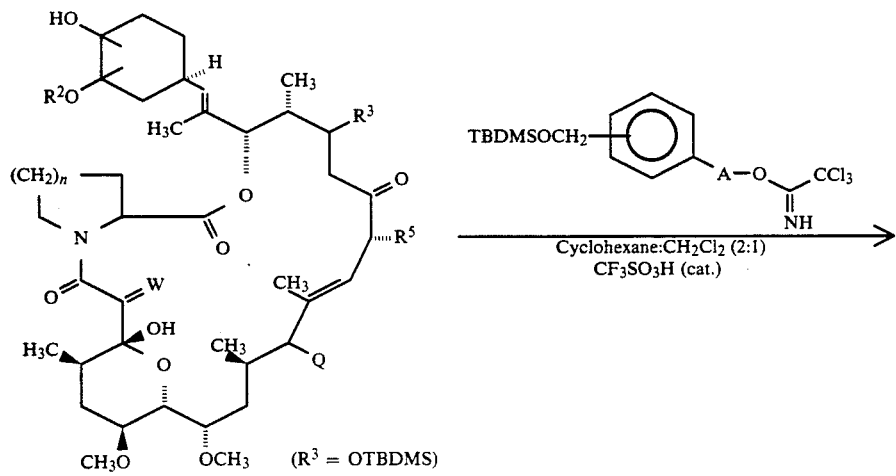
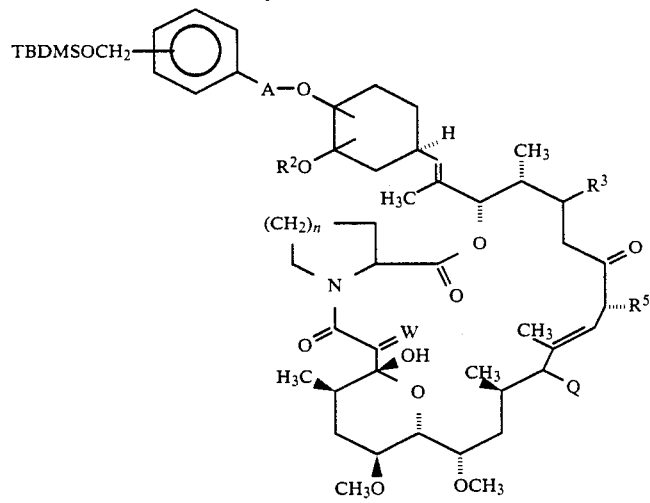
REACTION SCHEME G
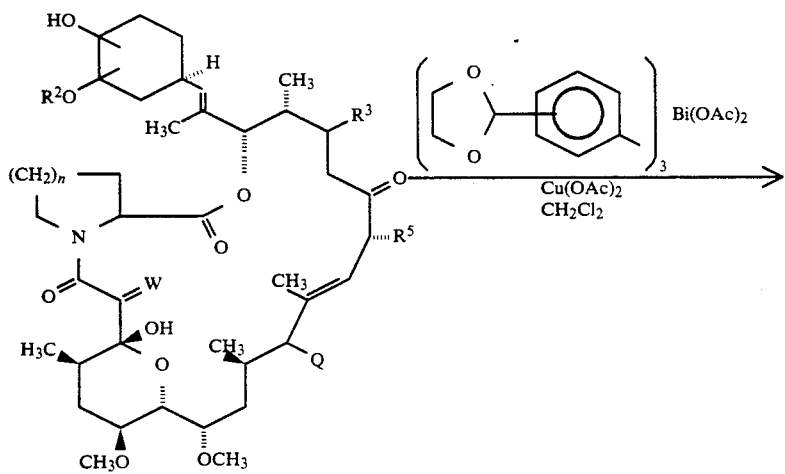

5,247,076
31
-continued
REACTION SCHEME G
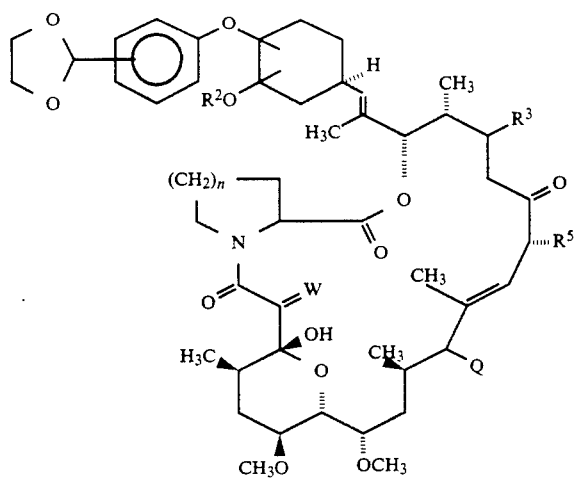
REACTION SCHEME H
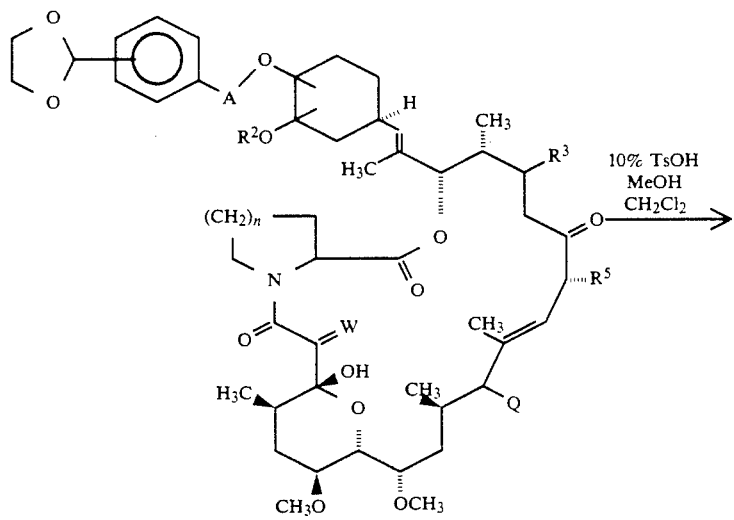
10% TsOH
MeOH
CH$_2$Cl$_2$
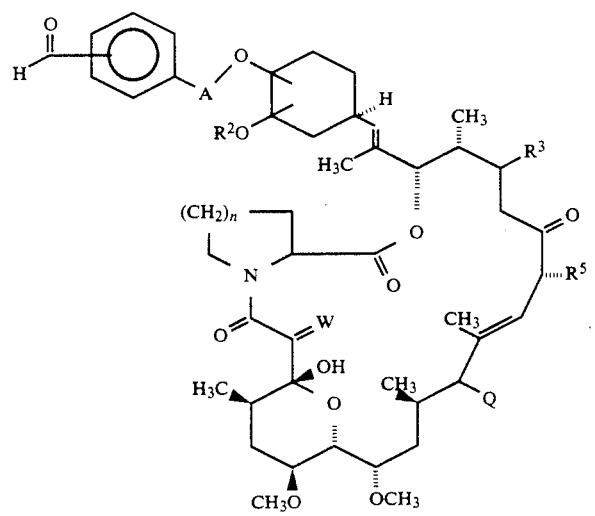

REACTION SCHEME I
REACTION SCHEME J
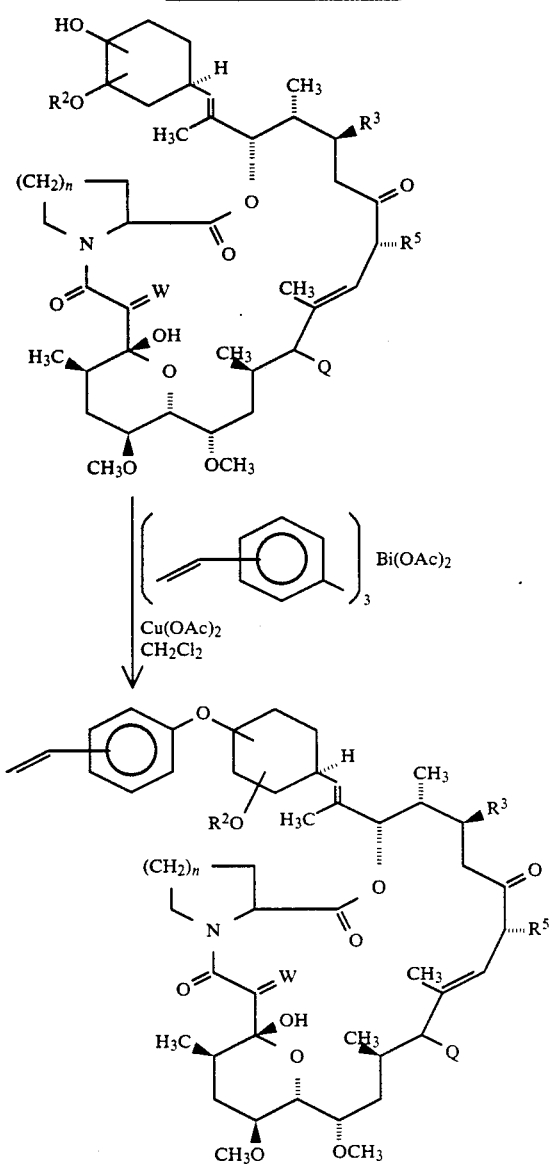
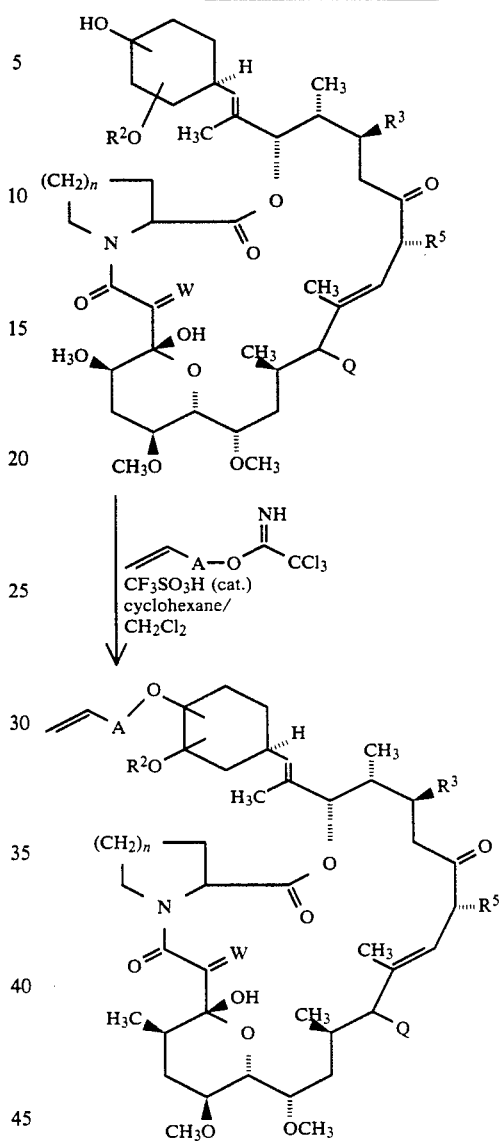
REACTION SCHEME K
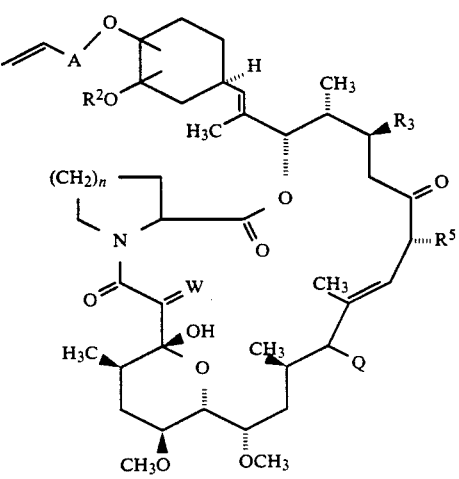

-continued
REACTION SCHEME K
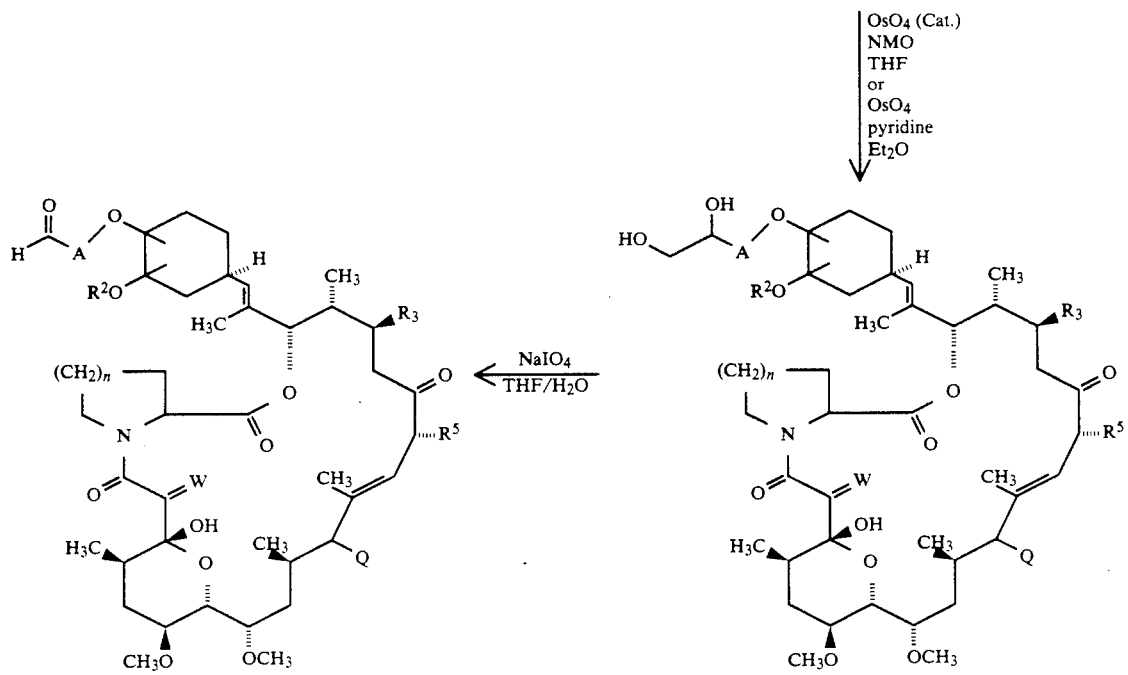
REACTION SCHEME L
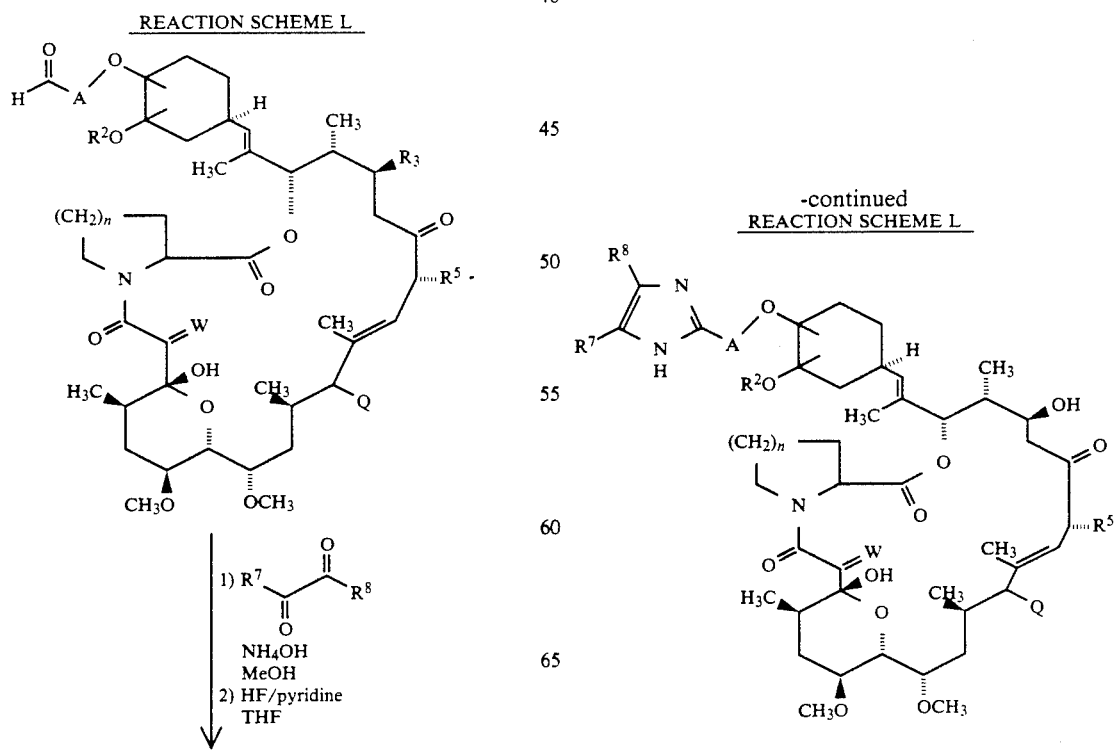

37
REACTION SCHEME M
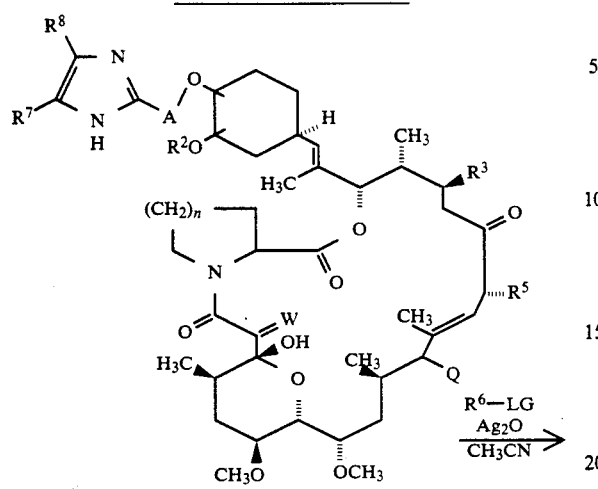
38
-continued
REACTION SCHEME M
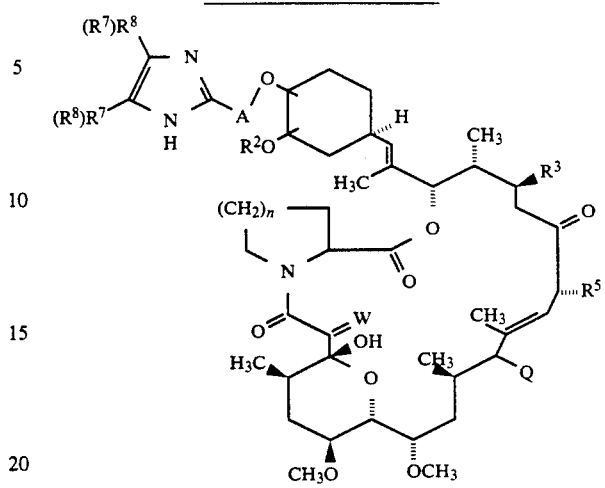
REACTION SCHEME N
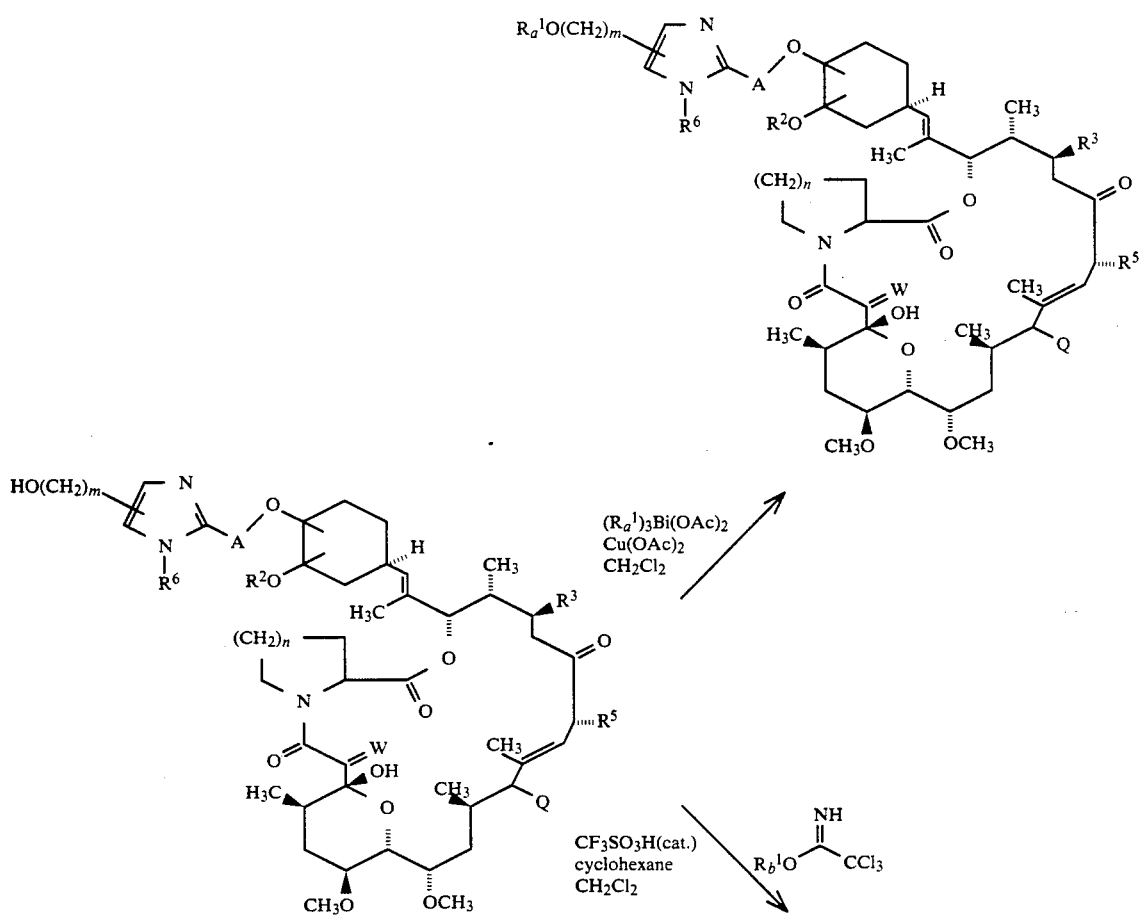

-continued
REACTION SCHEME N
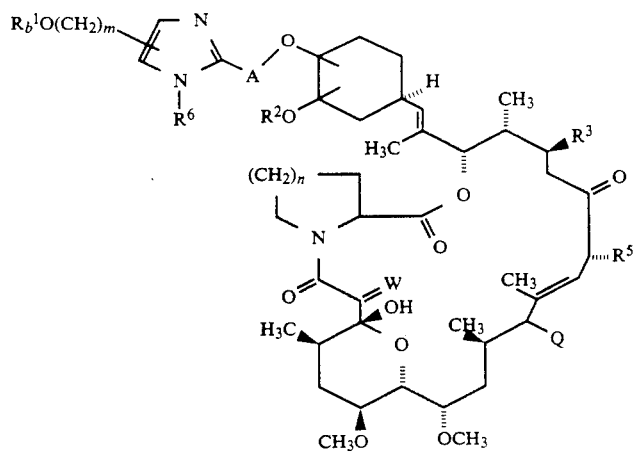
REACTION SCHEME O
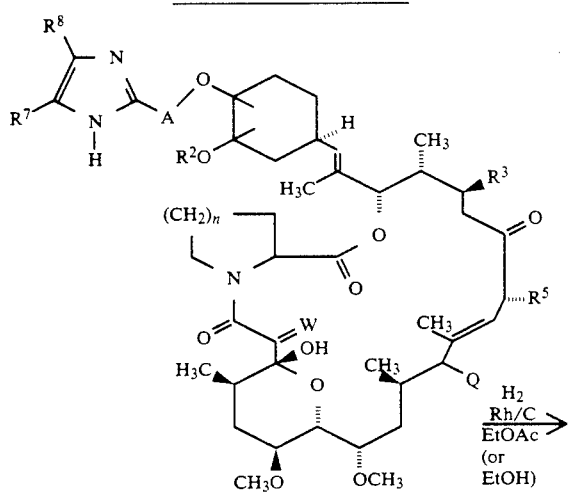
REACTION SCHEME P
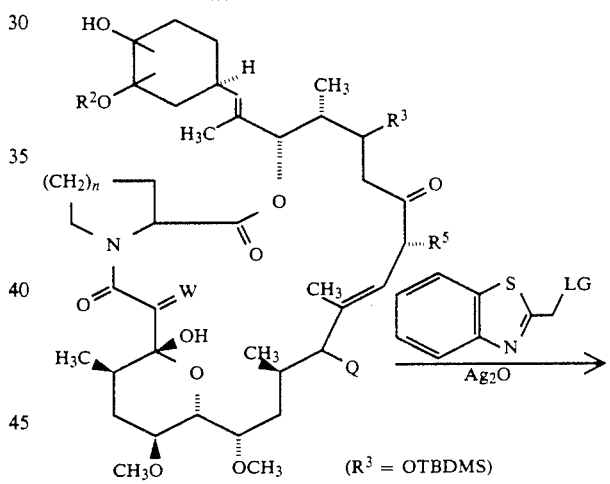
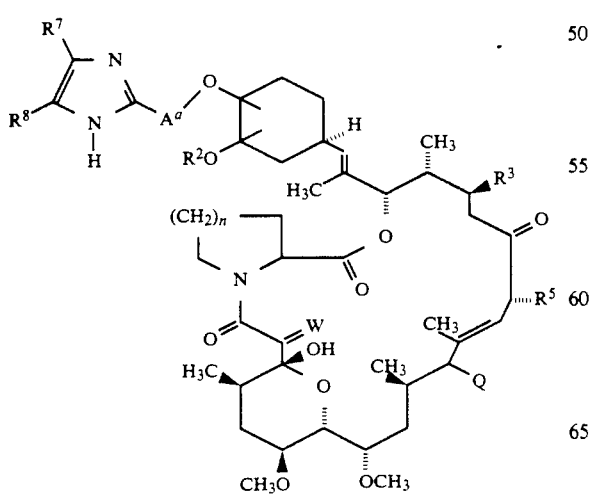
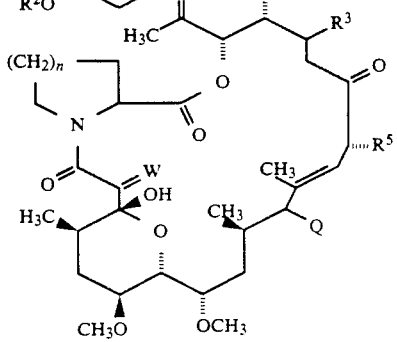

41
REACTION SCHEME Q
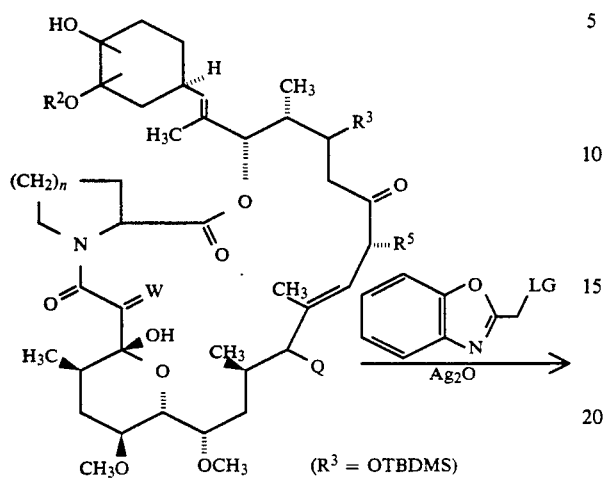
(R³ = OTBDMS)
REACTION SCHEME R
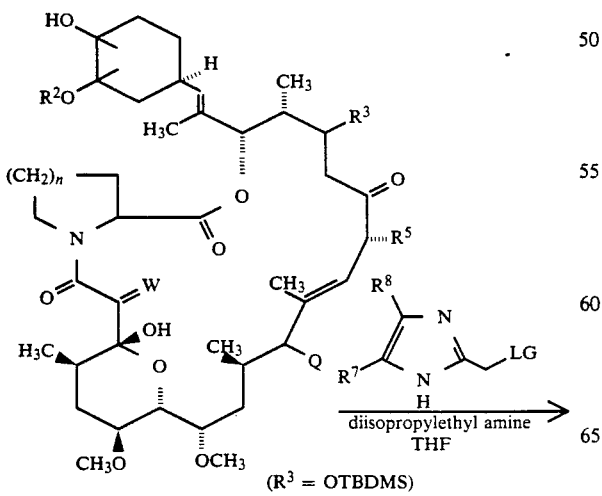
(R³ = OTBDMS)
42
-continued
REACTION SCHEME R
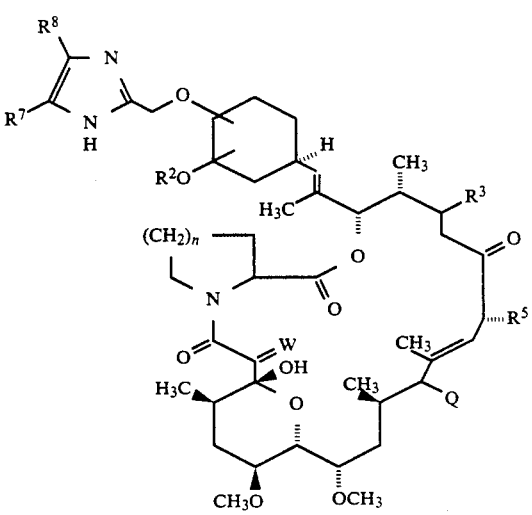
REACTION SCHEME S
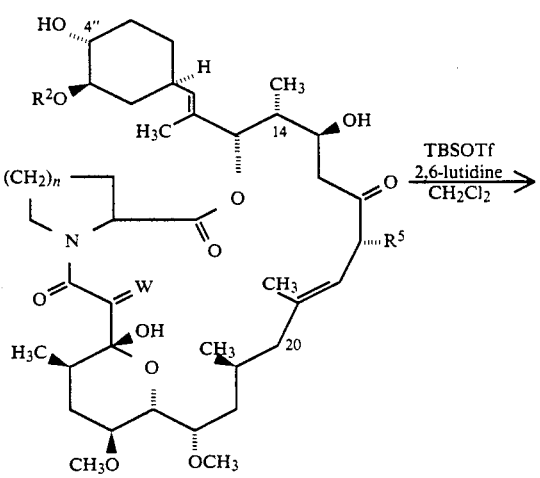
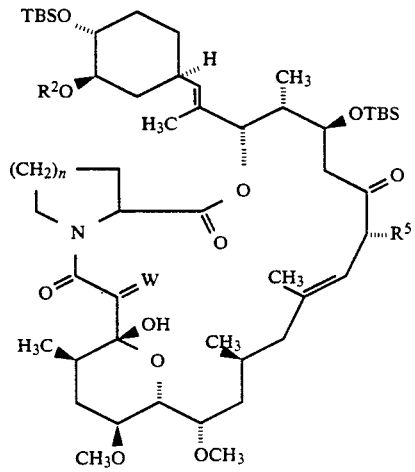

-continued
REACTION SCHEME S

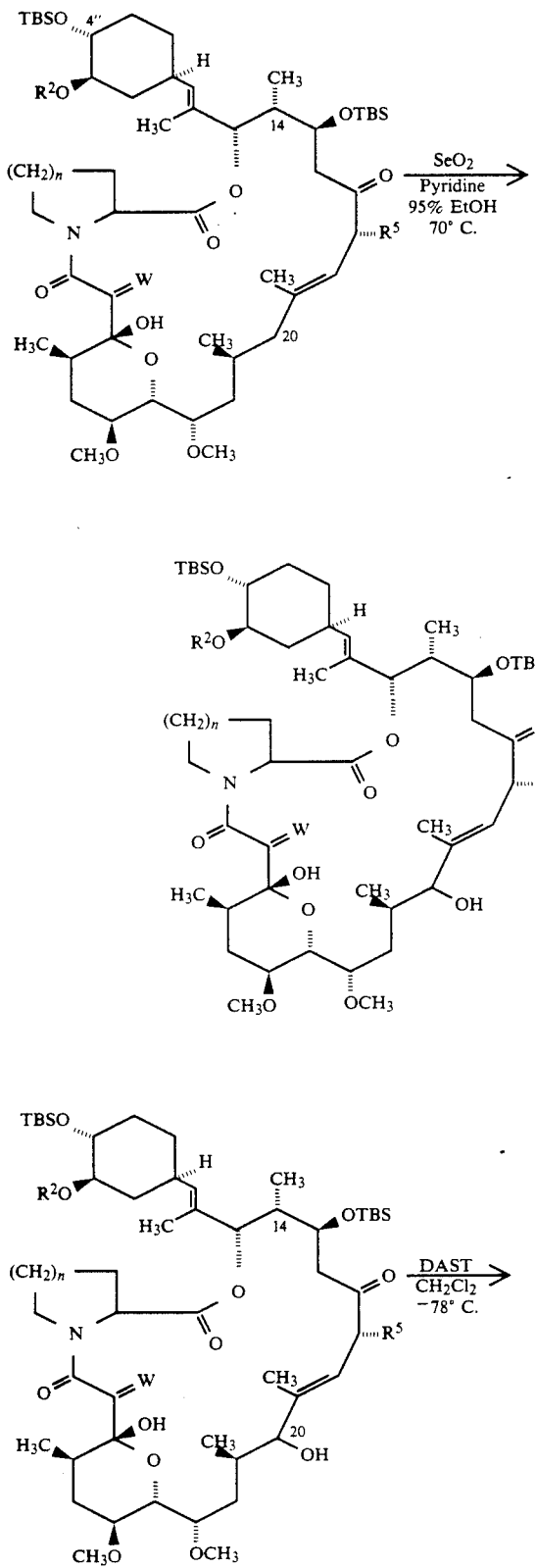

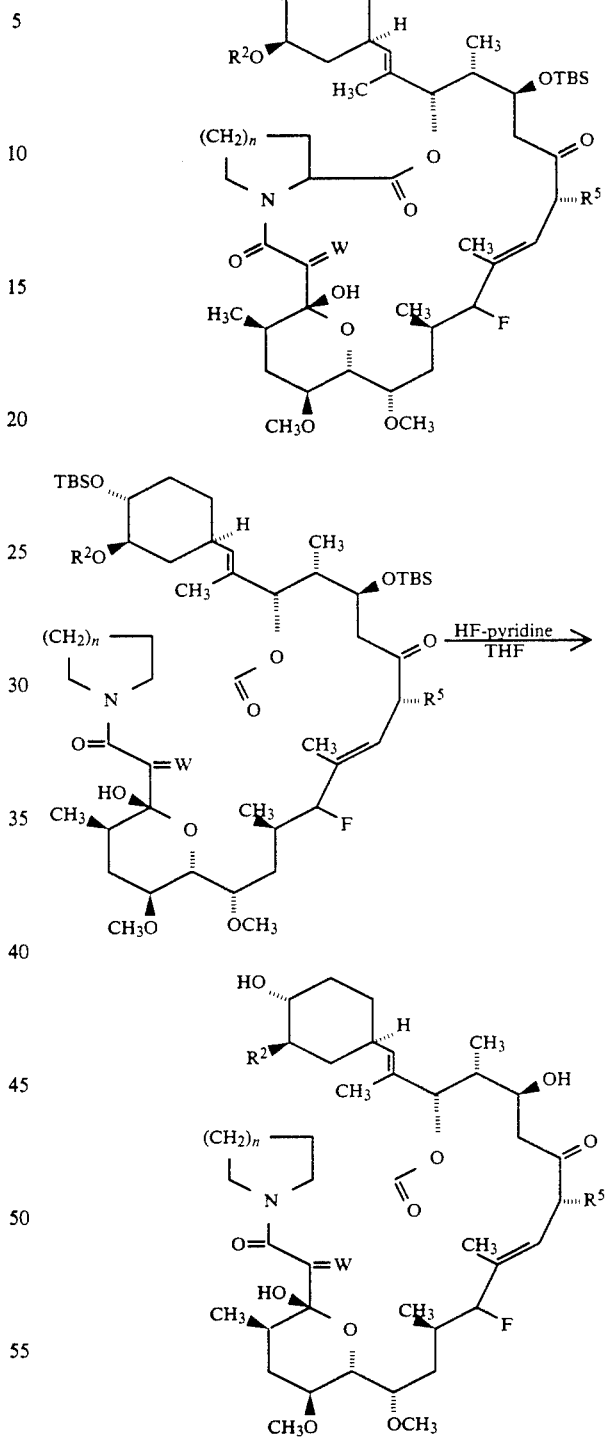

Protection of the C-3", C-4" and/or the C-14 hydroxyl group may be accomplished by methods known in the prior art for compounds of Formula II such as by treatment with: 2,6-lutidine and triisopropylsilyl trifluoromethanesulfonate in a solution of methylene chloride; 2,6-lutidine and t-butyldimethylsilyl trifluoromethanesulfonate in a solution of methylene chloride; pyridine and acetic anhydride in a solution of methylene chloride; pyridine and benzoyl chloride in a solution of methylene chloride; pyridine and p-nitrobenzoyl chloride in a solution of methylene chloride; imidazole and t-butyldiphenylsilyl chloride in a solution of methylene chloride; and the like. For example, as shown in Reaction Scheme A, the C-4", 14-dihydroxy C-3"-methoxy macrolide may be protected at C-14 as the t-butyldimethylsilyl ether by treatment with t-butyldimethylsilyl trifluoromethanesulfonate in methylene chloride to give the C-4", 14-di-O-TBDMS macrolide. Treatment with toluenesulfonic acid in a mixture of methanol and methylene chloride results in selective removal of the C-4" silyl ether to give the C-14-O-TBDMS macrolide.

As shown in Reaction Scheme B, a solution of the 3",4"-dihydroxy macrolide in an inert organic solvent such as methylene chloride, chloroform, pentane, hexane, cyclohexane, heptane or the like or mixtures thereof is treated with an alkyl, alkenyl or alkynyl trichloroacetimidate reagent (prepared by the reaction of an appropriate sodium alkoxide with trichloroacetonitrile, such as described by Wessel, H.P., Iversen, T., Bundle, D. R., *J. Chem. Soc., Perkin Trans. I*, 1985, 2247) in the presence of a mild acid catalyst such as trifluoromethanesulfonic acid, p-toluenesulfonic acid, methanesulfonic acid, benzenesulfonic acid, p-nitrobenzenesulfonic acid, p-bromobenzenesulfonic acid, p-chlorobenzenesulfonic acid, or p-methoxybenzenesulfonic acid, or mixtures thereof at a temperature of 20°-50° C., preferably room temperature, for a period of one hour to seven days, preferably one day, to give a mixture of the 3"-hydroxy 4"-O-alkyl, -alkenyl or -alkynyl, the 3"-O-alkyl, -alkenyl or -alkynyl 4"-hydroxy macrolide, and the 3", 4"-di-O-alkyl, -alkenyl or -alkynyl macrolide.

As shown in Reaction Scheme C the 14-hydroxyl group of the macrolide (wherein $R^5$, $R^{12}$, $R^{13}$, W and n are as defined above) may be eliminated by treatment with p-toluenesulfonic acid, benzenesulfonic acid, methanesulfonic acid, p-nitrobenzenesulfonic acid, p-bromobenzenesulfonic acid, p-chlorobenzenesulfonic acid, or p-methoxybenzenesulfonic acid, or mixtures thereof, in an inert organic solvent such as benzene, or toluene or the like at a temperature of 40° C. to solvent reflux temperature, preferably 60° C., for about 0.5 to 6 hours, or a sufficient period of time to eliminate the 14-hydroxyl group. Neutralization with an aqueous solution of a weak base such as aqueous saturated sodium bicarbonate gives the 14,15-dehydro macrolide. The 14-hydroxy group may also be eliminated by activation followed by basic elimination, as described in U.S. Pat. No. 4,894,366. (The resultant olefin may then be reduced by the hydrogenation methods essentially disclosed in Reaction Scheme O.)

By changing the sequence of synthethic steps, all possible variations of substitution can be achieved. For example, the C-14 hydroxyl group may be eliminated and the resultant double bond reduced prior to the introduction of alkenyl or alkynyl substituents at C-3" and/or C-4".

The procedures described in Reaction Scheme C may optionally be conducted prior to the procedures of Reaction Scheme B. Alternatively, the procedures described in Reaction Scheme D may be performed. In Reaction Scheme D the macrolide (wherein $R^{12}$ and $R^{13}$ are as defined above and $R^3$ and $R^4$ taken together form a double bond) is reduced with tri-n-butyltin hydride in the presence of tetrakis(triphenylphosphine)-palladium(O) catalyst and acetic acid in an organic solvent such as toluene or tetrahydrofuran at or near room temperature for about 2 to 10 hours to give the reduced macrolide.

As shown in Reaction Scheme E, a solution of the 3",4"-dihydroxy macrolide (or the 3"- or 4"-mono-substituted hydroxy macrolide) in an inert organic solvent such as methylene chloride, chloroform, pentane, hexane, cyclohexane, heptane or the like or mixtures thereof is treated with a protected-hydroxy substituted-alkenyl or alkynyl trichloroacetimidate (wherein A is as defined above and contains an allylic group or a benzylic group adjacent to the oxygen) (prepared by the reaction of an appropriate sodium alkoxide with trichloroacetonitrile, such as described by Wessel, H. P., Iversen, T., Bundle, D. R., *J. Chem. Soc., Perkin Trans. I*, 1985, 2247) in the presence of a mild acid catalyst such as trifluoromethanesulfonic acid, p-toluenesulfonic acid, methanesulfonic acid, benzenesulfonic acid, p-nitrobenzenesulfonic acid, p-bromobenzenesulfonic acid, p-chlorobenzenesulfonic acid, or p-methoxy-benzenesulfonic acid, or mixtures thereof of at a temperature of 20°-50° C., preferably 40° C., for a period of one hour to seven days, preferably 6 hours, to give a mixture of the protected hydroxy substituted 3"-O-alkenyl or -alkynyl 4"-hydroxy macrolide, the 3"-hydroxy 4"-O-alkenyl or -alkynyl macrolide and the 3",4"-di-O-alkenyl or -alkynyl macrolide. (The alkenyl or alkynyl group(s) may be reduced to the corresponding alkane essentially by the procedures described in Reaction Scheme O).

As further shown in Reaction Scheme E the silyl protecting group is removed such as by treatment with toluenesulfonic acid in a mixture of methanol and methylene chloride and the resultant primary hydroxy group is converted to the aldehyde by Dess-Martin oxidation or preferably by treatment with tetra-n-propylammonium perruthenate (TPAP) and 4-methylmorpholine-N-oxide (NMO).

Similarly, as shown in Reaction Scheme F, the appropriate 3",4"-dihydroxy macrolide (or the 3"-or 4"-mono-substituted hydroxy macrolide) is treated with a protected benzyloxy-substituted alkenyl or alkynyl trichloroacetimidate (wherein A is as defined above and contains an allylic group adjacent to the oxygen) under conditions essentially as described in Reaction Scheme E to give the macrolide bearing a pendent protected benzyloxy group.

As shown in Reaction Scheme G, a solution of the 3",4"-dihydroxy macrolide (or the 3"-or 4"-mono-substituted hydroxy macrolide) in an inert organic solvent such as methylene chloride, benzene, toluene, chloroform, or the like or mixtures thereof is treated with a triarylbismuth diacetate reagent (wherein aryl is protected benzaldehyde, benzyloxy, benzimidazole, benzothiazole, or benzoxazole) (prepared immediately prior to use by the addition of acetic acid to a suspension of a triarylbismuth carbonate in an inert organic solvent such as methylene chloride, choroform or the like or mixture thereof) in the presence of a catalytic amount of copper(II) acetate at a temperature of 20°-50° C., preferably room temperature, for a period of one hour to seven days, preferably one day, to give the 3"-and/or 4"-O-aryl-macrolide. Alternatively, the triarylbismuth(V) reagent can be prepared by treatment of a triarylbismuthine with a suitable oxidant such as peracetic acid, iodobenzene diacetate, bis(trifluoroacetoxy)iodobenzene and the like in an inert solvent such as methylene chloride, chloroform, benzene, toluene and the like. The triarylbismuth(V) reagent can be used without purification or can be purified by silica gel chromatography. Triarylbismuthines may be prepared by the reaction of an appropriate aryl Grignard reagent with bismuth trichloride in an inert organic solvent such as tetrahydrofuran, diethyl ether, or 1,4-dioxane, or mixtures thereof, at or near room temperature for a period of 1 to 48 hours. General procedures for the preparation and use of triaryl bismuth reagents may be found in Barton, D. H. E., et al., *J. Chem. Soc. Chem. Commun.*, 1986, 65 and references cited therein.

As shown in Reaction Scheme H the acetal protecting group is removed from the macrolide (wherein A is as defined above) by treatment with toluenesulfonic acid in methanol to provide the corresponding benzaldehyde.

Similarly, as shown in Reaction Scheme I, a solution of the 3",4"-dihydroxy macrolide (or the 3"- or 4"-mono-substituted hydroxy macrolide) in an inert organic solvent such as methylene chloride, benzene, toluene, chloroform, or the like or mixtures thereof is treated with an alkenyl triarylbismuth diacetate reagent (prepared immediately prior to use by the addition of acetic acid to a suspension of a triarylbismuth carbonate in an inert organic solvent such as methylene chloride, chloroform, or the like or mixtures thereof) in the presence of a catalytic amount of copper (II) acetate at a temperature of 20°-50° C., preferably 40° C., for a period of one hour to seven days, preferably 6 hours, to give a mixture of the 3"-O-styrene-4"-hydroxy macrolide, the 3"-hydroxy-4"-O-styrene macrolide, and the 3",4"-di-O-styrene macrolide.

As shown in Reaction Scheme J, the 3"-,4"-dihydroxy macrolide (or the 3" or 4" mono-substituted hydroxy macrolide) (wherein A is as defined above and is $CH_2$ or contains an allylic group or a benzylic group adjacent to the oxygen) is treated with an alkenyl trichloroacetimidate under conditions essentially as described in Reaction Scheme E to give the 3"- or 4"-O-alkenyl macrolide.

As shown in Reaction Scheme K, the O-alkenyl macrolide (wherein A is as defined above and is $CH_2$ or contains an allylic group adjacent to the oxygen) may be treated with a stochiometric amount of osmium tetraoxide in an inert organic solvent, such as diethyl ether or tetrahydrofuran, in the presence of an amine base, such as pyridine, at or near room temperature to give the corresponding glycol. Preferably, the glycol may be prepared by use of a catalytic amount of osmium tetraoxide in an inert organic solvent, such as tetrahydrofuran or diethyl ether, in the presence of a stochiometric oxidant, such as 4-methylmorpholine-N-oxide (NMO). Treatment of the glycol with sodium metaperiodate in a solution of tetrahydrofuran/water gives the aldehyde. Alternatively, the -O-alkenyl macrolide may be treated with sodium metaperiodate in the presence of a catalytic amount of osmium tetraoxide in an organic solvent to give the aldehyde directly.

A variety of imidazoles may be prepared from the corresponding aldehyde as illustrated in Reaction Scheme L. The aldehyde may be reacted with glyoxal, an α-keto aldehyde or an α,β-diketone (where in $R^7$ and $R^8$ are as defined above) in an alcoholic solvent, such as methanol, in the presence of ammonium hydroxide to give the corresponding imidazolyl macrolide. Treatment with hydrogen fluoride/pyridine removes any silyl protecting groups that may be present.

As shown in Reaction Scheme M, the free nitrogen of the imidazole substituent may be alkylated at either nitrogen atom of the imidazole by treatment with an appropriate alkyl, alkenyl or arylalkyl halide (wherein LG is I, Br or Cl) in the presence of silver (I) oxide to give the desired N-substituted imidazolyl macrolide.

As shown in Reaction Scheme N, the imidazole may be further modified by utilizing the methods of Reaction Scheme G (wherein $R^1_a$ is unsubstituted or substituted phenyl, naphthyl or biphenyl) or Reaction Scheme E (wherein $R^1_b$ is unsubstituted or substituted alkyl, alkenyl or alkynyl). It is noted that such procedures may also be performed on dihydroxyl imidazoles to give the disubstituted imidazole macrolides, and by employing appropriate protecting groups to give the mixed disubstituted imidazoles. The procedures described in Reaction Scheme L-N are readily applicable to the preparation of compounds bearing analagous functionality at C-3".

As shown in Reaction Scheme O the macrolide (wherein A is alkenyl, substituted alkenyl, alkynyl or substituted alkynyl) is reduced under an atmosphere of hydrogen in the presence of a noble metal catalyst, such as rhodium on carbon catalyst or rhodium on alumina catalyst, at a pressure of atmospheric pressure to 40 psig, at or near room temperature in an organic solvent such as ethyl acetate or ethanol for about 1 to 24 hours, or until the requisite amount of hydrogen is absorbed to reduce the olefin and give the reduced macrolide (wherein $A^a$ is alkyl or substituted alkyl). The procedures of Scheme O may be conducted prior to the formation of the imidazole group.

As shown in Reaction Scheme P, benzothiazole compounds can be prepared by treatment of the suitably protected macrolide with a benzothiazole containing a leaving group (LG=halogen or OTf) with a suitable base such as silver (I) oxide.

As shown in Reaction Scheme Q, benzoxazole compounds can be prepared by treatment of the suitably protected macrolide with a benzothiazole containing a leaving group (LG=halogen or OTf) with a suitable base such as silver (I) oxide. Such compounds may be modified essentially as described in Reaction Schemes M and N.

As shown in Reaction Scheme R, imidazolidyl ether containing compounds can be prepared by treatment of the suitable protected macrolide with an imidazolidyl reagent bearing a leaving group such as p-toluenesulfonate, p-nitrobenzenesulfonate, methanesulfonate, acetate, trifluoroacetate, benzoate, p-nitrobenzoate, and the like in an inert solvent such as tetrahydrofuran, diethyl ether, methylene chloride, benzene, acetonitrile with an amine base such as triethyl amine, diisopropylethyl amine, pyridine, 2,6-dimethylpyridine and the like at or about room temperature. Such compounds may be modified essentially as described in Reaction Schemes M and N.

A hydroxyl or fluoro group may be introduced at C-20 essentially by the procedures of Reaction Scheme S. As shown in Reaction Scheme S the 4",14-dihydroxy macrolide (or the 14-deoxy macrolide) is protected as the di(t-butyldimethylsilyl ether) by treatment with t-butyldimethylsilyl triflate in an inert organic solvent such as methylene chloride, chloroform or the like in the presence of a non-nucleophilic base such as 2,6-lutidine. The diprotected macrolide is oxidized at C-20 as further shown in Reaction Scheme S by treatment with selenium dioxide in an alcoholic solvent such as ethanol in the presence of pyridine at solvent reflux temperature to give the 20-hydroxy macrolide. The 20-hydroxy macrolide may be further derivatized by alkylation, acylation or phosphorylation to give ether, ester or phosphate derivatives by procedures well known to the practitioner of the art. As further illustrated, treatment of the 20-hydroxy-4",14-di-OTBS macrolide with diethylaminosulfur trifluoride in an inert organic solvent such as methylene chloride, chloroform or the like at a temperature of about 0° C. to −90° C., preferably about −78° C., gives the 20-fluoro 4",14-di-OTBS macrolide. Removal of the silyl ether protecting groups by treatment with hydrogen fluoride-pyridine complex in tetrahydrofuran gives the 20-fluoro 4",14-dihydroxy macrolide which may be further derivatized by any of the methods previously described. Reaction Scheme S may also be performed on the 3",4",14-trihydroxy macrolide to give the 20-fluoro 3",4",14-trihydroxy macrolide. The procedures of Reaction Scheme S may be conducted prior to, concurrent with, or subsequent to the procedures of Reaction Schemes A-R.

The object compounds of Formula I obtained according to the reactions as explained above can be isolated and purified in a conventional manner, for example, extraction, precipitation, fractional crystallization, recrystallization, chromatography, and the like.

In the compounds of Formula I $R^1O$- may be substituted at C-3" or C-4" or both C-3" and C-4", but it is preferred that $R^1O$- is substituted at C-4".

It is to be noted that in the aforementioned reactions and the post-treatment of the reaction mixture therein, the stereoisomer(s) of starting and object compounds due to asymmetric carbon atom(s) or double bond(s) of the object compounds of Formula I may occasionally be transformed into the other stereoisomer(s), and such cases are also included within the scope of the present invention.

In the present invention, compounds with asymmetric centers may occur as racemates, as diastereomeric mixtures and as individual diastereomers, with all isomeric forms of the compounds being included in the present invention. These may be prepared by methods such as those disclosed in publications which describe synthetic routes to fragments of the macrolide FR-900506 and the total synthesis of the macrolide FR-900506 itself (*J. Am. Chem. Soc.* 1989, 111, 1157; *J. Am. Chem. Soc.* 1990, 112, 2998; *J. Org. Chem.* 1990, 55, 2786; *J. Am. Chem. Soc.* 1990, 112, 5583. *Tetrahedron Lett.* 1988, 29, 277; *Tetrahedron Lett.* 1988, 29, 281; *Tetrahedron Lett.* 1988, 29, 3895; *J. Org. Chem.* 1988, 53, 4643; *Tetrahedron Lett.* 1988, 29, 4245; *Tetrahedron Lett.* 1988, 29, 4481; *J. Org. Chem.* 1989, 54, 9; *J. Org. Chem.* 1989, 54, 11; *J. Org. Chem.* 1989, 54, 12; *J. Org. Chem.* 1989, 54, 15; *J. Org. Chem.* 1989, 54, 17; *Tetrahedron Lett.* 1989, 30, 919; *Tetrahedron Lett.* 1989, 30, 1037; *J. Org. Chem.* 1989, 54, 2785; *J. Org. Chem.* 1989, 54, 4267; *Tetrahedron Lett.* 1989, 30, 5235; *Tetrahedron Lett.* 1989, 30, 6611; *Tetrahedron Lett.* 1989, 30, 6963; *Synlett* 1990, 38; *J. Org. Chem.* 1990, 55, 2284; *J. Org. Chem.* 1990, 55, 2771; *J. Org. Chem.* 1990, 55, 2776; *Tetrahedron Lett.* 1990, 31, 1439; *Tetrahedron Lett.* 1990, 31, 1443; *Tetrahedron Lett.* 1990, 31, 3007; *Tetrahedron Lett.* 1990, 31, 3283, 3287).

The compounds of the present invention are capable of forming salts with various inorganic and organic acids and bases and such salts are also within the scope of this invention. Examples of such acid addition salts (which are negative counterions defined herein as $M^-$) include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, tosylate, and undecanoate. Base salts (which are positive counterions defined herein as $M^+$) include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups such as the C-3 nitrogen of an imidazole may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

C. Utility of the compounds within the scope of the invention

The compounds of Formula I may be employed as immunosuppressants or antimicrobial compounds by methods and in dosages known in the prior art for compounds of Formula II. These compounds possess pharmacological activity such as immunosuppressive activity, antimicrobial activity, and the like, and therefore are useful for the treatment and prevention of the resistance to transplantation or transplantation rejection of organs or tissues (such as heart, kidney, liver, lung, bone marrow, cornea, pancreas, intestinum tenue, limb, muscle, nervus, medulla ossium, duodenum, small-bowel, medulla ossium, skin, pancreatic islet-cell, etc. including xeno transplantation), graft-versus-host diseases by medulla ossium transplantation, autoimmune diseases such as rheumatoid arthritis, systemic lupus erythematosis, nephrotic syndrome lupus, Hastimoto's thyroiditis, multiple sclerosis, myasthenia gravis, type I diabetes mellitus, type II adult onset diabetes, uveitis, nephrotic syndrome, steroid-dependent and steroid-resistant nephrosis, Palmo-planter pustulosis, allergic encephalomyelitis, glomerulonephritis, etc., and infectious diseases caused by pathogenic microorganisms.

The compounds of Formula I are also useful for treating inflammatory, proliferative and hyperproliferative skin diseases and cutaneous manifestations of immunologically-mediated illnesses such as: psoriasis, psoriatic arthritis, atopical dermatitis, contact dermatitis and further eczematous dermatitises, seborrhoeic dermatitis, *Lichen planus*, Pemphigus, bullous Pemphigoid, *Epidermolysis bullosa*, urticaria, angioedemas, vasculitides, erythemas, cutaneous eosinophilias, acne *Alopecia areata*, eosinophilic fasciitis, and atherosclerosis. More particularly, the compounds of Formula I are useful in hair revitalizing, such as in the treatment of male or female pattern alopecia or alopecia senilis, by providing epilation prevention, hair germination, and/or a promotion of hair generation and hair growth.

The compounds of Formula I are further useful in the treatment of respiratory diseases, for example sarcoidosis, fibroid lung, idiopathic interstitial pneumonia, and reversible obstructive airways disease, including conditions such as asthma, including bronchial asthma, allergic asthma, intrinsic asthma, extrinsic asthma and dust asthma, particularly chronic or inveterate asthma (for example late asthma and airway hyperresponsiveness), bronchitis and the like. The compounds of Formula I may also be useful for treating hepatic injury associated with ischemia.

The compounds of the invention are also indicated in certain eye diseases such as keratoconjunctivitis, vernal conjunctivitis, uveitis associated with Behcet's disease, keratitis, herpetic keratitis, conical cornea, dystorphia epithelialis corneae, corneal leukoma, ocular pemphigus, Mooren's ulcer, Scleritis, Graves' ophthalmopathy, severe intraocular inflammation, and the like.

The compounds of Formula I are also useful for treating multidrug resistance of tumor cells, (i.e. enhancing the activity and/or sensitivity of chemotherapeutic agents), preventing or treating inflammation of mucosa or blood vessels (such as leukotriene B$_4$-mediated diseases, gastric ulcers, vascular damage caused by ischemic diseases and thrombosis, ischemic bowel disease, inflammatory bowel disease (e.g., Crohn's disease and ulcerative colitis) necrotizing enterocolitis), or intestinal lesions associated with thermal burns, cytomegalovirus infection, particularly HCMV infection.

Further, the compounds of Formula I are also useful for treating or preventing renal diseases including interstitial nephritis, Goodpasture's syndrome, hemolytic-uremic syndrome and diabetic nephropathy; nervous diseases selected from multiple myositis, Guillain-Barre syndrome, Meniere's disease and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis and anerythroplasia; bone diseases including osteoporosis; respiratory diseases including sarcoidosis, fibroid lung and idiopathic interstitial pneumonia; skin diseases including dermatomyositis, leukoderma vulgaris, ichthyosis vulgaris, photoallergic sensitivity and cutaneous T cell lymphoma; circulatory diseases including arteriosclerosis, aortitis syndrome, polyarteritis nodosa and myocardosis; collagen including scleroderma, Wegener's granuloma and Sjogren's syndrome; adiposis; eosinophilic fasciitis; periodontal disease; nephrotic syndrome; hemolytic-uremic syndrome; and muscular dystrophy.

Further, the compounds of the invention are indicated in the treatment of diseases including intestinal inflammations/allergies such as Coeliac disease, proctitis, eosinophilic gastroenteritis, mastocytosis, Crohn's disease and ulcerative colitis; and food related allergic diseases which have symptomatic manifestation remote from the gastrointestinal tract, for example migraine, rhinitis and eczema.

The compounds of the invention also have liver regenerating activity and/or activity in stimulating hypertrophy and hyperplasia of hepatocytes. Therefore, they are useful for the treatment and prevention of hepatic diseases such as immunogenic diseases (e.g. chronic autoimmune liver diseases including autoimmune hepatitis, primary biliary cirrhosis and sclerosing cholangitis), partial liver resection, acute liver necrosis (e.g. necrosis caused by toxins, viral hepatitis, shock or anoxia), B-virus hepatitis, non-A/non-B hepatitis and cirrhosis.

The compounds of the invention are also indicated for use as antimicrobial agents, and thus may be used in the treatment of diseases caused by pathogenic microorganisms and the like.

The compounds of Formula I may also act as antagonists of macrocyclic immunosuppressive compounds, including derivatives of 12-(2'-cyclohexyl-1'-methylvinyl)-13,19,21,27-tetramethyl-11,28-dioxa-4-azatricyclo[22.3.1.0$^{4,9}$]octacos-18-ene, and so be useful in the treatment of immunodepression (such as AIDS, cancer, senile dementia, trauma (including wound healing, surgery and shock), chronic bacterial infection and certain central nervous system disorders), overdosages or toxicity of such immunosuppressive compounds, and as an adjunct to the administration of an antigen in vaccination.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. For example, the compounds of Formula I may be utilized with hydroxypropyl methylcellulose essentially as described in U.S. Pat. No. 4,916,138, issued Apr. 10, 1990, or with a surfactant essentially as described in EPO Publication 0,428,169. Oral dosage forms may be prepared essentially as described by T. Hondo, et al., *Transplantation Proceedings*, 1987, XIX, Supp. 6, 17-22. Dosage forms for external application may be prepared essentially as described in EPO Publication 0,423,714. The active object compound is included in the pharmaceutical composition in an amount sufficient to produce the desired effect upon the process or condition of diseases.

For the treatment of these conditions and diseases caused by immmunoirregularity a compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For the treatment of reversible obstructive airways disease, it is preferable that the compound of Formula I be administered by inhalation to the lung, especially in the form of a powder.

For modifying the activity and/or toxicity of FK-506-type immunosuppressants, a compound of Formula I may be administered prior to, in conjuction with or subsequent to the administration of an FK-506-type of a compound.

The compounds of Formula I may optionally be employed in co-therapy with anti-proliferative agents. Particularly preferred is co-therapy with an antiproliferative agent selected from the group consisting of azathioprine (AZA), brequinar sodium, deoxyspergualin (DSG), mizaribine, mycophenolic acid morpholino ester (RS-61443), cyclosporin and rapamycin.

Dosage levels of the compounds of the present invention are of the order from about 0.005 mg to about 50 mg per kilogram of body weight per day, preferably from about 0.1 mg to about 10 mg per kilogram of body weight per day, are useful in the treatment of the above-indicated conditions (from about 0.7 mg to about 3.5 mg per patient per day, assuming a 70 kg patient). In addition, the compounds of the present invention may be administered on an intermittent basis; i.e. at daily, semi-weekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally comprise from about 0.01 mg to about 500 mg, and preferably about 0.5 mg to about 100 mg of active ingredient. For external administration the compound of Formula I may be formulated within the range of, for example, 0.0001% to 60% by weight, preferably from 0.001 to 10% by weight, and most preferably from about 0.005 to 0.8% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

EXAMPLE 1

17-Ethyl-1-hydroxy-14-(tert-butyldimethylsiloxy)-12-[2'-(4''-(2'''-imidazolylmethyloxy)-3'-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1--hydroxy-14-(tert-butyldimethylsiloxy)-12-[2'-(4''-ethanaloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (59 mg in 0.75 ml methanol) was added glyoxal (15 μl of a 40% water solution) followed by ammonium hydroxide (50 μl of a 58% water solution) and the mixture stirred at room temperature. After 15 hours, the solution was concentrated in vacuo and the mixture purified by flash chromatography on silica gel (ethyl acetate:hexane (2:1)+1% methanol, then 2% ammonium hydroxide, 5% methanol in methylene chloride) to give the title compound (45 mg).

MASS: (FAB) 993 (M+Li)
($^1$H NMR consistent with the desired structure).

EXAMPLE 2

17-Ethyl-1,14-dihydroxy-12-[2'-(4''-(2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4''-(2'''-imidazolylmethyl)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (45 mg in 0.75 ml tetrahydrofuran contained in a polypropylene vial) was added 50 μl of a solution of hydrogen fluoride-pyridine complex (40% in (2:1) tetrahydrofuran:pyridine) and the mixture stirred at room temperature. After 20 hours, the reaction was quenched by the careful addition of saturated sodium bicarbonate and extracted with ethyl acetate. The combined organics were dried over magnesium sulfate, concentrated in vacuo and purified by flash chromatography (ethyl acetate:hexane (2:1)+1% methanol, then 2% ammonium hydroxide, 5% methanol in methylene chloride) to give the title compound (19 mg).

MASS: (FAB) 879 (M+Li)
Partial $^1$H NMR δ: 7.01(brs, 2H); 5.31M, 518 m (brd J=3.0 Hz, 1H); 4.41(brd J=14 Hz, 1H); 3.51(s, 3H).

EXAMPLE 3

17-Ethyl-1-hydroxy-14-(tert-butyldimethylsiloxy)-12-[2'-(4''-(4'''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1--hydroxy-14-(tert-butyldimethylsiloxy)-12-[2'-(4''-ethanaloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (77.5 mg in 1.0 ml methanol) was added phenylglyoxal monohydrate (18.6 mg) followed by ammonium hydroxide (150 μl of a 58% water solution) and the mixture stirred at room temperature. After 5 hours, the solution was concentrated in vacuo and the mixture purified by flash chromatography on silica gel (ethyl acetate:hexane (2:1)+1% methanol) to give the title compound (45 mg).

($^1$H NMR consistent with the desired structure).

EXAMPLE 4

17-Ethyl-1,14-dihydroxy-12-[2'-(4''-(4'''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4''-(4'''-phenyl-2'''-imidazolylmethyl)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (45 mg in 0.75 ml tetrahydrofuran contained in a polypropylene vial) was added 50 μl of a solution of hydrogen fluoride-pyridine complex (40% in (2:1) tetrahydrofuran pyridine) and the mixture stirred at room temperature. After 22 hours, the reaction was quenched by the careful addition of saturated sodium bicarbonate and extracted with ethyl acetate. The combined organics were dried over magnesium sulfate, concentrated in vacuo and purified by flash chromatography (ethyl acetate:hexane (4:1)+1% methanol, then 2% ammonium hydroxide, 5% methanol in methylene chloride) to give the title compound (23 mg).

MASS: (FAB) 954 (M+Li)

Partial $^1$H NMR $\delta$: 7.75(m); 7.36(m); 5.31M, 5.19 m (brd J=3.0 Hz, 1H); 4.85 m, 4.21M(brs, 1H); 4.41 (brd J=14 Hz, 1H).

EXAMPLE 5

17-Ethyl-1-hydroxy-14-(tert-butyldimethylsiloxy)-1 2-[2'-(4''-(4'''-methyl-2'''-imidazolylmethyloxy) -3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1--hydroxy-14-(tert-butyldimethylsiloxy)-12-[2'-(4''-ethanaloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (59 mg in 0.75 ml methanol) was added pyruvic aldehyde (7.5 µl of a 40% water solution) followed by ammonium hydroxide (40 µl of a 58% water solution) and the mixture stirred at room temperature. After 4 hours, the solution was concentrated in vacuo and the mixture purified by flash chromatography on silica gel (ethyl acetate:hexane (2:1)+1% methanol, then 2% ammonium hydroxide, 5% methanol in methylene chloride) to give the title compound (20 mg).

($^1$H NMR consistent with the desired structure).

EXAMPLE 6

17-Ethyl-1,14-dihydroxy-12-[2'-(4''--(4'''-methyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4''-(4'''-methyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (20 mg in 1.0 ml tetrahydrofuran contained in a polypropylene vial) was added 400 µl of a solution of hydrogen fluoridepyridine complex (40% in (2:1) tetrahydrofuran:pyridine) and the mixture stirred at room temperature. After 20 hours, the reaction was quenched by the careful addition of saturated sodium bicarbonate and extracted with ethyl acetate. The combined organics were dried over magnesium sulfate, concentrated in vacuo and purified by flash chromatography (ethyl acetate:hexane (2:1)+1% methanol, then 2% ammonium hydroxide, 5% methanol in methylene chloride) to give the title compound (16 mg).

MASS: (FAB) 892 (M+Li)

Partial $^1$H NMR $\delta$: 6.66 (s, 1H); 5.31M, 5.19 m brd J=3.0 Hz, 1H); 4.41 (brd J=14 Hz, 1H); 3.49 (s, 3H); 2.22(s, 3H).

EXAMPLE 7

17-Ethyl-1-hydroxy-14-(tert-butyldimethylsiloxy)--12-[2'-(4''-(4'''-methyl-5'''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1--hydroxy-14-(tert-butyldimethylsiloxy)-12-[2'-(4''-ethanaloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (59 mg in 0.75 ml methanol) was added 1-phenyl-1,2-propanedione (10 µl) followed by ammonium hydroxide (80 µl of a 58% water solution) and the mixture stirred at room temperature. After 5 hours, the solution was concentrated in vacuo and the mixture purified by flash chromatography on silica gel (ethyl acetate:hexane (4:1)+1% methanol) to give the title compound (54.7 mg).

($^1$H NMR consistent with the desired structure).

EXAMPLE 8

17-Ethyl-1,14-dihydroxy-12-[2'-(4''-(4'''-methyl-5'''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a solution of 17-ethyl-1-hydroxy-14-(tert-butyldimethylsiloxy)-12-[2'-(4''-(4'''-methyl--5'''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (54.7 mg in 1.0 ml tetrahydrofuran contained in a polypropylene vial) was added 600 µl of a solution of hydrogen fluoridepyridine complex (40% in (2:1) tetrahydrofuran: pyridine) and the mixture stirred at room temperature. After 24 hours, the reaction was quenched by the careful addition of saturated sodium bicarbonate and extracted with ethyl acetate. The combined organics were dried over magnesium sulfate, concentrated in vacuo and purified by flash chromatography (ethyl acetate:hexane (2:1)+1% methanol, then 2% ammonium hydroxide, 5% methanol in methylene chloride) to give the title compound (28.6 mg).

MASS: (FAB) 962 (M+Li)

Partial $^1$H NMR $\delta$: 7.39 (m); 5.31M, 5.19 m (brd J=3.0 Hz, 1H); 4.59 (brd J=4.0 Hz, 1H); 4.41 (brd J=14 Hz, 1H); 3.53 (s, 3H); 2.42 (s, 3H).

EXAMPLE 9

17-Ethyl-1-hydroxy-14-(tert-butyldimethylsiloxy)-12-[ 2'-(4''-(4'''-methoxymethyl-5'''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To 6.4 mg of 1-phenyl-3-methoxy-1,2-propanedione was added a solution of 17-ethyl-1--hydroxy-14-(tert-butyldimethylsiloxy)-12-[2'-(4''-ethanaloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (59 mg in 0.75 ml methanol) followed by ammonium hydroxide (55 µl of a 58% water solution) and the mixture stirred at room temperature. After 4 hours, the solution was concentrated in vacuo and the mixture purified by flash chromatography on silica gel (ethyl acetate:hexane (2:1)+1% methanol) to give the title compound (10 mg).

($^1$H NMR consistent with the desired structure).

EXAMPLE 10

17-Ethyl-1,14-dihydroxy-12-[2'-(4''-(4'''-methoxymethyl-5'''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4''-(4'''-methoxymethyl-5'''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo]22.3.1.0$^{4,9}$]octacos-18-ene-2,3,10,16-tetraone (54.7 mg in 1.0 ml tetrahydrofuran contained in a polypropylene vial) was added 100 μl of a solution of hydrogen fluoride-pyridine complex (40% in (2:1) tetrahydrofuran:pyridine) and the mixture stirred at room temperature. After 18 hours, the reaction was quenched by the careful addition of saturated sodium bicarbonate and extracted with ethyl acetate. The combined organics were dried over magnesium sulfate, concentrated in vacuo and purified by flash chromatography (ethyl acetate:hexane (2:1)+1% methanol, then 2% ammonium hydroxide, 5% methanol in methylene chloride) to give the title compound (5 mg).

MASS: (FAB) 992 (M+)

Partial $^1$H NMR δ: 7.47 (m, 5H); 5.31M, 5.19 m (s, 1H); 4.41 (brd J=14 Hz, 1H); 3.48 (dd J=18, 10 Hz, 2H); 3.37 (s, 3H).

EXAMPLE 11

17-Ethyl-1-hydroxy-12-[2'-(4''-(4'''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-ethanaloxy-3''-methoxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone (77.5 mg in 1.0 ml methanol) was added phenylglyoxal monohydrate (18.6 mg) followed by ammonium hydroxide (150 ml of a 58% water solution) and the mixture stirred at room temperature. After 5 hours, the solution was concentrated in vacuo and the mixture purified by flash chromatography on silica gel (ethyl acetate:hexane (2:1)+1% methanol) to give the title compound (45 mg).

MASS: (FAB) 954 (M+Li)

Partial $^1$H NMR δ: 7.76 (d J=8 Hz, 2H); 7.38 (m, 3H); 4.47 m, 4.31M (brs, 1H); 4.41 (brd J=14 Hz, 1H); 3.58 m, 3.54M (s, 3H).

EXAMPLE 12

17-Ethyl-1-hydroxy-12-[2'-(4''-(tert-butyldimethylsiloxy)-3''-(2''',3'''-dihydroxypropyloxy)-cyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a solution of 17-ethyl-1-hydroxy-12-[2'-(4''-(tert-butyldimethylsiloxy)-3''-allyloxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (182 mg in 2 ml dry diethyl ether) was added 100 μl pyridine followed by 880 μl of a 0.25M osmium tetraoxide solution in THF and the mixture stirred at room temperature. After 15 minutes, 5 ml of a 20% sodium bisulfite solution were added and the mixture diluted with 10 ml ethyl acetate. The layers were separated and the organic portion re-extracted with 20% sodium bisulfite (3×5 ml) then washed with a saturated brine solution and dried over sodium sulfate. The concentrate was purified by flash chromatography on silica gel (ethyl acetate:hexane (2:1)+1% methanol) to give the title compound (112 mg)

($^1$H NMR consistent with the desired structure).

EXAMPLE 13

17-Ethyl-1-hydroxy-12-[2'-(4''-(tert-butyldimethylsiloxy)-3''-ethanaloxycyclohexyl)-1'-methylvinyl]-23,25-dimethoxy-13,19,21,27-tetramethyl-11,28-dioxa-4-azatricyclo[22.3.1.0$^{4,9}$]octacos-18-eve-2,3,10,16-tetraone To a solution of 17-ethyl-1-hydroxy-12-[2'-(4''-(tert-butyldimethylsiloxy)-3''-(2''',3'''-dihydroxy-propyloxy)-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetrone (112 mg in 5 ml 40% aqueous tetrahydrofuran) was added sodium metaperiodate (38 mg) and the mixture stirred vigorously for 2 hours. At this time an additional 20 mg of sodium metaperiodate were added. After 2 hours the mixture was diluted with ethyl acetate and extracted with half-saturated sodium bicarbonate. The organic portion was dried over magnesium sulfate and purified by flash chromatography on silica gel (ethyl acetate:hexane (1:2)+1% methanol) to give the title compound (86 mg)

($^1$H NMR consistent with the desired structure).

EXAMPLE 14

17-Ethyl-1-hydroxy-12-[2'-(4'''-(tert-butyldimethylsiloxy)-3''-(4'''-phenyl-2'''-imidazolylmethyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-(tert-butyldimethylsiloxy)-3''-ethanaloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (25.6 mg in 0.5 ml methanol) was added phenylglyoxal monohydrate (7.6 mg) followed by ammonium hydroxide (50 μl of a 58% water solution) and the mixture stirred at room temperature. After 4 hours, the solution was concentrated in vacuo and the mixture purified by flash chromatography on silica gel (ethyl acetate:hexane (2:1)+1% methanol) to give the title compound (7 mg).

($^1$H NMR consistent with the desired structure)

EXAMPLE 15

17-Ethyl-1-hydroxy-12-[2'-(4''--hydroxy-3''-(4'''-phenyl-2'''-imidazolylmethyloxy)-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-(tert-butyldimethylsiloxy)-3''-(4'''-phenyl-2'''-imidazolylmethyloxy)-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (7 mg in 400 μl tetrahydrofuran contained in a polypropylene vial) was added 30 μl of a solution of hydrogen fluoride-pyridine complex (40% in (2:1) tetrahydrofuran:pyridine) and the mixture stirred at room temperature. After 3 hours, the reaction was quenched by the careful addition of saturated sodium bicarbonate and extracted with ethyl acetate. The combined organics were dried over magnesium sulfate, concentrated in vacuo and purified by flash chromatography (ethyl acetate:hexane (4:1)+1% methanol, then 2% ammonium hydroxide, 5% methanol in methylene chloride) to give the title compound (4 mg).

MASS: (FAB) 918 (M+)

Partial $^1$H NMR δ: 7.75 (m); 7.36 (t J=9 Hz, 2H); 4.47 m, 4.31M (brs, 1H); 4.41 (brd J=14 Hz, 1H).

EXAMPLE 16

17-Ethyl-1,14-dihydroxy-12-[2'-(4''-(1'''-methyl-4'''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''--(4'''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (10 mg in 200 μl dry acetonitrile) was added iodomethane (1.3 μl) followed by silver (I) oxide (2.6 mg) and the mixture stirred vigorously at room temperature. After 4 hours the mixture was diluted with 1 ml ethyl acetate and filtered through diatomaceous earth. The concentrate was purified by flash chromatography on silica gel (ethyl acetate:hexane (4:1)+1% methanol) to give the title compound (4.5 mg).

MASS: (FAB) 762 (M+)

Partial $^1$H NMR δ: 7.72 (d J=8 Hz, 2H); 7.34 (t J=9 Hz, 2H); 7.14 (s, J=1H); 5.31M, 5.19 m (brd J=3.0 Hz, 1H); 4.77 (s, 2H); 4.41 (brd J=14 Hz, 1H); 3.77 (s, 3H).

EXAMPLE 17

17-Ethyl-1-hydroxy-14-(tert-butyldimethylsiloxy)-12-[2'-(4''-(1'''-benzyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4''-(2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (24 mg in 0.5 ml dry acetonitrile) was added benzylbromide (6 μl) followed by silver (I) oxide (6 mg) and the mixture stirred vigorously at room temperature. After 4 hours the mixture was diluted with 1.5 ml ethyl acetate and filtered through diatomaceous earth. The concentrate was purified by flash chromatography on silica gel (ethyl acetate:hexane (2:1)+1% methanol, then (4:1)+1% methanol) to give the title compound (10 mg)

($^1$H NMR consistent with the desired structure).

EXAMPLE 18

17-Ethyl-1,14-dihydroxy-12-[2'-(4''--(1'''-benzyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4''-(1'''-benzyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (10 mg in 800 μl tetrahydrofuran contained in a polypropylene vial) was added 200 μl of a solution of hydrogen fluoride-pyridine complex (40% in (2:1) tetrahydrofuran:pyridine) and the mixture stirred at room temperature. After 21 hours, the reaction was quenched by the careful addition of saturated sodium bicarbonate and extracted with ethyl acetate. The combined organics were dried over magnesium sulfate, concentrated in vacuo and purified by flash chromatography (ethyl acetate:hexane (2:1)+1% methanol, then 2% ammonium hydroxide, 5% methanol in methylene chloride) to give the title compound (6 mg).

MASS: (FAB) 962 (M+)

Partial $^1$H NMR δ: 6.98 (s, 1H); 6.85 (s, 1H); 5.31M, 5.19 m (brs, 1H); 5.28 (s, 2H); 4.85 m, 4.20M (s, 1H); 4.69 (s, 2H); 4.41 (brd J=14 Hz, 1H).

EXAMPLE 19

17-Ethyl-1-hydroxy-14-(tert-butyldimethylsiloxy)-12-[2'-(4''-(1'''-m-fluorobenzyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4''-(2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (17.5 mg in 400 μl dry acetonitrile) was added m-fluorobenzylbromide (4.5 μl) followed by silver (I) oxide (4.5 mg) and the mixture stirred vigorously at room temperature. After 5 hours the mixture was diluted with 1.5 ml ethyl acetate and filtered through diatomaceous earth. The concentrate was purified by flash chromatography on silica gel (ethyl acetate:hexane (2:1)+1% methanol, then (4:1)+1% methanol) to give the title compound (9 mg) ($^1$H NMR consistent with the desired structure).

EXAMPLE 20

17-Ethyl-1,14-dihydroxy-12-[2'-(4''-(1'''-m--fluorobenzyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4''-(1'''-m-fluorobenzyl-2'''--imidazolylmethyloxy)-3''-methoxycyclohexyl)-1'-methylvinyl]-23,25-dimethoxy-13,19,21,27-tetramethyl- 11,28-dioxa-4-azatricyclo[22.3.1.0⁴,⁹]octacos-18-ene-2,3,10,16-tetraone (9 mg in 450 μl tetrahydrofuran contained in a polypropylene vial) was added 120 μl of a solution of hydrogen fluoride-pyridine complex (40% in (2:1) tetrahydrofuran:pyridine) and the mixture stirred at room temperature. After 21 hours, the reaction was quenched by the careful addition of saturated sodium bicarbonate and extracted with ethyl acetate. The combined organics were dried over magnesium sulfate, concentrated in vacuo and purified by flash chromatography (ethyl acetate:hexane (2:1)+1% methanol, then 2% ammonium hydroxide, 5% methanol in methylene chloride) to give the title compound (5.5 mg).

MASS: (FAB) 981 (M+1)
Partial $^1$H NMR δ: 6.98 (s, 1H); 6.85 (s, 1H); 5.31M, 5.19 m (brd J=3.0 Hz, 1H); 5.30 (s, 2H); 4.85 m, 4.20M (s, 1H); 4.69 (s, 2H); 4.41 (brd J=14 Hz, 1H).

EXAMPLE 21

17-Ethyl-1-hydroxy-14-(tert-butyldimethylsiloxy)-12-[2'-(4''-(m-(tert-butyldimethylsiloxymethyl)benzyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone To a solution of 17-ethyl-1-1-hydroxy-14-(tert-butyldimethylsiloxy)-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone (230 mg in 3 ml 33% methylene chloride in cyclohexane) was added m-(tert-butyldimethylsiloxymethyl)benzyl trichloroacetimidate (198 μl neat) and the reagents allowed to mix for 5 minutes. Trifluoromethanesulfonic acid (4.5 μl neat) was added slowly via syringe and the mixture stirred at room temperature. After 1 hour the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate:hexane (1:2)+1% methanol) gave the title compound (165 mg)

($^1$H NMR consistent with the desired structure).

EXAMPLE 22

17-Ethyl-1-hydroxy-14-(tert-butyldimethylsiloxy)-12-[2'-(4''-(m-hydroxymethyl-benzyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone To a solution of 17-ethyl-1-hydroxy-14-(tert-b utyldimethylsiloxy)-12-[2'-(4''-(m-(tert-butyldimethylsiloxymethyl)benzyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone (120 mg in 2.5 ml methylene chloride) was added 2.4 ml of a 10% solution of p-toluenesulfonic acid in methanol and the mixture stirred at room temperature. After 25 minutes, the reaction was quenched by the addition of 3 ml saturated sodium bicarbonate, extracted with ethyl acetate (2×20 ml), and washed with brine. The combined organics were dried over magnesium sulfate and the concentrate purified by flash chromatography on silica gel (ethyl acetate:hexane (1:3)+1% methanol) to give the title compound (79 mg)

($^1$H NMR consistent with the desired structure).

EXAMPLE 23

17-Ethyl-1-hydroxy-14-(tert-butyldimethylsiloxy)-12-[2'-(4''-(m-formylbenzyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone To a solution of 17-ethyl-1-hydroxy-14-(tert-t-butyldimethylsiloxy)-12-[2'-(4''-(m-hydroxymethylbenzyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone (79 mg in 1 ml dry methylene chloride) was added 39 mg of the Dess-Martin periodinane and the mixture stirred at room temperature. After 15 minutes, 1 ml of saturated sodium bicarbonate was added and the mixture extracted with ethyl acetate. The organic portion was washed with brine, dried over magnesium sulfate and concentrated in vacuo. Purification of the concentrate by flash chromatography on silica gel (ethyl acetate:hexane (1:2)+1% methanol) gave the title compound (68.4 mg)

($^1$H NMR consistent with the desired structure).

EXAMPLE 24

17-Ethyl-1-hydroxy-14-(tert-butyldimethylsiloxy)-12-[2'-(4''-(m-2'''-imidazolylbenzyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone To a solution of 17-ethyl-1-hydroxy--14-(tert-butyldimethylsiloxy)-12-[2'-(4''-(m-formylbenzyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone (33.4 mg in 0.5 ml methanol) was added glyoxal (12 μl of a 40% water solution) followed by ammonium hydroxide (20 μl of a 58% water solution) and the mixture stirred at room temperature. After 20 hours, the solution was concentrated in vacuo and the mixture purified by flash chromatography on silica gel (ethyl acetate:hexane (2:1)+1% methanol, then 2% ammonium hydroxide, 5% methanol in methylene chloride) to give the title compound (20 mg)

($^1$H NMR consistent with the desired structure).

EXAMPLE 25

17-Ethyl-1,14-dihydroxy-12-[2'-(4''-(m-2'''-imidazolybenzyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone To a solution of 17-ethyl-1-hydroxy-14-(tert-butyld imethylsiloxy)-12-[2'-(4''-(m-2'''-imidazoly lbenzyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone (20 mg in 600 μl tetrahydrofuran contained in a polypropylene vial) was added 75 μl of a solution of hydrogen fluoride-pyridine complex (40% in (2:1) tetrahydrofuran:pyridine) and the mixture stirred at room temperature. After 24 hours, the reaction was quenched by the careful addition of saturated sodium bicarbonate and extracted with ethyl acetate. The combined organics were dried over magnesium sulfate, concentrated in vacuo and purified by flash chromatography (ethyl acetate:hexane (4:1)+1% methanol, then 2% ammonium hydroxide, 5% methanol in methylene chloride) to give the title compound (7.2 mg).

MASS: (FAB) 948 (M+)

Partial $^1$H NMR δ: 7.89 (brs, 1H); 7.76 (d J=8 Hz, 1H); 7.13 (s, 1H); 5.31M, 5.19 m (brd J=3.0 Hz, 1H); 4.85 m, 4.20M (brs, 1H); 4.72 (s, 2H); 4.58 (brd J=4.0 Hz, 1H); 4.41 (brd J=14 Hz, 1H).

EXAMPLE 26

17-Ethyl-1,14-dihydroxy-12-[2'-(4''-(para-2'''-imidazolylbenzyloxy)-3''-methoxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 21–25 using p-(tert-butyldimethylsiloxymethyl)-benzyl trichloroacetimidate as the alkylating agent.

MASS (FAB) 948 (M+)

partial $^1$H NMR δ: 7.81(d J=9 Hz, 2H); 7.40(d J=9 Hz, 2H); 7.14(s, 2H); 5.34M, 5.20 m(brd J=3.0 Hz, 1H); 4.71(s, 2H); 4.41(brd J=14 Hz, 1H).

EXAMPLE 27

17-Ethyl-1,14-dihydroxy-12-[2'-(4''-(ortho-2'''-imidazolylbenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 21–25 using o-(tert-butyldimethylsiloxymethyl)-benzyl trichloroacetimidate as the alkylating agent.

MASS (FAB) 954 (M+Li), 948 (M+)

partial $^1$H NMR δ: 8.11(d J=8 Hz, 1H); 7.49(m, 2H); 7.37(m, 2H); 7.19(m, 2H); 5.38M, 5.25m(brd J=3.0 Hz, 1H); 4.41(brd J=14 Hz, 1H).

EXAMPLE 28

17-Ethyl-1,14-dihydroxy-12-[2'-(4''-(meta-1'''-methyl-2'''-imidazolylbenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Example 16 using the product of Example 25.

MASS (FAB) 962 (M+)

partial $^1$H NMR δ: 7.61(brs, 1H); 7.49(brd J=6 Hz, 1H); 7.41(m, 2H); 7.09(s, 1H); 6.94(S, 1H); 5.30M, 5.17 m(brd J=3.0 Hz, 1H); 4.71(J=5 Hz, 2H); 4.58(brd J=4.0 Hz, 1H); 4.41(brd J=14 Hz, 1H).3.72(s, 3H).

EXAMPLE 29

17-Ethyl-1,14-dihydroxy-12-]2'-(4''-(4'''-meta-difluorophenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Example 3–4 using 3,5-difluorophenylglyoxal as the dicarbonyl source.

MASS (FAB) 1007 (M+Na)

partial $^1$H NMR δ: 6.95(brs, 1H); 6.62(m, 3H); 5.29M. 5.16 m(brd, J=3 Hz, 1H); 4.41(brd J=14 Hz, 1H); 3.51(s, 2H).

EXAMPLE 30

17-Ethyl-1,14-dihydroxy-12-[2'-(4''-(4''',5''',6''',7'''-tetrahydro-2'''-benzimidazolylmethyloxy)-3''-methoxycyclohexyl-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone The title compound was prepared essentially as described in Examples 3–4 using 1,2-cyclohexanedione as the dicarbonyl source.

MASS (FAB) 926 (M+)

partial $^1$H NMR δ: 5.28M, 5.16 m(brd J=3 Hz, 1H); 4.41(brd, J=14 Hz, 1H); 3.72(d J=11 Hz, 1H); 3.43(s, 3H).

EXAMPLE 31

17-Ethyl-1,14-dihydroxy-12-[2'-(4''-allyloxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg in 3.0 ml 33% methylene chloride in cyclohexane), allyl trichloroacetimidate (88 μl neat) was added and the reagents allowed to mix for 5 minutes. Trifluoromethanesulfonic acid (4.5 μl neat) was added slowly via syringe and the mixture stirred at room temperature. After 18 hours the reaction was quenched by the addition of saturated sodium bicarbonate and extracted with ethyl acetate (3×5 ml). The combined organics were washed with brine and dried over magnesium sulfate. Purification of the concentrate by flash chromatography on silica gel (ethyl acetate:hexane (1:2)+1% methanol) gave the title compound (156 mg).

MASS: (FAB) 838 (M+Li)

Partial $^1$H NMR δ: 5.82 (m, 1H); 4.85 (m), 4.20 (brs, 1H); 4.59 (brd J=4.5 Hz, 1H); 4.41 (brd J=14 Hz, 1H); 4.03 (dt J=4.0, 1.0 Hz, 2H).

EXAMPLE 32

A.

17-Ethyl-1,14-dihydroxy-12-[2'-(4''-allyloxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1,14-dihydroxy-12-[2'-(3''-allyloxy-4''-hydroxycylohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg in 1.5 ml 33% methylene chlorine in cyclohexane), allyl trichloroacetimidate (53 μl neat) was added and the reagents allowed to mix for 5 minutes. Trifluoromethanesulfonic acid (2 μl neat) was added slowly via syringe and the mixture stirred at room temperature. After 3 hours the reaction was quenched by the addition of saturated sodium bicarbonate and extracted with ethyl acetate (3×5 ml). The combined organics were washed with brine and dried over magnesium sulfate. Purification of the concentrate by flash chromatography on silica gel (ethyl acetate:hexane (1:1)+1% methanol) gave the title compounds (21 mg 4''-ether; 17 mg 3''-ether).

A. (4''-ether):
Partial $^1$H NMR δ: 5.93 (m, 1H); 4.87 m, 4.19M (brs, 1H); 4.59 (brd J=4.0 Hz, 1H); 4.41 (brd J=14 Hz, 1H); 2.63 (brs, 1H).

B. (3''-ether):
Partial $^1$H NMR δ: 5.93 (m, 1H); 4.83 m, 4.23M (brs, 1H); 4.59 (brd J=4.0 Hz, 1H); 4.41 (brd J=14 Hz, 1H); 2.63 (brs, 1H).

EXAMPLE 33

A.
17-Ethyl-1,14-dihydroxy-12-[2'-(3''-hydroxy-4''-isopropoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B.
17-Ethyl-1,14-dihydroxy-12-[2'-(4''-hydroxy-3''-isopropoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (110 mg in 1.5 ml 33% methylene chloride in cyclohexane), isopropyl trichloroacetimidate (52 μl neat) was added and the reagents allowed to mix for 5 minutes. Trifluoromethanesulfonic acid (2 μl neat) was added slowly via syringe and the mixture stirred at room temperature. After 3 hours the reaction was quenched by the addition of saturated sodium bicarbonate and extracted with ethyl acetate (3×5 ml). The combined organics were washed with brine and dried over magnesium sulfate. Purification of the concentrate by preparative TLC on silica gel (ethyl acetate:hexane (1:1)+1% methanol) gave the title compounds (15 mg 4''-ether; 16 mg 3''-ether).

A. (4''-ether):
MASS: (FAB) 826 (M+Li)
Partial $^1$H NMR δ: 5.31 (d J=3.0 Hz, 1H); 4.85 m, 4.18M (brs, 1H); 4.58 (brd J=4.0 Hz, 1H); 4.40 (brd J=14 Hz, 1H); 2.63 (brs, 1H).

B. (3''-ether):
MASS: (FAB) 826 (M+Li)
Partial $^1$H NMR δ: 5.31 (d J=3.0 Hz, 1H); 4.81 m, 4.22M (brs, 1H); 4.58 (brd J=4.0 Hz, 1H); 4.40 (brd J=14 Hz, 1H); 2.60 (brs, 1H).

EXAMPLE 34

17-Ethyl-1-hydroxy-12-[2'-(4''-hydroxy-3''-isopropoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (69 mg in 3 ml 33% methylene chloride in cyclohexane), isopropyl trichloroacetimidate (22 μl neat) was added and the reagents allowed to mix for 5 minutes. Trifluoromethanesulfonic acid (2μl neat) was added slowly via syringe and the mixture stirred at room temperature. After 24 hours the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate:hexane (1:1)+1% methanol) gave the title compound (12 mg).

MASS: (FAB) 803 (M+Li)
Partial $^1$H NMR δ: 4.87 (brd J=10 Hz, 1H); 4.56 (d J=4.0 Hz, 1H); 4.42 m, 4.33M (brs, 1H); 2.61 (brs, 1H); 1.16 (d J=7.0 Hz, 6H).

EXAMPLE 35

A.
17-Ethyl-1,14-dihydroxy-12-[2'-(4''-sec-butenyloxy-3''-hydroxycyclohexyl)-1'-methylvinyl]-23,25-dimethoxy-13,19,21,17-tetramethyl-11,28-dioxa-4-azatricyclo[22.3.1.0$^{4,9}$]octacos-18-ene-2,3,10,16-tetraone and B.
17-Ethyl-1,14-dihydroxy-12-[2'-(3''-sec-butenyloxy-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg in 3 ml 33% methylene chloride in cyclohexane), sec-butenyl trichloroacetimidate (62 μl neat) was added and the reagents allowed to mix for 5 minutes. Trifluoromethanesulfonic acid (2 μl neat) was added slowly via syringe and the mixture stirred at room temperature. After 15 minutes the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate:hexane (1:1)+1% methanol) gave the title compounds (11 mg 4''-ether; 13 mg 3''-ether).

A. (4''-ether):
MASS: (FAB) 831 (M+Na)
Partial $^1$H NMR δ: 5.65 (m, 1H); 5.32 (brd J=3.0 Hz, 1H); 4.87 m, 4.18M (brs, 1H); 4.58 (brd J=4.0 Hz, 1H); 4.41 (brd J=14 Hz, 1H).

B. (3''-ether):
MASS: (FAB) 831 (M+Na)
Partial $^1$H NMR δ: 5.65 (m, 1H); 5.31 (brs, 1H); 4.28 m, 4.22M (brs, 1H); 4.58 (brd J=4.0 Hz, 1H); 4.41 (brd J=14 Hz, 1H).

EXAMPLE 36

17-Ethyl-1-hydroxy-12-[2'-(3'',4''-diallyloxy-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(3'',4'-'-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (20 mg in 0.75 ml 33% methylene chloride in cyclohexane), allyl trichloroacetimidate (16 μL neat) was added and the reagents allowed to mix for 5 minutes. Trifluoromethanesulfonic acid (2.0 μL neat) was added slowly via syringe and the mixture stirred at room temperature.

After 5 hours the reaction was quenched by the addition of saturated sodium bicarbonate and extracted with ethyl acetate (3×5 ml). The combined organics were washed with brine and dried over magnesium sulfate. Purification of the concentrate by flash chromatography on silica gel (ethyl acetate:hexane (1:3)+1% methanol) gave the title compound (6.8 mg). ($^1$H NMR was consistent with the desired structure).

EXAMPLE 37

17-Ethyl-1-hydroxy-12-[2'-(3",4"-di-(2'''-imidazolymethyl)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound is prepared from 17-ethyl-1-hydroxy-12-[2'-(3",4"-diallyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone essentially as described in Examples 12–13, then 1–2.

EXAMPLE 38

17-Ethyl-1,14-dihydroxy-12-[2'-(4"-(2-ethanaloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step A:

17-Ethyl-1-hydroxy-14-(tert-butyldimethylsiloxy)-12-[2'-(4"-(tert-butyldimethylsiloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (2.35 g) in dry methylene chloride (20 ml) was added an excess of 2,6-lutidine (1.04 ml) and the mixture was stirred at room temperature. After 10 minutes, tert-butyldimethylsilyl trifluoromethanesulfonate (1.50 ml) was added via syringe. After 1 hour the reaction mixture was diluted with ethyl acetate, extracted from saturated sodium bicarbonate, washed with brine and the organic phase dried over magnesium sulfate. Removal of the solvent in vacuo and flash chromatography on silica gel (ethyl acetate:hexane (1:3)+1% methanol) gave the title compound (2.91 g). ($^1$H NMR was consistent with the desired structure).

Step B:

17-Ethyl-1-hydroxy-14-(tert-butyldimethylsiloxy)-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(tert-butyldimethylsiloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (2.91 g) in acetonitrile (15 ml) was added a solution of 2% hydrogen fluoride in aqueous acetonitrile (2 ml), and the mixture stirred at room temperature. After 4 hours, the solution was diluted with ethyl acetate, extracted with saturated sodium bicarbonate solution and the organic phase dried over magnesium sulfate. Purification of the concentrate by flash chromatography on silica gel (ethyl acetate:hexane (1:1)+1% methanol) gave the title compound (1.51 g). ($^1$H NMR was consistent with the desired structure).

Step C:

17-Ethyl-1-hydroxy-14-(tert-butyldimethylsiloxy)-12-[2'-(4"-allyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (820 mg in 9 ml 33% methylene chloride in cyclohexane allyl trichloroacetimidate (366 μl neat) was added and the reagents allowed to mix for 5 minutes. Trifluoromethanesulfonic acid (16 μl neat) was added slowly via syringe and the mixture stirred at room temperature. After 17 hours the reaction was quenched by the addition of saturated sodium bicarbonate and extracted with ethyl acetate (3×15 ml). The combined organics were washed with brine and dried over magnesium sulfate. Purification of the concentrate by flash chromatography on silica gel (ether: hexane (2:3)) gave the title compound (800 mg). ($^1$H NMR was consistent with the desired structure).

Step D:

17-Ethyl-1-hydroxy-14-(tert-butyldimethylsiloxy)-12-[2'-(4"-(2''',3'''-dihydroxy propyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-alloyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (344 mg in 3 ml dry diethyl ether) was added 150 μl pyridine followed by 1.6 ml of a 0.25M osmium tetraoxide solution in THF and the mixture stirred at room temperature. After 15 minutes, 10 ml of a 20% sodium bisulfite solution were added and the mixture diluted with 20 ml ethyl acetate. The layers were separated and the organic portion re-extracted with 20% sodium bisulfite (3×20 ml) then washed with a saturated brine solution and dried over sodium sulfate. The concentrate was purified by flash chromatography on silica gel (ethyl acetate:hexane (1:1)+1% methanol, then methylene chloride:hexane:methanol (10:2:1)) to give the title compound (300 mg) ($^1$H NMR was consistent with the desired structure).

Step E:

17-Ethyl-1-hydroxy-14-(tert-butyldimethylsiloxy)-12-[2'-(4"-ethanaloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(2''',3'''-dihydroxypropyloxy)-3"-methoxycyclohexyl)-1'-methylvinyl]-23,25-dimethoxy-13,19,21,27-tetramethyl-11,28-dioxa-4-aza-tricyclo]22.3.1.0$^{4,9}$]octacos-18-ene-2,3,10,16-tetraone (284 mg 6 ml of in 20% aqueous tetrahydrofuran) was added sodium metaperiodate (72.3 mg) and the mixture stirred vigorously for 2 hours. At this time an additional 50 mg of sodium metaperiodate were added. After 1.5 hours the mixture was diluted with ethyl acetate and extracted from half-saturated sodium bicarbonate. The organic portion was dried over magnesium sulfate and purified by flash chromatography on silica gel (ethyl acetate:-hexane (1:1)+1% methanol) to give the title compound (151 mg). ($^1$H NMR was consistent with the desired structure).

Step F:
17-Ethyl-1,14-dihydroxy-12-[2'-(4''-(2-ethan aloxy)-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-ethyl-1-hydroxy-14-(tert-butyldimethylsiloxy)-12-[2'-(4''-(ethanaloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (3.5 mg) in acetonitrile (100 μl) is added a solution of 2% HF in aqueous acetonitrile (100 μl), and the mixture is stirred at room temperature. After 2 hours, the solution is diluted with ethyl acetate, extracted with saturated sodium bicarbonate solution and the organic phase is dried over magnesium sulfate. Purification of the concentrate by flash chromatography on silica gel gives the title compound.

EXAMPLE 39

17-Ethyl-1-hydroxy-12-[2'-(4''-(ethanoloxy)-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone Step A:
17-Ethyl-1-hydroxy-12-[2'-(4''-allyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (400 mg in 6 ml 33% methylene chloride in cyclohexane), allyl trichloroacetimidate (209 μl neat) was added and the reagents allowed to mix for 5 minutes. Trifluoromethanesulfonic acid (9 μl neat) was added slowly via syringe and the mixture stirred at room temperature. After 6 hours the reaction was quenched by the addition of saturated sodium bicarbonate and extracted with ethyl acetate (3×10 ml). The combined organics were washed with brine and dried over magnesium sulfate. Purification of the concentrate by flash chromatography on silica gel (ethyl acetate:hexane (1:3)+1% methanol) gave the title compound (320 mg). ($^1$H NMR was consistent with the desired structure).

Step B:
17-Ethyl-1-hydroxy-12-[2'-(4''-(2''',3'''-dihydroxypropyloxy)-3''-methoxycyclohexyl)-1'-methyl-vinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-allyloxy-3''-methoxycyclohexyl)-1'-methylvinyl]-23,25-dimethoxy-13,19,21,17-tetramethyl-11,28-dioxa-4-azatricyclo[22.3.1.0$^{4,9}$]octacos-18-ene-2,3,10,16-tetraone (310 mg in 3.5 ml dry ether) was added 350 μl pyridine followed by 1.5 ml of a 0.25M osmium tetraoxide solution in THF and the mixture stirred at room temperature. After 15 minutes, 10 ml of a 20% sodium bisulfite solution were added and the mixture diluted with 20 ml ethyl acetate. The layers were separated and the organic portion re-extracted with 20% sodium bisulfite (3×20 ml) then washed with a saturated brine solution and dried over sodium sulfate. The concentrate was purified by flash chromatography on silica gel (ethyl acetate:hexane (1:1)+1% methanol, then methylene chloride:hexane:methanol (10:2:1)) to give the title compound (232 mg). ($^1$H NMR was consistent with the desired structure).

Step C:
17-Ethyl-1-hydroxy-12-[2'-(4''-ethanaloxy-3''-methoxycyclohexyl)-1'-methylvinyl -23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-(2''',3'''-dihydroxypropyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (232 mg in 25% aqueous tetrahydrofuran) was added sodium metaperiodate (70.2 mg) and the mixture stirred vigorously. After 4 hours the mixture was diluted with ethyl acetate and extracted from half-saturated sodium bicarbonate. The organic portion was dried over magnesium sulfate and purified by flash chromatography on silica gel (ethyl acetate:hexane (1:1)+1% methanol) to give the title compound (112 mg). ($^1$H NMR was consistent with the desired structure).

EXAMPLE 40

17-Ethyl-1-hydroxy-14-(-tert-butyldimethylsiloxy)-12-[2'-(4''-(2-hydroxyethoxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1--hydroxy-14-(tert-butyldimethylsiloxy)-12-[2'-(4''-ethanaloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (126 mg in 1.3 ml dry terahydrofuran) at −78° C. was added potassium triphenylborohydride (320 μl of a 0.5M solution in THF). After 45 minutes, the reaction was quenched by the addition of saturated ammonium chloride and warmed to room temperature. The mixture was extracted with ethyl acetate (3×15 ml) and dried over magnesium sulfate. The concentrate was purified by flash chromatography on silica gel (ethyl acetate:hexane (2:1+1% methanol) to give the title compound (80.2 mg). ($^1$H NMR was consistent with the desired structure).

EXAMPLE 41

17-Ethyl-1-hydroxy-14-(tert-butyldimethylsiloxy)-12--[2'-(4''-(2''',3'''-dihydroxypropyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4''-allyloxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (1.0 g in 40 ml of tetrahydrofuran) was added 0.8 ml distilled water, followed by 1.2 g of 4-methylmorpholine-N-oxide hydrate and the mixture stirred at room temperature. After 15 minutes, osmium tetraoxide (1.16 ml of a 0.25M solution in THF) was added. The reaction was quenched after 6 hours by the addition of a 20% sodium bisulfite solution. Ethyl acetate was added and the layers separated. The organic portion was re-extracted with 20% sodium bisulfite (3×20 ml) then washed with a saturated brine solution and dried over sodium sulfate. The concentrate was purified by flash chromatography on silica gel (ethyl acetate:hexane (1:1)+1% methanol, then (4:1)+1% methanol) to give the title compound (680 mg).

($^1$H NMR consistent with the desired structure).

EXAMPLE 42

17-Ethyl-1,14-dihydroxy-12-[2'-(4''-(3'''-dioxolanylphenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tri(3-dioxolanylphenyl)bismuthine (300 mg., 0.46 mmol., 1.44 eq.) in methylene chloride (4 ml.) was added peracetic acid (0.100 ml., 32% in acetic acid) followed in 15 minutes by 17-ethyl-1,1,4-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (250 mg, 0.32 mmol, leq) and Cu(OAc)$_2$ (25 mg, 0.138 mmol, 0.43 eq). The reaction mixture was stirred at room temperature for 2 days. The mixture was then diluted with saturated aqueous sodium bicarbonate and extracted (2×methylene chloride). The extracts were combined, dried over anhydrus sodium sulfate, filtered, and concentrated in vacuo. The product was isolated and purified by preparative tlc on silica gel (3:1, hexane/acetone) to give the desired product (105 mg).

($^1$H NMR consistent with the desired structure.)

EXAMPLE 43

17-Ethyl-1,14-dihydroxy-12-[2'-(4''-(3'''-formylphenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-(3'''-dioxolanylphenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (20 mg in 1 ml methylene chloride) was added 1 ml of a 2.2% solution of p-toluensulfonic acid in methanol and the mixture stirred at room temperature. After 20 minutes the reaction was quenched by the addition of 2 ml saturated sodium bicarbonate, extracted with methylene chloride and washed with brine. The combined organics were dried over magnesium sulfate and the concentrate purified by preparative tlc on silica gel (2:1, hexane/acetone) to give the title compound (6 mg).

($^1$H NMR consistent with the desired structure).

EXAMPLE 44

17-Ethyl-1,14-dihydroxy-12-[2'-(-4''-(3'''-(2''''-imidazolyl)-phenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-(-3'''-formylphenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (50 mg in 0.75 ml methanol) was added glyoxal (25 µl of a 40% water solution) followed by ammonium hydroxide (75 µl of a 58% water solution) and the mixture stirred at room temperature. After 1.5 hours, the solution was concentrated in vacuo and the mixture purified by preparative tlc on silica gel (2:1 hexane/acetone) to give the title compound (20 mg). MASS (FAB) 940 (M+Li).

($^1$H NMR consistent with the desired structure).

EXAMPLE 45

17-Ethyl-1,14-dihydroxy-12-[2'-(4''-(4'''-para-tert--butylphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 3-4 using p-tert-butylphenylglyoxal as the dicarbonyl source.

MS (FAB) 1006 (M+H)

partial $^1$H NMR: 5.30M, 5.17 m (brs, 1H); 4.41(brd J=14 Hz, 1H); 3.58 m, 3.50M (s, 3H); 1.29 (s, 9H).

EXAMPLE 46

17-Ethyl-1,14-dihydroxy-12-[2'-(4''-(4'''-meta-trifluoromethylphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 3-4 using m-trifluoromethylphenylglyoxal as the dicarbonyl source.

MS (FAB) 1016 (M+H)

partial $^1$H NMR: 7.99 (s, 1H); 7.88 (t J=4 Hz, 1H); 7.43 (d J=5 Hz, 2H); 5.30M, 5.17 m (brs, 1H); 4.41 (brd J=14 Hz, 1H); 3.59 m, 3.52M (s, 3H).

EXAMPLE 47

17-Ethyl-1,14-dihydroxy-12-[2'-(4''-(4'''-metahydroxyphenyl-2'''-imidazolylmethyloxy)-3''-methoxycyclohexyl)-1'-methylvinyl]-23,25-dimethoxy-13,19,-21,27-tetramethyl-11,28-dioxa-4-azatricyclo[22.3.1.0$^{4,9}$]octacos-18-ene-2,3,10,16-tetraone The title compound was prepared essentially as described in Examples 3-4 using m-hydroxyphenylglyoxal as the dicarbonyl source.

MS (FAB) 964 (M+)

partial ¹H NMR: 6.99 (brd J=10 Hz, 1H); 6.70 (brd J=7 Hz, 2H); 5.30M, 5.17 m (brs, 1H); 4.41 (brd J=14 Hz, 1H);

EXAMPLE 48

17-Ethyl-1,14-dihydroxy-12-[2'-(4''-(4'''-(3'''',5''''-dichlorophenyl)-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 3-4 using 3,5-dichlorophenylglyoxal as the dicarbonyl source.

MS (FAB) 1039 (M+Na)

partial ¹H NMR: 7.60 (d J=2 Hz, 2H); 7.32 (d J=2 Hz, 1H); 7.15 (m, 1H); 5.30M, 5.17 m (brs, 1H); 4.41 (brd J=14 Hz, 1H); 3.60 m, 3.50M (s, 3H).

EXAMPLE 49

17-Ethyl-1,14-dihydroxy-12-[2'-(4''-(4'''-(3'''',4''''-difluorophenyl)-2'''-imidazolylmethyloxy)-3''-methoxycyclohexyl)-1'-methylvinyl]-23,25-dimethoxy-13,19,21,-27-tetramethyl-11,28-dioxa-4-azatricyclo[22.3.1.0$^{4,9}$]-octacos-18-ene-2,3,10,16-tetraone The title compound was prepared essentially as described in Examples 3-4 using 3,4-difluorophenylglyoxal as the dicarbonyl source.

MS (FAB) 1007 (M+Na)

partial ¹H NMR: 5.30M, 5.17 m (brs, 1H); 4.41 (brd J=14 Hz, 1H); 3.51 (s, 3H).

EXAMPLE 50

17-Ethyl-1,14-dihydroxy-12-[2'-(4''-(4'''-metamethoxyphenyl-2'''-imidazolylmethyloxy)-3''-methoxycyclohexyl)-1'-methylvinyl]-23,25-dimethoxy-13,19,21,-27-tetramethyl-11,28-dioxa-4-azatricyclo[22.3.1.0$^{4,9}$]-octacos-18-ene-2,3,10,16-tetraone The title compound was prepared essentially as described in Examples 3-4 using meta-methoxyphenylglyoxal as the dicarbonyl source.

MS (FAB) 978 (M+)

partial ¹H NMR: 6.75 (brd J=6 Hz, 1H); 5.30M, 5.17 m (brs, 1H); 4.41 (brd J=14 Hz, 1H); 3.83(s, 3H).

EXAMPLE 51

17-Ethyl-1,14-dihydroxy-12-[2'-(4''-(4'''-metamethoxyphenyl-2'''-imidazolylmethyloxy)-3''-methoxycyclohexyl)-1'-methylvinyl]-23,25-dimethoxy-13,19,21,-27-tetramethyl-11,28-dioxa-4-azatricyclo[22.3.1.0$^{4,9}$]-octacos-18-ene-2,3,10,16-tetraone, hydrochloride To a solution of 17-ethyl-1,14-dihydroxy-12-[2'-(4''-(4'''-meta-methoxyphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (45.8 mg) in methanol (0.5 mL) was added a solution of hydrochloric acid (2.5 μL of a 2N solution) and the mixture stirred at room temperature. After 10 minutes, the reaction is concentrated in vacuo, resolvated in benzene and lyopholyzed to give the title compound (47 mg). partial ¹H NMR: 6.87 (brd J=6 Hz, 1H); 5.30M, 5.17 m (brs, 1H); 4.41 (brd J=14 Hz, 1H); 3.85 (s, 3H); 3.56 (s, 3H).

EXAMPLE 52

17-Ethyl-1,14-dihydroxy-12-[2'-(4''-(4'''-(3'''',-4''''-methylenedioxyphenyl)-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 3-4 using 3,4-methylenedioxyphenylglyoxal as the dicarbonyl source.

MS (FAB) 993 (M+H)

partial ¹H NMR: 6.80 (d J=8 Hz, 2H); 5.30M, 5.17 m (brs, 1H); 4.41 (brd J=14 Hz, 1H); 3.52 (s, 3H).

EXAMPLE 53

17-Ethyl-1,14-dihydroxy-12-[2'-(4''-(4'''-metafluorophenyl-2'''-imidazolylmethyloxy)-3''-methoxycyclohexyl)-1'-methylvinyl]-23,25-dimethoxy-13,19,-21,27-tetramethyl-11,28-dioxa-4-azatricyclo[22.3.1.0$^{4,9}$]octacos-18-ene-2,3,10,16-tetraone The title compound was prepared essentially as described in Examples 3-4 using m-fluorophenylglyoxal as the dicarbonyl source.

MS (FAB) 967 (M+H)

partial ¹H NMR: 6.89 (brt J=6 Hz, 1H); 5.30M, 5.17 m (brs, 1H); 4.41 (brd J=14 Hz, 1H); 3.52 (s, 3H).

EXAMPLE 54

17-Ethyl-1,14-dihydroxy-12-[2'-(4''-(4'''-(3'''',-5''''-bis(trifluoromethyl)phenyl)-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 3-4 using 3,5-bis(trifluoromethyl)phenylglyoxal as the dicarbonyl source.

MS (FAB) 1085 (M+H)

partial ¹H NMR: 8.16 (s, 2H); 7.69 (s, 1H); 7.38 (s, 1H); 5.30M, 5.17 m (brs, 1H); 4.41 (brd J=14 Hz, 1H).

EXAMPLE 55

17-Ethyl-1,14-dihydroxy-12-[2'-(4''-(4'''-paramethoxyphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 3-4 using p-methoxyphenylglyoxal as the dicarbonyl source.

MS (FAB) 978 (M+)

partial ¹H NMR: 6.80 (d J=7 Hz, 1H); 5.30M, 5.17 m (brs, 1H); 4.41 (brd J=14 Hz, 1H); 3.80 (s, 3H).

EXAMPLE 56

17-Ethyl-1,14-dihydroxy-12-[2'-(4''-(4'''-(3'''',5''''-dimethoxyphenyl)-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 3-4 using 3,5-dimethoxyphenylglyoxal as the dicarbonyl source.

MS (FAB) 1009 (M+H)

partial ¹H NMR: 6.35 (s, 1H); 5.30M, 5.17 m (brs, 1H); 4.41 (brd J=14 Hz, 1H); 3.80(s, 6H).

EXAMPLE 57

17-Ethyl-1,14-dihydroxy-12-[2'-(4'''-meta-trifluoromethoxyphenyl-2'''-imidazolylmethyloxy)-3''-methoxycyclohexyl)-1'methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 3-4 using m-trifluoromethoxyphenylglyoxal as the dicarbonyl source.
MS (FAB) 1032 (M+)
partial $^1$H NMR: 7.35 (t J=5 Hz, 1H); 7.06 (brd J=6 Hz, 1H); 5.30M, 5.17 m (brs, 1H); 4.41 (brd J=14 Hz, 1H).

EXAMPLE 58

17-Ethyl-1,14-dihydroxy-12-[2'-(4''-(4'''-orthomethoxyphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 3-4 using p-methoxyphenylglyoxal as the dicarbonyl source.
MS (FAB) 978 (M+)
partial $^1$H NMR: 6.98 (m, 2H); 5.30M, 5.17 m (brs, 1H); 4.41 (brd J=14 Hz, 1H); 3.19 (s, 3H); 3.50 (s, 3H).

EXAMPLE 59

17-Ethyl-1,14-dihydroxy-12-[2'-(4''-(4'''-metaisopropoxyphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 3-4 using m-isopropoxyphenylglyoxal as the dicarbonyl source. partial $^1$H NMR: 6.65 (d J=6 Hz, 1H); 5.30M 5.17 m (brs, 1H); 4.41 (brd J=14 Hz, 1H); 1.23 (d J=5 Hz, 6H).

EXAMPLE 60

17-Ethyl-1,14-dihydroxy-12-[2'-(4''-(4'''-meta-ethoxyphenyl-2'''-imidazolylmethyloxy)-3''-methoxycyclohexyl)-1'-methylvinyl]-23,25-dimethoxy-13,19,-21,27-tetramethyl-11,28-dioxa-4-azatricyclo[22.3.1.0$^{4,9}$]octacos-18-ene-2,3,10,16-tetraone The title compound was prepared essentially as described in Examples 3-4 using m-ethoxyphenylglyoxal as the dicarbonyl source.
MS (FAB) 998 (M+Li)
partial $^1$H NMR: 6.75 (d J=6 Hz, 1H); 5.30M, 5.17 m (brs, 1H); 4.41 (brd J=14 Hz, 1H); 4.04 (q J=5 Hz, 2H); 1.37 (t J=4 Hz, 3H).

EXAMPLE 61

17-Ethyl-1,14-dihydroxy-12-[2'-(4''-(4'''-(3'''',-4'''',5''-'''-trimethoxyphenyl)-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 3-4 using 3,4,5-trimethoxyphenylglyoxal as the dicarbonyl source.
MS (FAB) 1039 (M+H)
partial $^1$H NMR: 6.93 (brs, 1H); 5.30M, 5.17 m (brs, 1H); 4.41 (brd J=14 Hz, 1H); 3.90 (s, 6H); 3.81 (s, 3H); 3.52 (s, 3H).

EXAMPLE 62

17-Ethyl-1,14-dihydroxy-12-[2'-(4''-(4'''-meta(hydroxyethyloxy)phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 3-4 using m-hydroxyethyloxyphenylglyoxal as the dicarbonyl source.
MS (FAB) 1009 (M+H)
partial $^1$H NMR: 6.94 (d J=6 Hz, 1H); 5.30M, 5.17 m (brs, 1H); 4.41 (brd J=14 Hz, 1H); 3.56 (s, 3H).

EXAMPLE 63

17-Ethyl-1,14-dihydroxy-12-[2'-(4''-(4'''-meta-propoxyphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 3-4 using m-propoxyphenylglyoxal as the dicarbonyl source.
MS (FAB) 1007 (M+H)
partial $^1$H NMR: 6.76 (d J=6 Hz, 1H); 5.30M, 5.17 m (brs, 1H); 4.41 (brd J=14 Hz, 1H).

EXAMPLE 64

17-Ethyl-1,14-dihydroxy-12-[2'-(4''-(4'''-metaisobutyloxyphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 3-4 using m-isobutyloxyphenylglyoxal as the dicarbonyl source. partial $^1$H NMR: 6.86 (d J=6 Hz, 1H); 5.30M, 5.17 m (brs, 1H); 4.41 (brd J=14 Hz, 1H); 0.99 (d J=5 Hz, 6H).

EXAMPLE 65

17-Ethyl-1,14-dihydroxy-12-[2'-(4''-(4'''--meta-methylphenyl-2'''-imidazolymethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 3-4 using m-methylphenylglyoxal as the dicarbonyl source.
partial $^1$H NMR: 7.02 (d J=6 Hz, 1H); 5.30M, 5.17 m (brs, 1H); 4.41 (brd J=14 Hz, 1H); 3.56 (s, 3H); 2.35(s, 3H).

EXAMPLE 66

17-Ethyl-1,14-dihydroxy-12-[2'-(4''-(4'''-(3''''-(2'''''-imidazolyl)-propyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Step A:
17-ethyl-1-hydroxy-14-(tert-butyldimethylsiloxy)-12-[2'-(4''-butenaloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1--hydroxy-14-(tert-butyldimethylsiloxy)-12-[2'-(4''-ethanaloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (94 mg in 1.0 mL methylene chloride was added (triphenylphosphoranylidene)acetaldehyde (60.2 mg) and the mixture stirred at room temperature. After 18 hours, the solvent was removed in vacuo and the mixture purified by flash chromatography on silica gel (ethyl acetate:hexane (1:2)+1% methanol) to give the title compound (62 mg). ($^1$H NMR consistent with the desired structure).

Step B:
17-ethyl-1-hydroxy-14-(tert-butyldimethylsiloxy)-12-[2'-(4''-butanaloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1--hydroxy-14-(tert-butyldimethylsiloxy)-12-[2'-(4''-butenaloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (62 mg in 1.0 mL of dry toluene) was added acetic acid (8 µL) and tetrakis(triphenylphosphine)palladium (3.1 mg) and the mixture stirred at room temperature. Finally, tributyltin hydride (17.2 µL) was added via syringe. After 15 minutes, the reaction was quenched by the addition of water (200 µL) and the mixture extracted from 20 mL acetonitrile:hexane (3:1). The acetonitrile layer was dried over magnesium sulfate, and the concentrate purified by flash chromatography on silica gel (ethyl acetate:hexane (1:2)+1% methanol) to give the title compound (58.8 mg). ($^1$H NMR consistent with the desired structure).

Step C & Step D:
17-ethyl-1,14-dihydroxy-12-[2'-(4''-(4'''-(3''''-(-2'''''-imidazolyl)-propyloxy)-3'-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Conducted essentially as described in Examples 3–4 using 40% aqueous glyoxal as the dicarbonyl source.
MS (FAB) 900 (M+)
partial $^1$H NMR: 6.92 (s, 2H); 5.30M, 5.17 m (brs, 1H); 4.41 (brd J=14 Hz, 1H).

EXAMPLE 67

17-Ethyl-1,14-dihydroxy-12-[2'-(4''-(4'''-hydroxymethyl-5''''-phenyl-2''''-imidazolylmethyloxy)-3''-methoxycyclohexyl()-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 9–10 using 1-phenyl-3 hydroxy-1,2-propanedione as the dicarbonyl source.
MS (FAB) 1009 (M+H)
partial $^1$H NMR: 6.83 (d J=6 Hz, 1H); 5.30M, 5.17 m (brs, 1H); 4.41 (brd J=14 Hz, 1H); 3.83 (s, 3H); 3.54 m, 3.50M (s, 3H).

EXAMPLE 68

17-Ethyl-1,14-dihydroxy-12-[2'-(4''-(meta-(4'''-(3''''-hydroxyphenyl)-2'''-imidazolyl)benzyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 21–25 using m-hydroxyphenylglyoxal as the dicarbonyl source.
MS (FAB) 1041 (M+H)
partial $^1$H NMR: 7.91 (s, 1H); 7.75 (m, 1H); 6.72 (m, 1H); 5.30M, 5.17 m (brs, 1H); 4.41 (brd J=14 Hz, 1H).

EXAMPLE 69

17-Ethyl-1,14-dihydroxy-12-[2'-(4''-(meta--(4'''-phenyl-2'''-imidazolyl)benzyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 21–25 using phenylglyoxal as the dicarbonyl source.
MS (FAB) 1031 (M+Li)
partial $^1$H NMR: 7.97 (s, 1H); 7.76 (m, 1H); 5.30M, 5.17 m (brs, 1H); 4.41 (brd J=14 Hz, 1H).

EXAMPLE 70

17-Ethyl-1,14-dihydroxy-12-[2'-(4''-(4'''-meta-dimethylphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 3–4 using m-dimethylphenylglyoxal as the dicarbonyl source.
MS (FAB) 978 (M+)
partial $^1$H NMR: 7.11 (d J=7 Hz, 1H); 5.30M, 5.17 m (brs, 1H); 4.41(brd J=14 Hz, 1H); 3.54 (s, 3H); 2.27 (s, 3H); 2.24 (s, 3H).

EXAMPLE 71

17-Ethyl-1,14-dihydroxy-12-[2'-(4''-(4'''-meta-ethylphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Examples 3–4 using m-ethylphenylglyoxal as the dicarbonyl source.
MS (FAB) 976 (M+)

partial $^1$H NMR: 7.28 (m, 5H); 7.06 (d J=7 Hz, 1H); 5.30M, 5.17 m (brs, 1H); 4.41 (brd J=14 Hz, 1H); 2.65 (q J=8 Hz, 2H); 1.24 (t J=8 Hz, 3H).

EXAMPLE 72

17-Ethyl-1,14-dihydroxy-12-[2'-(4'''-(4-''''-phenethyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone The title compound was prepared essentially as described in Examples 3–4 using phenethylglyoxal as the dicarbonyl source.

MS (FAB) 977 (M+H)
partial $^1$H NMR: 7.30 (m, 5H); 5.30M, 5.17 m (brs, 1H); 4.41 (brd J=14 Hz, 1H); 3.48 (s, 3H).

EXAMPLES 73–106

Utilizing the general procedures described in Examples 1 to 72, the following compounds of Formula I (wherein R$^4$ is hydrogen and n is 2) are prepared from the appropriately substituted starting materials and reagents.

| EXAMPLE NO. | R$^1$ | R$^2$ | R$^3$ | R$^5$ |
|---|---|---|---|---|
| 73 | 1H-imidazol-2-yl-CH$_2$CH$_2$– | CH$_3$CH$_2$ | H | CH$_3$CH$_2$ |
| 74 | 1H-imidazol-2-yl-CH$_2$CH$_2$– | CH$_3$CH$_2$ | OH | CH$_3$CH$_2$ |
| 75 | 1H-imidazol-2-yl-CH$_2$CH$_2$– | CH$_3$ | OH | CH$_2$=CHCH$_2$– |
| 76 | 1H-imidazol-2-yl-CH$_2$CH$_2$– | CH$_3$ | OH | CH$_3$CH$_2$CH$_2$ |
| 77 | 1H-imidazol-2-yl-CH$_2$CH$_2$– | (CH$_3$)$_2$CH– | OH | CH$_3$CH$_2$ |
| 78 | 1H-imidazol-2-yl-CH$_2$CH$_2$– | (CH$_3$)$_2$CHCH$_2$ | OH | CH$_3$CH$_2$ |
| 79 | 1H-imidazol-2-yl-CH$_2$CH$_2$– | CH$_2$=CHCH$_2$– | OH | CH$_3$CH$_2$CH$_2$ |
| 80 | 1H-imidazol-2-yl-CH$_2$CH$_2$– | (E)-PhCH=CHCH$_2$– | H | CH$_3$CH$_2$CH$_2$– |
| 81 | 4-(3-CF$_3$-phenyl)-1H-imidazol-2-yl-CH$_2$CH$_2$– | CH$_3$– | OH | CH$_3$CH$_2$ |

-continued

| EXAMPLE NO. | R¹ | R² | R³ | R⁵ |
|---|---|---|---|---|
| 82 | $CH_3CH_2$ | 2-(imidazolyl)ethyl | OH | $CH_3CH_2$ |
| 83 | $CH_3CH_2CH_2$ | 2-(imidazolyl)ethyl | OH | $CH_3CH_2$ |
| 84 | $(CH_3)_2CH-$ | 2-(imidazolyl)ethyl | OH | $CH_3CH_2$ |
| 85 | 2-(benzimidazolyl)ethyl | $CH_3$ | OH | $CH_3CH_2$ |
| 86 | 5-methyl-2-(benzimidazolyl)ethyl | $CH_3$ | OH | $CH_3CH_2$ |
| 87 | 5-fluoro-2-(benzimidazolyl)ethyl | $CH_3$ | OH | $CH_3CH_3$ |
| 88 | (imidazol-4-yl)ethyl | $CH_3$ | OH | $CH_3CH_2$ |
| 89 | (imidazol-4-yl)propenyl | $CH_3$ | OH | $CH_3CH_2$ |
| 90 | (benzimidazol-5-yl)methyl | $CH_3$ | OH | $CH_3CH_2$ |
| 91 | 2-(oxazolyl)ethyl | $CH_3$ | OH | $CH_3CH_2$ |
| 92 | 2-(thiazolyl)ethyl | $CH_3$ | OH | $CH_3CH_2$ |
| 93 | 2-(benzoxazolyl)ethyl | $CH_3$ | OH | $CH_3CH_2$ |

-continued

| EXAMPLE NO. | R¹ | R² | R³ | R⁵ |
|---|---|---|---|---|
| 94 | benzothiazol-2-yl-CH₂CH₂- | CH₃ | OH | CH₃CH₂ |
| 95 | oxazol-5-yl-CH₂- | CH₃ | OH | CH₃CH₂ |
| 96 | benzoxazol-6-yl-CH₂- | CH₃ | H | CH₃CH₂ |
| 97 | benzothiazol-6-yl-CH₂- | CH₃ | H | CH₃CH₂ |
| 98 | 1-(2-methoxyethyl)imidazol-2-yl-CH₂CH₂- | CH₃ | OH | CH₃CH₂ |
| 99 | 5-benzyl-1H-imidazol-2-yl-CH₂CH₂- | CH₃ | OH | CH₃CH₂ |
| 100 | 1H-benzimidazol-6-yl-CH₂- | CH₃ | OH | CH₃CH₂ |
| 101 | 1H-imidazol-2-yl-CH=CH-CH₂- | CH₃ | OH | CH₃CH₂ |
| 102 | 1H-imidazol-2-yl-CH₂CH₂CH₂- | CH₃ | OH | CH₃CH₂ |
| 103 | 3-(1H-imidazol-2-yl)phenyl-CH=CH- | CH₃ | OH | CH₃CH₂ |
| 104 | 3-(1H-imidazol-4-yl)phenyl-CH₂- | CH₃ | OH | CH₃CH₂ |

| EXAMPLE NO. | R¹ | R² | R³ | R⁵ |
|---|---|---|---|---|
| 105 | (2-methoxyphenyl with CH=N-NH-CH=CH- group, methylene linker) | $CH_3$ | OH | $CH_3CH_2$ |
| 106 | (3-fluorophenyl with CH=N-NH-CH=CH- group, methylene linker) | $CH_3$ | OH | $CH_3CH_2$ |

EXAMPLE 107

T-Cell Proliferation Assay

1. Sample Preparation

The compounds to be assayed were dissolved in absolute ethanol at 1 mg/ml.

2. Assay

Spleens from C57B1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 mM glutamine, 1 mM sodium pyruvate, $2 \times 10^{-5}$M 2-mercaptoethanol and 50 µg/ml gentamycin. Ionomycin was added at 250 ng/ml and PMA at 10 ng/ml. The cell suspension was immediately distributed into 96 well flat-bottom microculture plates (Costar) at 200 µl/well. The various dilutions of the compound to be tested were then added in triplicate wells at 20 µl/well. The compound 17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone was used as a standard. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were pulse-labelled with 2 µCi/well of tritiated thymidine (NEN, Cambridge, MA). After another 4 hours of incubation, cultures were harvested on glass fiber filters using a multiple sample harvester. Radioactivity of filter discs corresponding to individual wells was measured by standard liquid scintillation counting methods (Betacounter). Mean counts per minute of replicate wells were calculated and the results expressed as concentration of compound required to inhibit tritiated thymidine uptake of T-cells by 50%.

A selection of compounds were tested according to the previous procedure. The concentration of compound required to inhibit the proliferation of T-cells by 50% was measured, and the results were as follows.

The title compounds of the following Examples had activity in inhibiting the proliferation of T-cells in the aforementioned assay: 2, 4, 6, 8, 10, 11, 15, 16, 18, 20, 25, 26, 27, 28, 29, 30, 44, 45, 46, 47, 48, 49, 50, 51, 52, 53, 54, 55, 56, 57, 58, 59, 60, 61, 62, 63, 64, 65, 66, 67, 68, 69, 70, 71, and 72.

The results of this assay are representative of the intrinsic immunosuppressive activity of the compounds of the present invention.

For determining antagonist activity, the foregoing procedure is modified in that dilutions of compounds are cultured with 17-ally-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10, 16-tetraone (as a standard) at a concentration of 1.2 nM, a concentration which inhibits T cell proliferation by 100%, the concentration of compound required to reverse the inhibition obtained by the standard alone by 50% is measured, and the $ED_{50}$ value is determined.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

7. The compound of claim 6 which is:
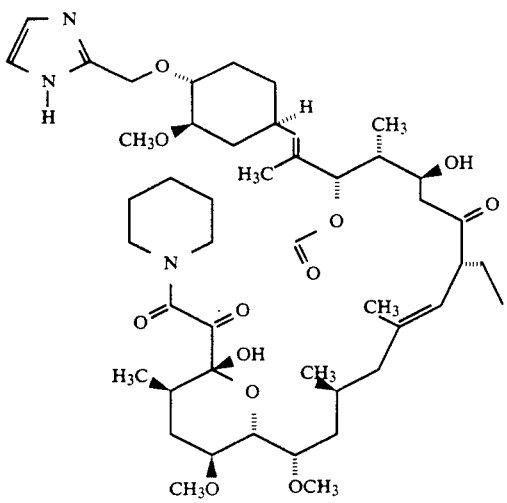
8. The compound of claim 6 which is:
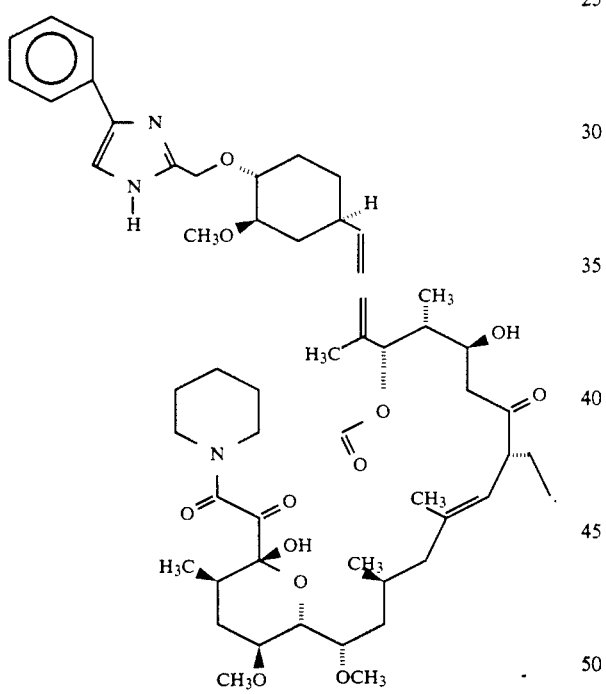
9. The compound of claim 6 which is:
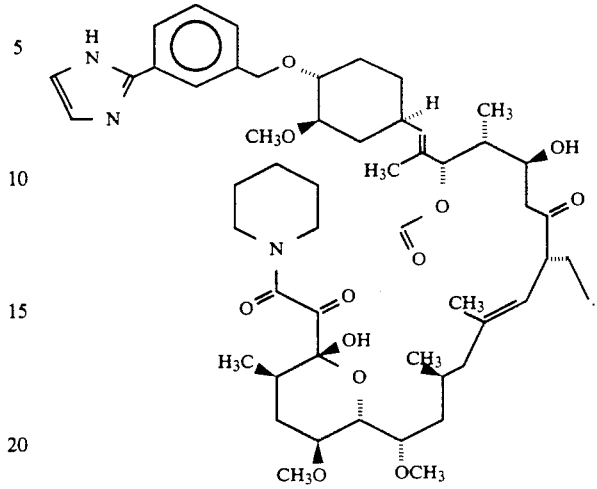
10. The compound of claim 6 which is:
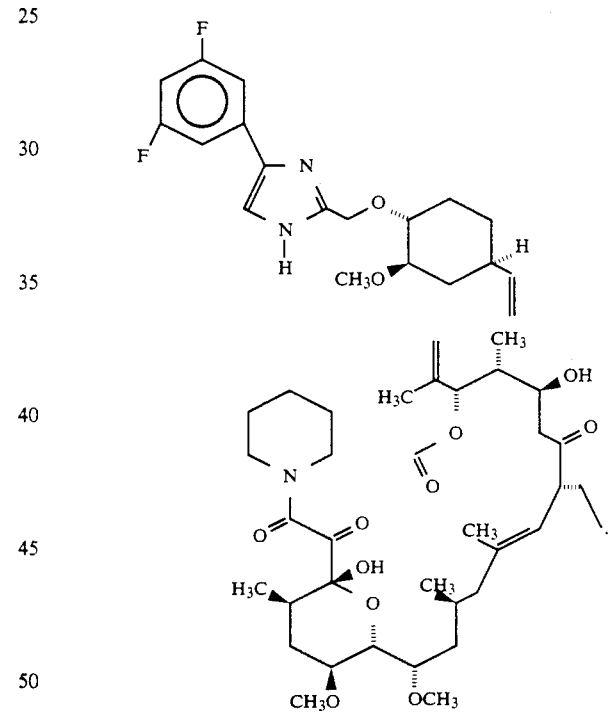
11. The compound of claim 6 which is:
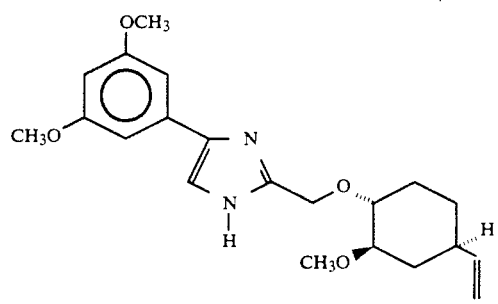

-continued
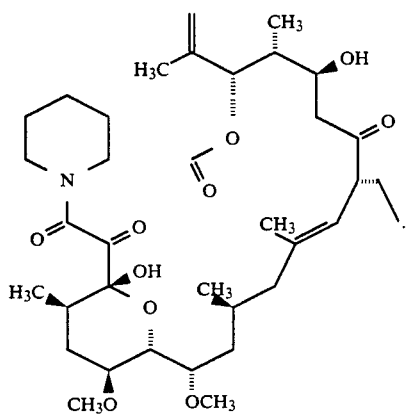
12. The compound of claim 6 which is:
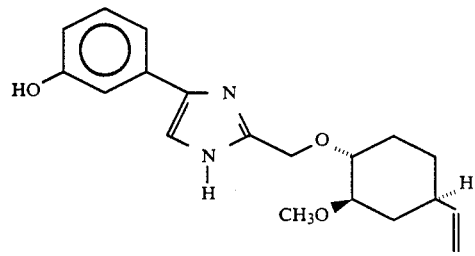
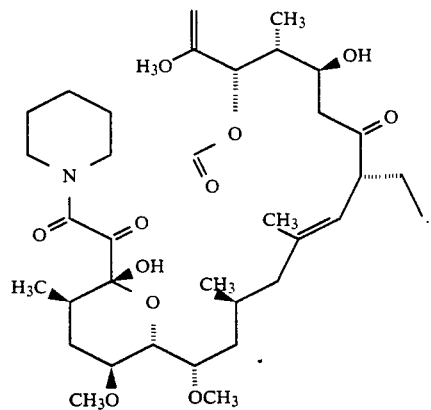
13. The compound of claim 6 which is:
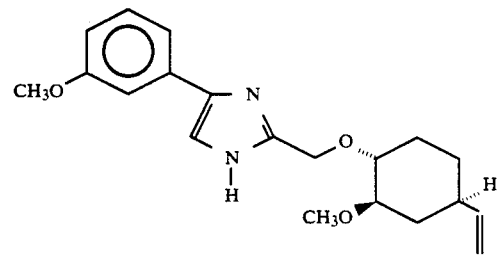

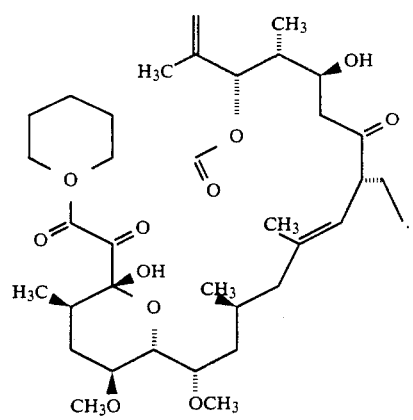

What is claimed is:

1. A compound of Formula I:

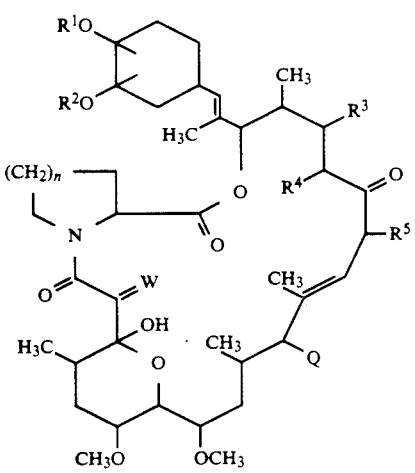

or a pharmaceutically acceptable salt thereof, wherein:
$R^1$ is selected from the group consisting of:

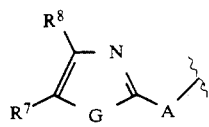

wherein G is N—$R^6$, O, S, SO, or $SO_2$,

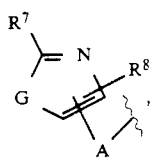

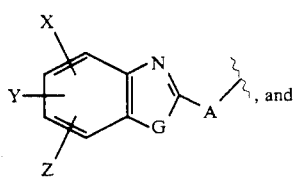

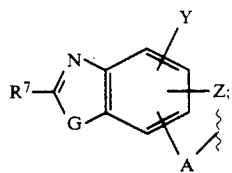

$R^2$ is independently selected from:
(1) the definitions of $R^1$;
(2) hydrogen;
(3) phenyl;
(4) substituted phenyl in which the substituents are X, Y and Z;
(5) 1- or 2-naphthyl;
(6) substituted 1- or 2-naphthyl in which the substituents are X, Y and Z;
(7) biphenyl;
(8) substituted biphenyl in which the substituents are X, Y and Z;
(9) $C_{1-10}$alkyl;
(10) substituted $C_{1-10}$alkyl in which one or more substituent(s) is(are) selected from:

(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl,
(g) —$NR^9R^{10}$, wherein $R^9$ and $R^{10}$ are independently selected from:
 (i) hydrogen, or
 (ii) $C_{1-6}$alkyl unsubstituted or substituted with one or more of the substituent(s) selected from:
  (a') phenyl, which may be substituted with X, Y and Z,
  (b') —OH,
  (c') $C_{1-6}$alkoxy,
  (d') -$CO_2H$,
  (e') -$CO_2$-$C_{1-6}$alkyl,
  (f') -$C_{3-7}$cycloalkyl, and
  (g') -$OR^{11}$,
 (iii) or where $R^9$ and $R^{10}$ and the N to which they are attached may form a heterocyclic ring selected from the group consisting of: morpholine, thiomorpholine, piperidine, and piperazine,
(h) —$NR^9CO$-$C_{1-6}$alkyl-$R^{10}$, wherein $R^9$ and $R^{10}$ are as defined above,
(i) —$COOR^9$, wherein $R^9$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z,
(q) —$OR^{11}$, and
(r) —$S(O)_p$—$C_{1-6}$alkyl;
(11) $C_{3-10}$alkenyl;
(12) substituted $C_{3-10}$alkenyl in which one or more substituent(s) is(are) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl,
(g) —$NR^9R^{10}$, wherein $R^9$ and $R^{10}$ are as defined above,
(h) —$NR^9CO$—$C_{1-6}$alkyl, wherein $R^9$ is as defined above,
(i) —$COOR^9$, wherein $R^9$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z;
(q) —$OR^{11}$, and
(r) —$S(O)_p$—$C_{1-6}$alkyl;

(13) $C_{3-10}$alkynyl;
(14) substituted $C_{3-10}$alkynyl in which one or more substituent(s) is(are) selected from:
  (a) hydroxy,
  (b) oxo,
  (c) $C_{1-6}$alkoxy,
  (d) phenyl-$C_{1-3}$alkoxy,
  (e) substituted phenyl-$C_{1-3}$alkoxy, in which the substituents on phenyl are X, Y and Z,
  (f) —OCO—$C_{1-6}$alkyl,
  (g) —$NR^9R^{10}$, wherein $R^9$ and $R^{10}$ are as defined above,
  (h) —$NR^9CO$—$C_{1-6}$alkyl, wherein $R^9$ is as defined above,
  (i) —$COOR^9$, wherein $R^9$ is as defined above,
  (j) —CHO,
  (k) phenyl,
  (l) substituted phenyl in which the substituents are X, Y and Z,
  (m) 1- or 2-naphthyl,
  (n) substituted 1- or 2-naphthyl in which the substituents are X, Y and Z,
  (o) biphenyl,
  (p) substituted biphenyl in which the substituents are X, Y and Z,
  (q) —$OR^{11}$; and
(15) —$R^{11}$;

$R^3$ is hydrogen, hydroxy, —$OR^{11}$, or $C_{1-6}$alkoxy;
$R^4$ is hydrogen, or $R^3$ and $R^4$ and taken together form a double bond;
$R^5$ is methyl, ethyl, propyl or allyl;
$R^6$ is selected from the group consisting of:
(1) hydrogen,
(2) $C_{1-6}$alkyl, unsubstituted or substituted with:
  (a) hydroxy,
  (b) $C_{1-6}$alkoxy,
  (c) —$NR^{12}R^{13}$, wherein $R^{12}$ and $R^{13}$ are independently selected from
    (i) hydrogen,
    (ii) $C_{1-6}$alkyl, or
    (iii) $C_{3-6}$alkenyl,
  (d) phenyl, unsubstituted or substituted with X, Y and Z,
  (e) —$OR^{11}$,
(3) $C_{3-6}$alkenyl, unsubstituted or substituted with:
  (a) hydroxy,
  (b) phenyl, unsubstituted or substituted with X, Y and Z, or
  (c) $C_{1-6}$alkoxy,
(4) phenyl, unsubstitued or substituted with X, Y and Z),
(5) —$R^{11}$,
(6) X, Y or Z;
$R^7$ and $R^8$ independently are selected from the group consisting of:
(1) hydrogen,
(2) $C_{1-7}$alkyl,
(3) $C_{2-6}$alkenyl,
(4) —$(CH_2)_m$—$NR^9R^{10}$, wherein $R^9$ and $R^{10}$ are as defined above, and m is 0, 1, 2, or 3
(5) —$CF_3$,
(6) —$CONR^9R^{10}$, wherein $R^9$ and $R^{10}$ are as defined above,
(7) $R^{14}O(CH_2)_m$—wherein $R^{14}$ is hydrogen, $C_{1-6}$alkyl, hydroxy-$C_{2-3}$alkyl, —$CF_3$, phenyl, $R^{11}$ or naphthyl and m is as defined above,
(8)

wherein $R^{14}$ and m are as defined above;
(9) phenyl-$(CH_2)_m$—wherein m is as defined above and the phenyl is unsubstituted or substituted with X, Y and Z,
(10) napthyl-$(CH_2)_m$—wherein m is as defined above and the napthyl is unsubstituted or substituted with X, Y and Z,
(11) biphenyl-$(CH_2)_m$—wherein m is as defined above and the biphenyl is unsubstituted or substituted with X, Y and Z,
(12) heteroaryl-$(CH_2)_m$—wherein heteroaryl is selected from: acridine, carbazole, cinnoline, dibenzofuran, dibenzothiophene, quinozaline, pyrrazole, indole, imidazole, benzotriazole, furan, benzofuran, quinoline, isoquinoline, pyrazine, pyridazine, pyridine, pyrimidine, and pyrrole, m is as defined above and the heteroaryl is unsubstituted or substituted with X, Y, and Z,
(13) morpholinyl, and
(14) —CH=CH-phenyl wherein the phenyl is unsubstituted or substituted with X, Y and Z;

$R^{11}$ is selected from:
(a) —$PO(OH)O^-M^+$, wherein $M^+$ is a positively charged inorganic or organic counterion, selected from the group consisting of: ammonium, sodium, lithium, potassium, calcium, magnesium, dicyclohexylamine, N-methyl-D-glucamine, arginine and lysine,
(b) —$SO_3^-M^+$,
(c) —$CO(CH_2)_qCO_2^-M^+$, wherein q is 1 to 3, and
(d) —$CO$-$C_{1-6}$alkyl—$NR^9R^{10}$, wherein $R^9$ and $R^{10}$ are as defined above and the alkyl is unsubstituted or substituted with one or more substituents selected from:
  (i) hydrogen,
  (ii) $C_{1-6}$alkoxy,
  (iii) —$NR^{12}R^{13}$, wherein $R^{12}$ and $R^{13}$ are as defined above,
  (iv) —$COOR^6$, wherein $R^6$ is as defined above,
  (v) phenyl,
  (vi) substituted phenyl in which the substituents are X, Y and Z,
  (vii) imidazolidyl,
  (viii) indolyl,
  (ix) —SH, and
  (x) —S—$C_{1-6}$alkyl;

A is selected from the group consisting of:
(1) a bond,
(2) $C_{1-10}$alkyl;
(3) substituted $C_{1-10}$alkyl in which one or more substituent(s) is(are) selected from:
  (a) hydroxy,
  (b) oxo,
  (c) $C_{1-6}$alkoxy,
  (d) phenyl-$C_{1-3}$alkoxy,
  (e) substituted phenyl-$C_{1-3}$alkoxy, in which the substituents on phenyl are X, Y and Z,
  (f) —OCO—$C_{1-6}$alkyl,
  (g) —$NR^9R^{10}$, wherein $R^9$ and $R^{10}$ are as defined above,
  (h) —$NR^9CO$—$C_{1-6}$alkyl, wherein $R^9$ is as defined above,
  (i) —$COOR^9$, wherein $R^9$ is as defined above, (j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z,
(q) —OR$^{11}$, and
(r) —S(O)$_p$—C$_{1-6}$alkyl;

(4) —C$_{1-10}$alkyl wherein one or more of the alkyl carbons is replaced by a group selected from: —NR$^9$—, —O—, —S(O)$_p$—, —CO$_2$—, —O$_2$C—, —CONR$^9$—, —NR$^9$CO—, —NR$^9$CONR$^{10}$—;

(5) —C$_{3-10}$alkenyl wherein alkenyl contains one to four double bonds and wherein one or more of the alkyl carbons is replaced by a group selected from: —NR$^9$—, —O—, —S(O)$_n$—, —CO$_2$—, —O$_2$C—, —CONR$^9$—, —NR$^9$CO—, and —NR$^9$CONR$^{10}$—;

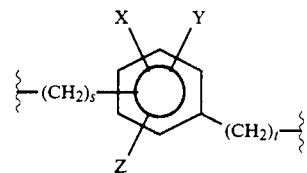

(6)

wherein s is 0 to 6 and t is 0 to 6,

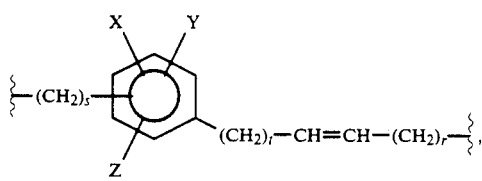

(7)

wherein r is 1 to 3 and s, and t are as defined above;
Q is hydrogen, hydroxy, —OR$^{11}$ or fluoro;
W is O or (H, OH);
X, Y and Z are independently selected from the group consisting of:
(a) hydrogen,
(b) C$_{1-10}$alkyl, unsubstituted or substituted with one or more substituents selected from:
  (i) aryl, wherein aryl is selected from the group consisting of phenyl and naphthyl,
  (ii) substituted aryl wherein aryl is as defined above and in which the substituents are X', Y' and Z',
  (iii) heteroaryl, wherein heteroaryl is as defined above,
  (iv) substituted heteroaryl wherein heteroaryl is as defined above in which the substituents are X', Y', and Z',
  (v) unsubstituted or substituted aryloxy, wherein aryl is as defined above and in which the substituents on aryl are X', Y' and Z',
  (vi) —OR$^9$,
  (vii) —OR$^{11}$,
  (viii) —OCOR$^9$,
  (ix) —OCO$_2$R$^9$,
  (x) —NR$^9$R$^{10}$,
  (xi) —CHO,
  (xii) —NR$^9$COC$_{1-6}$alkyl—R$^{10}$,
  (xiii) —NR$^9$CO$_2$C$_{1-6}$alkyl—R$^{10}$,
  (xiv) —NR$^9$CONR$^9$R$^{10}$,
  (xv) —OCONR$^9$R$^{10}$,
  (xvi) —CONR$^9$R$^{10}$,
(c) C$_{1-10}$alkyl wherein one or more of the alkyl carbons is replaced by a group selected from —NR$^9$—, —O—, —S(O)$_p$—, —CO$_2$—, —O$_2$C—, —CONR$^9$—, —NR$^9$CO—, —NR$^9$CONR$^{10}$—, —CO—, —CH(OH)—, alkenyl or alkynyl and the alkyl may be unsubstituted or substituted with one or more substituents selected from:
  (i) aryl, wherein aryl is as defined above,
  (ii) substituted aryl wherein aryl is as defined above and in which the substituents are X', Y' and Z',
  (iii) heteroaryl, wherein heteroaryl is as defined above,
  (iv) substituted heteroaryl wherein heteroaryl is as defined above and in which the substituents are X', Y', and Z',
  (v) unsubstituted or substituted aryloxy, in which the substituents on aryl are X', Y', and Z',
  (vi) —OR$^9$,
  (vii) —OR$^{11}$,
  (viii) —OCOR$^9$,
  (ix) —OCO$_2$R$^9$,
  (x) —NR$^9$R$^{10}$,
  (xi) —CHO
  (xii) —NR$^9$COC$_{1-6}$alkyl—R$^{10}$,
  (xiii) —NR$^9$CO$_2$C$_{1-6}$alkyl—R$^{10}$,
  (xiv) —NR$^9$CONR$^9$R$^{10}$,
  (xv) —OCONR$^9$R$^{10}$,
  (xvi) —CONR$^9$R$^{10}$,
(d) halogen,
(e) —NR$^9$R$^{10}$,
(f) —CN,
(g) —CHO,
(h) —CF$_3$,
(i) —SR$^{15}$, wherein R$^{15}$ is hydrogen, C$_{1-6}$alkyl, trifluoromethyl, or phenyl,
(j) —SOR$^{15}$,
(k) —SO$_2$R$^{15}$,
(l) —CONR$^9$R$^{10}$,
(m) R$^{16}$O(CH$_2$)$_m$— wherein R$^{16}$ is hydrogen, C$_{1-6}$alkyl, hydroxy-C$_{2-3}$alkyl, —CF$_3$, phenyl, R$^{11}$ or naphthyl and m is 0, 1, 2, or 3,
(n) —CH(OR$^{17}$)(OR$^{18}$), wherein R$^{17}$ and R$^{18}$ are C$_{1-3}$alkyl or taken together form an ethyl or propyl bridge,
(o)

wherein R$^{16}$ and m are as defined above,
(p)

wherein R$^{16}$ and m are as defined above, and
(q) —R$^{11}$;
or any two of X, Y and Z may be joined to form a saturated ring having 5, 6 or 7 ring atoms, said ring atoms comprising 1 or 2 oxygen atoms, the remaining ring atoms being carbon;
X', Y' and Z' independently are selected from:

(a) hydrogen,
(b) $C_{1-7}$alkyl,
(c) $C_{2-6}$alkenyl,
(d) halogen,
(e) $-(CH_2)_m-NR^9R^{10}$, wherein $R^9$, $R^{10}$ and m are as defined above,
(f) $-CN$,
(g) $-CHO$,
(h) $-CF_3$,
(i) $-SR^{15}$, wherein $R^{15}$ is as defined above,
(j) $-SOR^{15}$, wherein $R^{15}$ is as defined above,
(k) $-SO_2R^{15}$, wherein $R^{15}$ is as defined above,
(l) $-CONR^9R^{10}$, wherein $R^9$ and $R^{10}$ are as defined above,
(m) $R^{16}O(CH_2)_m-$, wherein $R^{16}$ and m are as defined above,
(n) $-CH(OR^{17})(OR^{18})$, wherein $R^{17}$ and $R^{18}$ are as defined above,
(o)

wherein $R^{16}$ and m are as defined above,
(p)

wherein $R^{16}$ and m are as defined above, and
(q) $-R^{11}$;
n is 1 or 2.

2. The compound according to claim 1 wherein the absolute configuration of Formula I is as defined in Formula III:

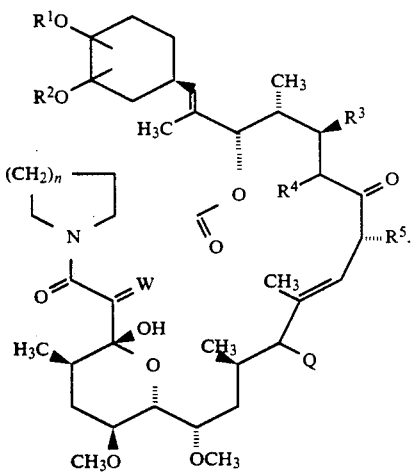

3. The compound according to claim 1 wherein:
$R^1$ is selected from:

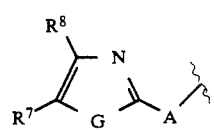

wherein G is $N-R^6$, O, or S,

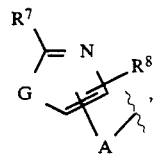

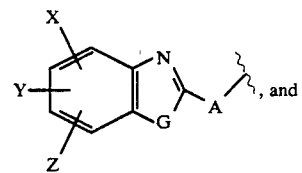

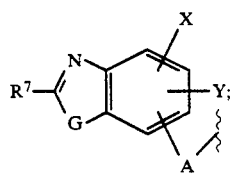

$R^2$ is independently selected from:
(1) hydrogen;
(2) phenyl;
(3) substituted phenyl in which the substituents are X, Y and Z;
(4) $C_{1-10}$alkyl;
(5) substituted $C_{1-10}$alkyl in which one or more substituent(s) is (are) selected from:
  (a) hydroxy,
  (b) $C_{1-6}$alkoxy,
  (c) phenyl-$C_{1-3}$alkoxy,
  (d) substituted phenyl-$C_{1-3}$alkoxy, in which the substituents on phenyl are X, Y and Z,
  (e) $-OCO-C_{1-6}$alkyl,
  (f) $-COOR^{20}$, wherein $R^{20}$ is hydrogen or $C_{1-6}$alkyl,
  (g) $-CHO$,
  (h) phenyl, and
  (i) substituted phenyl in which the substituents are X, Y and Z;
(6) $C_{3-10}$alkenyl;
(7) substituted $C_{3-10}$alkenyl in which one or more substituent(s) is (are) selected from:
  (a) hydroxy,
  (b) $C_{1-6}$alkoxy,
  (c) phenyl-$C_{1-3}$alkoxy,
  (d) substituted phenyl-$C_{1-3}$alkoxy, in which the substituents on phenyl are X, Y and Z,
  (e) $-OCO-C_{1-6}$alkyl,
  (f) $-COOR^{20}$, wherein $R^{20}$ is as defined above,
  (g) $-CHO$,
  (h) phenyl, and
  (i) substituted phenyl in which the substituents are X, Y and Z;
(8) $C_{3-10}$alkynyl;
(9) substituted $C_{3-10}$alkynyl in which one or more substituent(s) is (are) selected from:
  (a) hydroxy,
  (b) $C_{1-6}$alkoxy,
  (c) phenyl-$C_{1-3}$alkoxy,
  (d) substituted phenyl-$C_{1-3}$alkoxy, in which the substituents on phenyl are X, Y and Z,
  (e) $-OCO-C_{1-6}$alkyl,
  (f) $-COOR^9$, wherein $R^9$ is as defined above,
  (g) $-CHO$, (h) phenyl,
(i) substituted phenyl in which the substituents are X, Y and Z; and
(10) —$R^{11}$;

$R^3$ is hydrogen or hydroxy;
$R^4$ is hydrogen;
$R^5$ is ethyl, propyl or allyl;
$R^6$ is selected from the group consisting of:
(1) hydrogen,
(2) $C_{1-6}$alkyl, unsubstituted or substituted with:
  (a) hydroxy,
  (b) $C_{1-6}$alkoxy,
  (c) phenyl, unsubstituted or substituted with X, Y and Z,
  (d) —$OR^{11}$,
(3) $C_{3-6}$alkenyl, unsubstituted or substituted with:
  (a) hydroxy,
  (b) phenyl, unsubstituted or substituted with X, Y and Z, or
  (c) $C_{1-6}$alkoxy, and
(4) phenyl, unsubstituted or substituted with X, Y and Z,
(5) —$R^{11}$,
(6) X, Y or Z;

$R^7$ and $R^8$ independently are selected from the group consisting of:
(1) hydrogen,
(2) $C_{1-7}$alkyl,
(3) $C_{2-6}$alkenyl,
(4) —$CF_3$,
(5) $R^{14}O(CH_2)_m$— wherein $R^{14}$ is hydrogen, $C_{1-6}$alkyl, hydroxy-$C_{2-3}$alkyl, —$CF_3$, phenyl, $R^{11}$ or naphthyl and m is 0, 1, 2 or 3
(6)

wherein $R^{14}$ and m are as defined above;
(7) phenyl—$(CH_2)_m$— wherein m is as defined above and the phenyl is unsubstituted or substituted with X, Y and Z,
(8) heteroaryl—$(CH_2)_m$— wherein heteroaryl is selected from: acridine, carbazole, cinnoline, dibenzofuran, dibenzothiophene, quinozaline, pyrrazole, indole, imidazole, benzotriazole, furan, benzofuran, quinoline, isoquinoline, pyrazine, pyridazine, pyridine, pyrimidine, and pyrrole, wherein m is as defined above and the heteroaryl is unsubstituted or substituted with X, Y and Z, and
(9) —CH=CH—phenyl wherein the phenyl is unsubstituted or substituted with X, Y and Z;

$R^{11}$ is selected from:
(a) —$PO(OH)O^-M^+$, wherein $M^+$ is a positively charged inorganic or organic counterion, selected from the group consisting of: ammonium, sodium, lithium, potassium, calcium, magnesium, dicyclohexylamine, N-methyl-D-glucamine, arginine and lysine,
(b) —$SO_3^-M^+$,
(c) —$CO(CH_2)_qCO_2^-M^+$, wherein q is 1 to 3, and
(d) —CO—$C_{1-6}$alkyl—$NR^{20}R^{21}$, wherein $R^{20}$ is as defined above and $R^{21}$ is selected from the definitions of $R^{20}$;

A is selected from the group consisting of:
(1) a bond,
(2) $C_{1-10}$alkyl, and

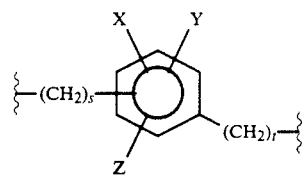

wherein s is 0 to 2 and t is 0 to 2;
Q is hydrogen, hydroxy, or fluoro;
W is O or (H, OH);
X, Y and Z are independently selected from the group consisting of:
(a) hydrogen,
(b) $C_{1-7}$alkyl,
(c) $C_{2-6}$alkenyl,
(d) halogen,
(e) —$(CH_2)_m$—$NR^{20}R^{21}$, wherein $R^{20}$, $R^{21}$ and m are as defined above,
(f) —$(CH_2)_m$—$CONR^{20}R^{21}$, wherein $R^{20}$, $R^{21}$ and m are as defined above,
(g) —$(CH_2)_m$—$NR^{20}$—$COR^{14}$, wherein $R^{14}$, $R^{20}$ and m are as defined above,
(h) —O—$(CH_2)_m$—$CONR^{20}R^{21}$, wherein $R^{20}$, $R^{21}$ and m are as defined above,
(i) —CN,
(j) —CHO,
(k) —$CF_3$,
(l) $R^{14}O(CH_2)_m$— wherein $R^{14}$ and m are as defined above,
(m) —$R^{11}$;
n is 1 or 2.

4. The compound according to claim 1 wherein:
$R^1$ is:

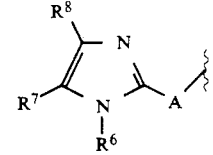

$R^2$ is hydrogen or methyl;
$R^3$ is hydrogen or hydroxy;
$R^4$ is hydrogen;
$R^5$ is ethyl, propyl or allyl;
$R^6$ is hydrogen, methyl, benzyl, 3-fluorobenzyl, $R^{11}$ or —$C_{1-4}$ alkyl-$OR^{11}$;
$R^7$ and $R^8$ are independently selected from hydrogen, methyl, $CH_3OCH_2$—, $HOCH_2$—, phenyl, 3,5-difluorophenyl, 3-fluorophenyl, 3,4-difluorophenyl, 3,5-dichlorophenyl, 3-methoxyphenyl, 3-trifluoromethylphenyl, 3-hydroxyphenyl, 4-hydroxyphenyl, 3,5-dihydroxyphenyl 4-tert-butylphenyl, 3,4-methylenedioxyphenyl, 3,5-trifluoromethylphenyl, 4-methoxyphenyl, 3,5-dimethoxyphenyl, 3-trifluoromethoxyphenyl, 3,5-di(trifluoromethoxy)phenyl, 2-methoxyphenyl, 3-isopropyloxyphenyl, 3-ethoxyphenyl, 3,5-diethoxyphenyl, 3,4,5-trimethoxyphenyl, 3-hydorxyethyloxyphenyl, 3-propyloxyphenyl, 3-isobutyloxyphenyl, 3-methylphenyl, 3,5-dimethylphenyl, 3-ethylphenyl, 3,5-diethylphenyl, and phenylethyl;
A is —$CH_2$—, phenyl, or benzyl;
Q is hydrogen or fluoro;

W is O or (H, OH);
n is 1 or 2;
and pharmaceutically acceptable salts thereof.

5. A compound which is selected from the group consisting of:

17-ethyl-1,14-dihydroxy-12-[2'-(4''-(2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'--(4''-(3''''-(2'''-imidazolyl)-propyloxy)-3''-methoxycyclohexyl)-1'-methylvinyl]-23,25-dimethoxy-13,19,21,27-tetramethyl-11,28-dioxa4-azatricyclo[22.3.1.0$^{4,9}$]octacos-18-ene-2,3,10,16-tetraone;

17-ethyl-1,14-dihydroxy-12-[2'-(4''--(4'''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''--(4'''-methyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.04,9]octacos-18-ene-2,3,10,16-tetraone;

17-ethyl-1,14-dihydroxy-12-[2'-(4''-(4'''-methyl-5''''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-methoxymethyl-5''''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''--(4'''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''--hydroxy-3''-(4'''-phenyl-2'''-imidazolylmethyloxy)-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(1'''-methyl-4''''-phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''--(1'''-benzyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(1'''-m--fluorobenzyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(m-2'''-imidazolylbenzyloxy)-341-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(para-2'''-imidazolylbenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(ortho-2'''-imidazolylbenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(meta-1'''-methyl-2'''-imidazolylbenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-meta-difluorophenyl-2'''-imidazolylbenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4''',5''',6''',7'''-tetrahydro-2'''-benzimidazolylmethyloxy)-3''--methoxycyclohexyl-1'-methylvinyl]-23,25-dimethoxy-13,19,21,-27-tetramethyl-11,28-dioxa-4-azatricyclo[22.3.1.0$^{4,9}$]octacos-18-ene-2,3,10,16-tetraone;

17-ethyl-1,14-dihydroxy-12[-2'-(4'''-(3'''-(2''''-imidazolyl)-phenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-(4'''-p-tert-butylphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-m--hydroxyphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.04,9]octacos-18-ene-2,3,10,16-tetraone;

17-ethyl-1,14-dihydroxy-12-[2'-(4''-(4'''-m-trifluoromethylphenyl-2'''-imidazolylmethyloxy)-3''-methoxycyclohexyl)-1'-methylvinyl]-23,25-dimethoxy-13,19,21,-27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-(3''''',5'''''-dichlorophenyl)-2'''-imidazolylmethyloxy)--3''-methoxycyclohexyl)-1'-methylvinyl]-23,25-dimethoxy-13,19,21,-27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-(3''''',4'''''-difluorophenyl)-2'''-imidazolylmethyloxy)--3''-methoxycyclohexyl)-1'methylvinyl[-23,25-dimethoxy-13,19,21,-27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-meta-methoxyphenyl-2'''-imidazolylmethyloxy)-3''-methoxycyclohexyl)-1'-methylvinyl]-23,25-dimethoxy-13,19,21,-27-tetramethyl-11,28-dioxa-4-azatricyclo[22.3.1.0$^{4,9}$]octacos-18-ene-2,3,10,16-tetraone, hydrochloride;

17-ethyl-1,14-dihydroxy-12-[2'-(4''-(4'''-meta-methoxyphenyl-2'''-imidazolylmethyloxy)-3''-methoxycyclohexyl)-1'-methylvinyl]-23,25-dimethoxy-13,19,21,-27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-meta-thiomethyl-phenyl-2'''-imidazolylmethyloxy)-3''-methoxycyclohexyl)-1'-methylvinyl]-23,25-dimethoxy-13,19,21,-27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-(3'''',4''''-methylenedioxyphenyl)-2'''-imidazolylmethyloxy)-3''-methoxycyclohexyl)-1'-methylvinyl[-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-metafluorophenyl-2'''-imidazolylmethyloxy)-3''-methoxycyclohexyl)-1'-methylvinyl]-23,25-dimethoxy-13,19,-21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-(3'''',-5''''-bis(trifluoromethyl)phenyl)-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-para-methoxyphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-(3'''',5''''-dimethoxyphenyl)-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-(3'''',5''''-dithiomethylphenyl)-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-(3'''',5''''-bis(trifluoromethoxy)phenyl)-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-meta-trifluoromethoxyphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-ortho-methoxyphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-metaisopropoxyphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-metaethoxyphenyl-2'''-imidazolylmethyloxy)-3''-methoxycyclohexyl)-1'-methylvinyl]-23,25-dimethoxy-13,19,-21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-(3'''',-4'''',5''''-trimethoxyphenyl)-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-meta-(hydroxyethyloxy)phenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-meta--propoxyphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-meta-isobutyloxyphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-meta--methylphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-(3''''-(2'''''-imidazolyl)-propyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-hydroxymethyl-5'''-phenyl-2'''-imidazolylmethyloxy)-3''-methoxycyclohexyl)-1'-methylvinyl]-23,25-dimethoxy13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(meta-(4'''-(3''''-hydroxyphenyl)-2'''-imidazolyl)benzyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(meta--(4'''-phenyl-2'''-imidazolyl)benzyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-meta-dimethylphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(4'''-meta-ethylphenyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(4'''-phenethyl-2'''-imidazolylmethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

or a pharmaceutically acceptable salt thereof.

6. A compound which is:

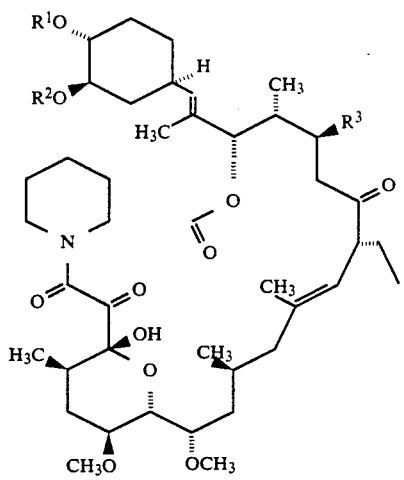

wherein $R^1$, $R^2$ and $R^3$ are selected from the following combinations of substituents:

| | $R^1$ | $R^2$ | $R^3$ |
|---|---|---|---|
| (a) | ![imidazolyl-ethyl] | CH₃ | OH |
| (b) | 4-methyl-imidazolyl-ethyl | CH₃ | OH |
| (c) | 4-phenyl-imidazolyl-ethyl | CH₃ | OH |
| (d) | 4-phenyl-imidazolyl-ethyl | H | H |
| (e) | H | 4-phenyl-imidazolyl-ethyl | H |

| | R¹ | R² | R³ |
|---|---|---|---|
| (f) | 4-phenyl-1-methyl-imidazol-2-yl | CH₃ | OH |
| (g) | 4-phenyl-5-methyl-1H-imidazol-2-yl | CH₃ | OH |
| (h) | 4-phenyl-5-(methoxymethyl)-1H-imidazol-2-yl | CH₃ | OH |
| (i) | 4-phenyl-1-methyl-imidazol-2-yl | H | OH |
| (j) | 4-phenyl-5-methyl-1H-imidazol-2-yl | H | OH |
| (k) | 4-phenyl-5-(methoxymethyl)-1H-imidazol-2-yl | H | OH |
| (l) | 4-(4-hydroxyphenyl)-1H-imidazol-2-yl | CH₃ | OH |

-continued
| | R¹ | R² | R³ |
|---|---|---|---|
| (m) | 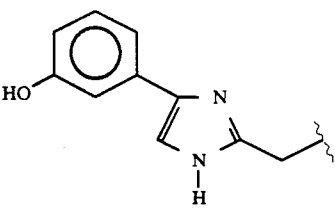 | CH₃ | OH |
| (n) | 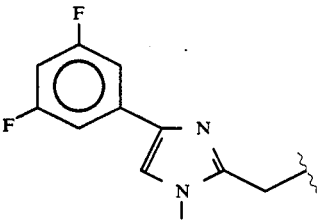 | CH₃ | OH |
| (o) | 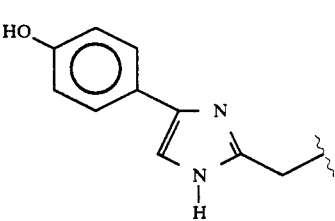 | H | OH |
| (p) | 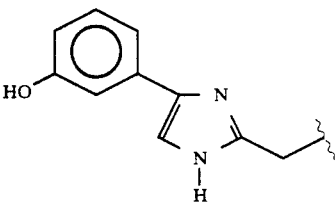 | H | OH |
| (q) | 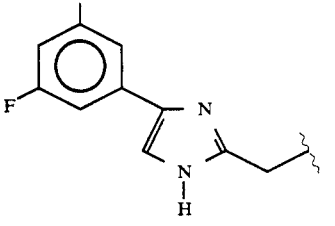 | H | OH |
| (r) | 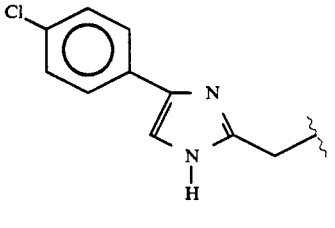 | CH₃ | OH |
| (s) | 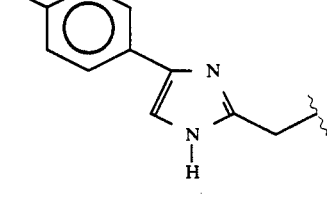 | H | OH |

-continued

| | R¹ | R² | R³ |
|---|---|---|---|
| (t) | 3,5-dichlorophenyl-imidazole | CH₃ | OH |
| (u) | 3,5-dichlorophenyl-imidazole | H | OH |
| (v) | 3-(trifluoromethyl)phenyl-imidazole | CH₃ | OH |
| (w) | 3-fluorophenyl-imidazole | CH₃ | OH |
| (x) | 3,4-difluorophenyl-imidazole | CH₃ | OH |
| (y) | 3-methoxyphenyl-imidazole | CH₃ | OH |
| (z) | 3,5-dimethoxyphenyl-imidazole | CH₃ | OH |

-continued

| | R¹ | R² | R³ |
|---|---|---|---|
| (aa) | 3,5-dimethoxyphenyl-imidazole (CH₃O groups on phenyl, linked via 2-position of 1H-imidazole) | H | OH |
| (bb) | 2-(4-substituted-phenyl)-1H-imidazole | CH₃ | OH |
| (cc) | 2-(2-substituted-phenyl)-1H-imidazole | CH₃ | OH |
| (dd) | 1-methyl-2-(3-substituted-phenyl)imidazole | CH₃ | OH |
| (ee) | 2-(3-substituted-phenyl)-1H-imidazole | CH₃ | OH |
| (ff) | 1-benzyl-imidazol-2-yl | CH₃ | OH |
| (gg) | 1-(3-fluorobenzyl)-imidazol-2-yl | CH₃ | OH |
| (hh) | 2-(3-substituted-phenyl)-1H-imidazole (alt.) | CH₃ | OH |